(12) United States Patent
Knust et al.

(10) Patent No.: US 8,324,248 B2
(45) Date of Patent: Dec. 4, 2012

(54) PIPERIDINE DERIVATIVES AS NK3 RECEPTOR ANTAGONISTS

(75) Inventors: Henner Knust, Rheinfelden (DE); Matthias Nettekoven, Grenzach-Wyhlen (DE); Hasane Ratni, Habsheim (FR); Claus Riemer, Freiburg (DE); Walter Vifian, Gelterkinden (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 162 days.

(21) Appl. No.: 12/692,680

(22) Filed: Jan. 25, 2010

(65) Prior Publication Data

US 2010/0197697 A1    Aug. 5, 2010

(30) Foreign Application Priority Data

Jan. 30, 2009   (EP) .................................... 09151722

(51) Int. Cl.
*A61K 31/445* (2006.01)
*C07D 401/14* (2006.01)

(52) U.S. Cl. ........ 514/317; 546/184; 546/186; 546/187; 514/315; 514/316

(58) Field of Classification Search ........... 546/184.186, 546/187; 514/315, 316, 317
See application file for complete search history.

(56) References Cited

U.S. PATENT DOCUMENTS 7,470,684 B2*   12/2008   Caroon et al. ............. 514/230.5
8,022,213 B2*   9/2011   Bissantz et al. ................ 546/18
8,063,075 B2*   11/2011   Jablonski et al. ............ 514/340

FOREIGN PATENT DOCUMENTS

WO   2005/110987   11/2005
WO   2009019163   2/2009
WO   2009024502   2/2009

OTHER PUBLICATIONS

Tooney et al., Neurosci. Letters, 2000, vol. 283 pp. 185-188.
Giardina et al., Exp. Opin. Ther. Patents, 2000, vol. 10, pp. 939-960.
Jung et al., Neuroscience, 1996, vol. 74, pp. 403-414.
Marco et al., Neuropeptides, 1998, vol. 32, pp. 481-488.
Kamali, F., Current Opinion in Investigational Drugs, 2001, vol. 2(7) pp. 950-956.

* cited by examiner

*Primary Examiner* — Golam M Shameem
(74) *Attorney, Agent, or Firm* — George W. Johnston; Patricia S. Rocha-Tramaloni; Kimberly J. Prior

(57) ABSTRACT

The present invention relates to a compounds of formula I

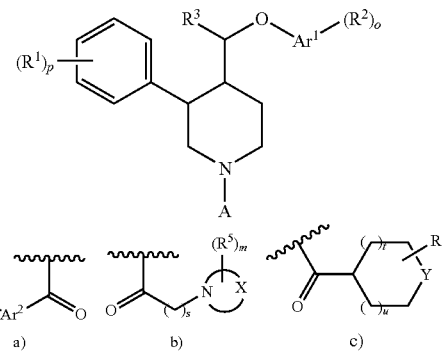

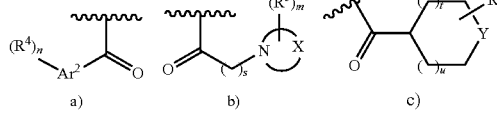

wherein
$A, Ar^1, Ar^2, R^1, R^2, R^3, R^4, R^5, R^6, m, n, o, p, s, t,$ and u are as defined herein
or to a pharmaceutically active salt, a racemic mixture, an enantiomer, an optical isomer or a tautomeric form thereof. the present compounds are high potential NK-3 receptor antagonists for the treatment of depression, pain, psychosis, Parkinson's disease, schizophrenia, anxiety and attention deficit hyperactivity disorder (ADHD).

5 Claims, No Drawings

PIPERIDINE DERIVATIVES AS NK3 RECEPTOR ANTAGONISTS

PRIORITY TO RELATED APPLICATION(S)

This application claims the benefit of European Patent Application No 09151722.7, filed Jan. 30, 2009, which is hereby incorporated by reference in its entirety.

BACKGROUND OF THE INVENTION

The three main mammalian tachykinins, substance P (SP), neurokinin A (NKA) and neurokinin B (NKB) belong to the family of neuropeptides sharing the common COOH-terminal pentapeptide sequence of Phe-X-Gly-Leu-Met-NH$_2$. As neurotransmitters, these peptides exert their biological activity via three distinct neurokinin (NK) receptors termed as NK-1, NK-2 and NK-3. SP binds preferentially to the NK-1 receptor, NKA to the NK-2 and NKB to the NK-3 receptor.

The NK-3 receptor is characterized by a predominant expression in CNS and its involvement in the modulation of the central monoaminergic system has been shown. These properties make the NK-3 receptor a potential target for central nervous system disorders such as anxiety, depression, bipolar disorders, Parkinson's disease, schizophrenia and pain (*Neurosci. Letters,* 2000, 283, 185-188; *Exp. Opin. Ther. Patents* 2000, 10, 939-960; *Neuroscience,* 1996, 74, 403-414; *Neuropeptides,* 1998, 32, 481-488).

Schizophrenia is one of the major neuropsychiatric disorders, characterized by severe and chronic mental impairment. This devastating disease affects about 1% of the world's population. Symptoms begin in early adulthood and are followed by a period of interpersonal and social dysfunction. Schizophrenia manifests as auditory and visual hallucinations, paranoia, delusions (positive symptoms), blunted affect, depression, anhedonia, poverty of speech, memory and attention deficits as well as social withdrawal (negative symptoms).

For decades scientists and clinicians have made efforts with the aim of discovering an ideal agent for the pharmacological treatment of schizophrenia. However, the complexity of the disorders, due to a wide array of symptoms, has hampered those efforts. There are no specific focal characteristics for the diagnosis of schizophrenia and no single symptom is consistently present in all patients. Consequently, the diagnosis of schizophrenia as a single disorder or as a variety of different disorders has been discussed but not yet resolved. The major difficulty in the development of a new drug for schizophrenia is the lack of knowledge about the cause and nature of this disease. Some neurochemical hypotheses have been proposed on the basis of pharmacological studies to rationalize the development of a corresponding therapy: the dopamine, the serotonin and the glutamate hypotheses. But taking into account the complexity of schizophrenia, an appropriate multireceptor affinity profile might be required for efficacy against positive and negative signs and symptoms. Furthermore, an ideal drug against schizophrenia would preferably have a low dosage allowing once-per-day dosage, due to the low adherence of schizophrenic patients.

In recent years clinical studies with selective NK1 and NK2 receptor antagonists appeared in the literature showing results for the treatment of emesis, depression, anxiety, pain and migraine (NK1) and asthma (NK2 and NK1). The most exciting data were produced in the treatment of chemotherapy-induced emesis, nausea and depression with NK1 and in asthma with NK2-receptor antagonists. In contrast, no clinical data on NK3 receptor antagonists have appeared in the literature until 2000. Osanetant (SR 142,801) from Sanofi-Synthelabo was the first identified potent and selective non-peptide antagonist described for the NK3 tachykinin receptor for the potential treatment of schizophrenia, which was reported in the literature (*Current Opinion in Investigational Drugs,* 2001, 2(7), 950-956 and *Psychiatric Disorders Study* 4, *Schizophrenia, June* 2003, Decision Recources, Inc., Waltham, Mass.). The proposed drug SR 142,801 has been shown in a phase II trial as active on positive symptoms of schizophrenia, such as altered behavior, delusion, hallucinations, extreme emotions, excited motor activity and incoherent speech, but inactive in the treatment of negative symptoms, which are depression, anhedonia, social isolation or memory and attention deficits.

The neurokinin-3 receptor antagonists have been described as useful in pain or inflammation, as well as in schizophrenia, *Exp. Opinion. Ther. Patents* (2000), 10(6), 939-960 and *Current Opinion in Investigational Drugs,* 2001, 2(7), 950-956 956 and *Psychiatric Disorders Study* 4, *Schizophrenia, June* 2003, Decision Recources, Inc., Waltham, Mass.).

SUMMARY OF THE INVENTION

The present invention provides compounds of formula I

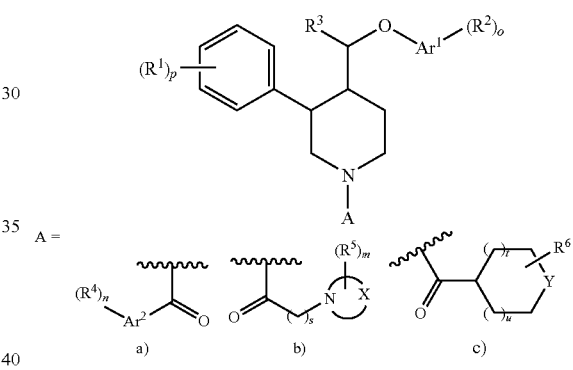

wherein
$Ar^1$ is aryl or a six-membered heteroaryl;
$Ar^2$ is aryl or a six-membered heteroaryl;
$R^1$ is hydrogen, halogen, lower alkyl, lower alkoxy or lower alkyl substituted by halogen;
$R^2$ is hydrogen, halogen, cyano, lower alkyl, or lower alkyl substituted by halogen;
$R^3$ is hydrogen or lower alkyl;
$R^4$ is hydrogen, lower alkyl, phenyl optionally substituted by halogen, a five-membered heteroaryl optionally substituted by lower alkyl, or aryl optionally substituted by halogen;

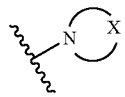

is a six-membered heterocyclic group, wherein X is —N(SO$_2$CH$_3$);
$R^6$ is hydrogen;
Y is —N(R$^{7'}$)—
$R^{7'}$ is a 6-membered heteroaryl group optionally substituted by cyano or is C(O)-cycloalkyl, wherein the cycloalkyl group is optionally substituted by lower alkyl, n is 1;
m is 1;
o is 1;
p is 1;
s is 0;
t is 1; and
u is 1;
or a pharmaceutically active salt, a racemic mixture, an enantiomer, an optical isomer or a tautomeric form thereof.

The invention includes all stereoisomeric forms, including individual diastereoisomers and enantiomers of the compound of formula (I) as well as racemic and non-racemic mixtures thereof.

The invention also provides pharmaceutical compositions containing a compound of the invention and a pharmaceutically acceptable carrier. The invention further provides methods for the manufacture of the compounds and compositions of the invention.

The present compounds are high potential NK-3 receptor antagonists for the treatment of depression, pain, bipolar disorders, psychosis, Parkinson's disease, schizophrenia, anxiety and attention deficit hyperactivity disorder (ADHD).

The preferred indications using the compounds of the present invention are depression, psychosis, Parkinson's disease, schizophrenia, anxiety and attention deficit hyperactivity disorder (ADHD).

DETAILED DESCRIPTION OF THE INVENTION

The following definitions of general terms used herein apply irrespective of whether the terms in question appear alone or in combination. It must be noted that, as used in the specification and the appended claims, the singular forms "a", "an," and "the" include plural forms unless the context clearly dictates otherwise.

As used herein, the term "lower alkyl" denotes a straight- or branched-chain hydrocarbon group containing from 1-8 carbon atoms, for example, methyl, ethyl, propyl, isopropyl, n-butyl, i-butyl, t-butyl and the like. Preferred lower alkyl groups are groups with 1-4 carbon atoms.

The term "lower alkyl substituted by halogen" denotes an alkyl group as defined above, wherein at least one hydrogen atom is replaced by halogen, for example —$CF_3$, —$CHF_2$, —$CH_2F$, —$CH_2CF_3$, —$CH_2CH_2CF_3$, —$CH_2CF_2CF_3$ and the like. Preferred lower alkyl substituted by halogen groups are groups having 1-4 carbon atoms.

The term "halogen" denotes chlorine, iodine, fluorine and bromine.

The term "alkoxy" denotes the group O—R, where R is an alkyl group as defined above.

The term "cycloalkyl" denotes a saturated carbon ring containing from 3-7 carbon atoms, for example, cyclopropyl, cyclobutyl, cyclpentyl, cyclohexyl, cycloheptyl, and the like.

The term "aryl" denotes a cyclic aromatic hydrocarbon radical consisting of one or more fused rings containing 6-14 carbon atoms in which at least one ring is aromatic in nature, for example phenyl, naphthyl, 1,2,3,4-tetrahydronaphthalenyl or indanyl. Preferred is the phenyl group.

The term "five- or six-membered heteroaryl" denotes a cyclic aromatic radical consisting of one or more fused rings containing 5-14 ring atoms, preferably containing 5-10 ring atoms, in which at least one ring is aromatic in nature, and which contains at least one heteroatom selected from N, O and S, for example quinoxalinyl, dihydroisoquinolinyl, pyrazin-2-yl, pyrazolyl, 2,4-dihydro-pyrazol-3-one, pyridinyl, pyridazinyl, isoxazolyl, benzo[1,3]dioxol, pyrimidin-4-yl, pyrimidin-5-yl, benzotriazol-5-yl, indolyl, benzoimidazol-5-yl, [1,3,4]-oxadiazolyl, [1,2.4]triazol-1-yl, [1,6]naphthyridin-2-yl, imidazo[4,5-b]pyridine-6-yl, tetrazolyl, thiazolyl, thiadiazolyl, thienyl, furyl, imidazol-1-yl, or benzofuranyl. Preferred five or six-membered heteroaryl group are indolyl, pyridinyl, pirimidinyl, pyridazinyl or [1,2,4]oxadiazol-3 and 5-yl.

The term "six-membered heterocyclic group" denotes a piperazinyl group.

"Pharmaceutically acceptable," such as pharmaceutically acceptable carrier, excipient, etc., means pharmacologically acceptable and substantially non-toxic to the subject to which the particular compound is administered.

The term "pharmaceutically acceptable acid addition salts" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methanesulfonic acid, p-toluenesulfonic acid and the like.

"Therapeutically effective amount" means an amount that is effective to prevent, alleviate or ameliorate symptoms of disease or prolong the survival of the subject being treated.

The following structures are encompassed by formula I of the present invention:

Compounds of formula Ia:

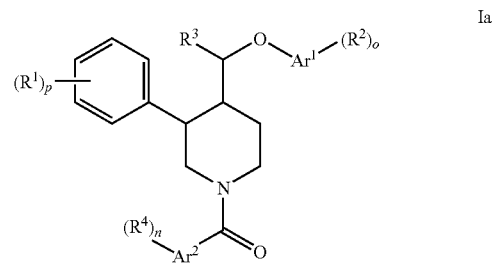

Ia wherein $Ar^1$ is aryl or a sixmembered heteroaryl;

$Ar^2$ is aryl or a six-membered heteroaryl;

$R^1$ is hydrogen, halogen, lower alkyl, lower alkoxy or lower alkyl substituted by halogen;

$R^2$ is hydrogen, halogen, cyano, lower alkyl, or lower alkyl substituted by halogen;

$R^3$ is hydrogen or lower alkyl;

$R^4$ is hydrogen, lower alkyl, phenyl optionally substituted by halogen, a five-membered heteroaryl optionally substituted by lower alkyl, or aryl optionally substituted by halogen;

n is 1;

o is 1; and p is 1;

or a pharmaceutically active salt, a racemic mixture, an enantiomer, an optical isomer or a tautomeric form thereof.

Compounds of formula Ib:

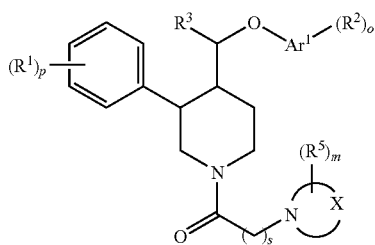

wherein
Ar¹ is aryl or a six-membered heteroaryl;
R¹ is hydrogen, halogen, lower alkyl, lower alkoxy or lower alkyl substituted by halogen;
R² is hydrogen, halogen, cyano, lower alkyl, or lower alkyl substituted by halogen;
R³ is hydrogen or lower alkyl;

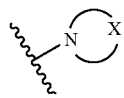

is a six-membered heterocyclic group, wherein X is —N(SO₂CH₃);
m is 1;
o is 1;
p is 1; and
s is 0;
or a pharmaceutically active salt, a racemic mixture, an enantiomer, an optical isomer or a tautomeric form thereof.

Compounds of formula Ic:

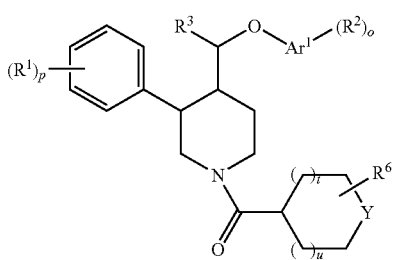

wherein
Ar¹ is aryl or a six-membered heteroaryl;
R¹ is hydrogen, halogen, lower alkyl, lower alkoxy or lower alkyl substituted by halogen;
R² is hydrogen, halogen, cyano, lower alkyl, or lower alkyl substituted by halogen
R³ is hydrogen or lower alkyl;
Y is —N(R⁷')—;
R⁷' is a 6-membered heteroaryl group optionally substituted by cyano or is C(O)-cycloalkyl, wherein the cycloalkyl group is optionally substituted by lower alkyl;
R⁶ is hydrogen;
p is 1;
o is 1;
t is 1; and
u is 1;

or a pharmaceutically active salt, a racemic mixture, an enantiomer, an optical isomer or a tautomeric form thereof.

Preferred compounds of formula Ia are those, wherein Ar¹ is a six-membered heteroaryl and Ar² is aryl, for example the following compounds
[(3RS,4RS)-3-(4-chloro-phenyl)-4-(5-chloro-pyridin-2-yloxymethyl)-piperidin-1-yl]-[4-(3-methyl-[1,2,4]oxadiazol-5-yl)-phenyl]-methanone;
[(3RS,4RS)-3-(4-chloro-phenyl)-4-(5-trifluoromethyl-pyridin-2-yloxymethyl)-piperidin-1-yl]-[4-(3-methyl-[1,2,4]oxadiazol-5-yl)-phenyl]-methanone;
{(3S,4S)-3-(4-chloro-phenyl)-4-[(S)-1-(5-chloro-pyridin-2-yloxy)-ethyl]-piperidin-1-yl}-[4-(3-methyl-[1,2,4]oxadiazol-5-yl)-phenyl]-methanone;
{(3S,4S)-3-(4-chloro-phenyl)-4-[(S)-1-(5-chloro-pyridin-2-yloxy)-ethyl]-piperidin-1-yl}-[4-(5-methyl-[1,2,4]oxadiazol-3-yl)-phenyl]-methanone;
{(3S,4S)-3-(4-chloro-phenyl)-4-[(S)-1-(5-trifluoromethyl-pyridin-2-yloxy)-ethyl]-piperidin-1-yl}-[4-(3-methyl-[1,2,4]oxadiazol-5-yl)-phenyl]-methanone;
{(3S,4S)-3-(4-chloro-phenyl)-4-[(S)-1-(5-trifluoromethyl-pyridin-2-yloxy)-ethyl]-piperidin-1-yl}-[4-(5-methyl-[1,2,4]oxadiazol-3-yl)-phenyl]-methanone;
6-((S)-1-{(3S,4S)-3-(4-chloro-phenyl)-1-[4-(3-methyl-[1,2,4]oxadiazol-5-yl)-benzoyl]-piperidin-4-yl}-ethoxy)-nicotinonitrile;
6-((S)-1-{(3S,4S)-3-(4-chloro-phenyl)-1-[4-(5-methyl-[1,2,4]oxadiazol-3-yl)-benzoyl]-piperidin-4-yl}-ethoxy)-nicotinonitrile;
6-{(S)-1-[(3S,4S)-3-(4-chloro-phenyl)-1-(4'-fluoro-biphenyl-4-carbonyl)-piperidin-4-yl]-ethoxy}-nicotinonitrile; and
[(3SR,4SR)-4-(5-chloro-pyridin-2-yloxymethyl)-3-(3,4-difluoro-phenyl)-piperidin-1-yl]-[4-(3-methyl-[1,2,4]oxadiazol-5-yl)-phenyl]-methanone.

Preferred compounds of formula Ia are further those, wherein both Ar¹ and Ar² are six-membered heteroaryl, for example the following compounds
{(3S,4S)-3-(4-chloro-phenyl)-4-[(S)-1-(5-chloro-pyridin-2-yloxy)-ethyl]-piperidin-1-yl}-(6-methyl-pyridazin-4-yl)-methanone;
{(3S,4S)-3-(4-chloro-phenyl)-4-[(S)-1-(5-trifluoromethyl-pyridin-2-yloxy)-ethyl]-piperidin-1-yl}-(6-methyl-pyridazin-4-yl)-methanone; and
6-{(S)-1-[(3S,4S)-3-(4-chloro-phenyl)-1-(6-methyl-pyridazine-4-carbonyl)-piperidin-4-yl]-ethoxy}-nicotinonitrile.

Further preferred compounds are compounds of formula Ib, wherein Ar¹ is a six-membered heteroaryl and X is —N(SO₂CH₃), for example the following compounds
{(3S,4S)-3-(4-chloro-phenyl)-4-[(S)-1-(5-chloro-pyridin-2-yloxy)-ethyl]-piperidin-1-yl}-(4-methanesulfonyl-piperazin-1-yl)-methanone;
{(3S,4S)-3-(4-chloro-phenyl)-4-[(S)-1-(5-trifluoromethyl-pyridin-2-yloxy)-ethyl]-piperidin-1-yl}-(4-methanesulfonyl-piperazin-1-yl)-methanone; and
6-{(S)-1-[(3S,4S)-3-(4-chloro-phenyl)-1-(4-methanesulfonyl-piperazine-1-carbonyl)-piperidin-4-yl]-ethoxy}-nicotinonitrile.

Preferred compounds of formula Ic are those, wherein Ar¹ is a six-membered heteroaryl and Y is NR⁷', for example the following compounds
{4-[(3RS,4RS)-3-(4-chloro-phenyl)-4-(5-trifluoromethyl-pyridin-2-yloxymethyl)-piperidine-1-carbonyl]-piperidin-1-yl}-(1-methyl-cyclopropyl)-methanone;

{4-[(3RS,4RS)-3-(4-chloro-phenyl)-4-(5-chloro-pyridin-2-yloxymethyl)-piperidine-1-carbonyl]-piperidin-1-yl}-(1-methyl-cyclopropyl)-methanone;

(4-{(3SR,4 SR)-3-(4-chloro-phenyl)-4-[(SR)-1-(5-chloro-pyridin-2-yloxy)-ethyl]-piperidine-1-carbonyl}-piperidin-1-yl)-(1-methyl-cyclopropyl)-methanone;

(4-{(3S,4S)-3-(4-chloro-phenyl)-4-[(S)-1-(5-chloro-pyridin-2-yloxy)-ethyl]-piperidine-1-carbonyl}-piperidin-1-yl)-(1-methyl-cyclopropyl)-methanone;

(4-{(3R,4R)-3-(4-chloro-phenyl)-4-[(R)-1-(5-chloro-pyridin-2-yloxy)-ethyl]-piperidine-1-carbonyl}-piperidin-1-yl)-(1-methyl-cyclopropyl)-methanone;

4-{(3S,4S)-3-(4-chloro-phenyl)-4-[(S)-1-(5-chloro-pyridin-2-yloxy)-ethyl]-piperidine-1-carbonyl}-3,4,5,6-tetrahydro-2H-[1,2']bipyridinyl-5'-carbonitrile;

4-{(3S,4S)-3-(4-chloro-phenyl)-4-[(S)-1-(5-trifluoromethyl-pyridin-2-yloxy)-ethyl]-piperidine-1-carbonyl}-3,4,5,6-tetrahydro-2H-[1,2']bipyridinyl-5'-carbonitrile;

6-((S)-1-{(3S,4S)-3-(4-chloro-phenyl)-1-[1-(1-methyl-cyclopropanecarbonyl)-piperidine-4-carbonyl]-piperidin-4-yl}-ethoxy)-nicotinonitrile;

4-{(3S,4S)-3-(4-chloro-phenyl)-4-[(S)-1-(5-cyano-pyridin-2-yloxy)-ethyl]-piperidine-1-carbonyl}-3,4,5,6-tetrahydro-2H-[1,2']bipyridinyl-5'-carbonitrile;

{4-[(3SR,4SR)-4-(5-chloro-pyridin-2-yloxymethyl)-3-(3,4-difluoro-phenyl)-piperidine-1-carbonyl]-piperidin-1-yl}-(1-methyl-cyclopropyl)-methanone;

4-[(3S,4S)-4-(5-chloro-pyridin-2-yloxymethyl)-3-(3,4-difluoro-phenyl)-piperidine-1-carbonyl]-3,4,5,6-tetrahydro-2H-[1,3']bipyridinyl-6'-carbonitrile;

4-[(3S,4S)-4-(5-chloro-pyridin-2-yloxymethyl)-3-phenyl-piperidine-1-carbonyl]-3,4,5,6-tetrahydro-2H-[1,2']bipyridinyl-5'-carbonitrile;

4-{(3S,4S)-3-(4-chloro-phenyl)-4-[(S)-1-(3,4-dichloro-phenoxy)-ethyl]-piperidine-1-carbonyl}-3,4,5,6-tetrahydro-2H-[1,2']bipyridinyl-5'-carbonitrile;

4-{(3S,4S)-3-(4-chloro-phenyl)-4-[(S)-1-(4-trifluoromethyl-phenoxy)-ethyl]-piperidine-1-carbonyl}-3,4,5,6-tetrahydro-2H-[1,2']bipyridinyl-5'-carbonitrile;

4-{(3S,4S)-3-(4-chloro-phenyl)-4-[(S)-1-(4-cyano-phenoxy)-ethyl]-piperidine-1-carbonyl}-3,4,5,6-tetrahydro-2H-[1,2']bipyridinyl-5'-carbonitrile;

4-{(3S,4S)-3-(4-chloro-phenyl)-4-[(S)-1-(5-fluoro-pyridin-2-yloxy)-ethyl]-piperidine-1-carbonyl}-3,4,5,6-tetrahydro-2H-[1,2']bipyridinyl-5'-carbonitrile;

4-{(3S,4S)-3-(4-chloro-phenyl)-4-[(S)-1-(4-fluoro-phenoxy)-ethyl]-piperidine-1-carbonyl}-3,4,5,6-tetrahydro-2H-[1,2']bipyridinyl-5'-carbonitrile;

4-{(3S,4S)-3-(4-chloro-phenyl)-4-[(S)-1-(3,4-difluoro-phenoxy)-ethyl]-piperidine-1-carbonyl}-3,4,5,6-tetrahydro-2H-[1,2']bipyridinyl-5'-carbonitrile;

4-[(3S,4S)-4-[(S)-1-(4-chloro-phenoxy)-ethyl]-3-(4-chloro-phenyl)-piperidine-1-carbonyl]-3,4,5,6-tetrahydro-2H-[1,2']bipyridinyl-5'-carbonitrile;

4-{(3S,4S)-3-(4-chloro-phenyl)-4-[(S)-1-(3-fluoro-phenoxy)-ethyl]-piperidine-1-carbonyl}-3,4,5,6-tetrahydro-2H-[1,2']bipyridinyl-5'-carbonitrile;

4-[(3S,4S)-3-(4-chloro-phenyl)-4-((S)-1-p-tolyloxy-ethyl)-piperidine-1-carbonyl]-3,4,5,6-tetrahydro-2H-[1,2']bipyridinyl-5'-carbonitrile;

4-{(3S,4S)-3-(4-cloro-phenyl)-4-[(S)-1-(5-methyl-pyridin-2-yloxy)-ethyl]-piperidine-1-carbonyl}-3,4,5,6-tetrahydro-2H-[1,2']bipyridinyl-5'-carbonitrile;

4-{(3S,4S)-3-(4-chloro-phenyl)-4-[(S)-1-(5-fluoro-pyrimidin-2-yloxy)-ethyl]-piperidine-1-carbonyl}-3,4,5,6-tetrahydro-2H-[1,2']bipyridinyl-5'-carbonitrile;

4-[(3S,4S)-4-[(S)-1-(5-chloro-pyridin-2-yloxy)-ethyl]-3-(3,4-difluoro-phenyl)-piperidine-1-carbonyl]-3,4,5,6-tetrahydro-2H-[1,2']bipyridinyl-5'-carbonitrile;

{4-[(3S,4S)-4-[(S)-1-(5-chloro-pyridin-2-yloxy)-ethyl]-3-(3,4-difluoro-phenyl)-piperidine-1-carbonyl]-piperidin-1-yl}-(1-methyl-cyclopropyl)-methanone;

4-[(3S,4S)-4-[(S)-1-(5-cyano-pyridin-2-yloxy)-ethyl]-3-(3,4-difluoro-phenyl)-piperidine-1-carbonyl]-3,4,5,6-tetrahydro-2H-[1,2']bipyridinyl-5'-carbonitrile;

6-((S)-1-{(3S,4S)-3-(3,4-difluoro-phenyl)-1-[1-(1-methyl-cyclopropanecarbonyl)-piperidine-4-carbonyl]-piperidin-4-yl}-ethoxy)-nicotinonitrile; and 4-{(3S,4S)-3-(4-chloro-phenyl)-4-[(SR)-1-(5-cyano-pyridin-2-ylamino)-ethyl]-piperidine-1-carbonyl}-3,4,5,6-tetrahydro-2H-[1,2']bipyridinyl-5'-carbonitrile.

An embodiment of the invention are compounds of formula II

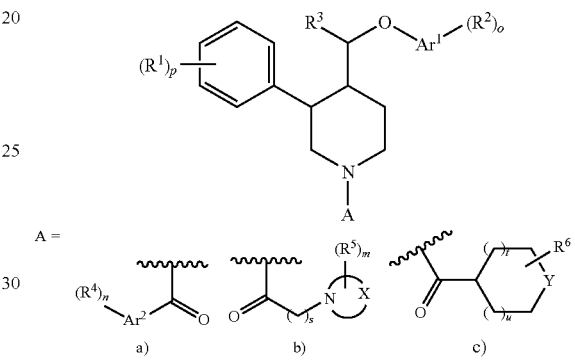

wherein $Ar^1$ is aryl or a five or six-membered heteroaryl;

$Ar^2$ is aryl or a five or six-membered heteroaryl;

$R^1$ is hydrogen, halogen, lower alkyl, lower alkyl substituted by halogen or cyano;

$R^2$ is hydrogen, halogen, cyano, lower alkyl, or lower alkyl substituted by halogen;

$R^3$ is hydrogen, lower alkyl or $CH_2OH$;

$R^4$ is hydrogen, halogen, lower alkyl, lower alkoxy, lower alkyl substituted by halogen, lower alkoxy substituted by halogen, S-lower alkyl, —S(O)$_2$-lower alkyl, —S(O)$_2$-di-lower alkyl amino, —(CH$_2$)$_q$R, cyano, amino, mono or di-lower alkyl amino, NHC(O)-lower alkyl, cycloalkyl or is a five-membered heteroaryl optionally substituted by lower alkyl; wherein R is cyano, di-lower alkyl amino or pyrrolidin-1-yl;

is a six- to nine-membered mono or bi-heterocyclic group, wherein X is selected from a carbon atom, SO$_2$ and a further hetero atom, selected from the group consisting of N and O;

if X is a carbon atom, O, SO$_2$ or unsubstituted N, then $R^5$ is hydrogen, hydroxy, cyano, —(CH$_2$)$_q$—OH, —(CH$_2$)$_q$—NRR', —(CH$_2$)$_q$—CN, lower alkyl, —S(O)$_2$-lower alkyl, —NR—S(O)$_2$-lower alkyl, —C(O)-lower alkyl, —NR—C(O)-lower alkyl, phenyl, or is a heterocyclic group selected from piperidinyl-2-one;

if X is a N-atom, substituted by $R^5$, then $R^5$ is hydrogen, —$(CH_2)_q$—OH, —$(CH_2)_q$—NRR', —$(CH_2)_q$—CN, lower alkyl, —$S(O)_2$-lower alkyl, aryl or a five- or six-membered heteroaryl or —C(O)-lower alkyl, provided that q is 2 or 3.

R and R' are each independently hydrogen or lower alkyl;

$R^6$ is hydrogen, lower alkyl or hydroxy;

Y is —$CH(R^7)$—, —$N(R^{7'})$— or —O—

$R^7$ is hydrogen, hydroxy, =O, lower alkyl, —$S(O)_2$-lower alkyl, —C(O)-lower alkyl, —$C(O)CH_2O$-lower alkyl, —$CH_2CN$, —$C(O)CH_2CN$, —C(O)-cycloalkyl wherein the cycloalkyl group is optionally substituted by cyano, lower alkyl, one or two halogen atoms, =O or by amino, or is —C(O)O-lower alkyl, —NH-lower alkyl, —$NR^8C(O)$O-lower alkyl, —$NR^8C(O)$-lower alkyl or —$CH_2O$-lower alkyl; and $R^{7'}$ is hydrogen, lower alkyl, —$S(O)_2$-lower alkyl, —C(O)-lower alkyl, —$C(O)CH_2$—O-lower alkyl, —$CH_2CN$, —C(O)CN, —$C(O)CH_2CN$, or C(O)-cycloalkyl, wherein the cycloalkyl group is optionally substituted by cyano, lower alkyl, one or two halogen atoms, =O or by amino, or is —C(O)O-lower alkyl or —$CH_2O$-lower alkyl;

$R^8$ is hydrogen or lower alkyl; or $R^6$ and $R^7$ together with the carbon atoms to which they are attached form a five or six-membered non aromatic ring or $R^6$ and $R^{7'}$ together with the nitrogen and carbon atoms to which they are attached form a five- or six-membered non aromatic ring;

n is 1, 2 or 3; wherein when n is 2 or 3, each $R^4$ is the same or different;

m is 1 or 2; wherein when m is 2, each $R^5$ is the same or different;

o is 1, 2 or 3; wherein when o is 2 or 3, each $R^2$ is the same or different;

p is 1, 2 or 3; wherein when p is 2 or 3, each $R^1$ is the same or different;

q is 1, 2 or 3;

s is 0, 1, 2, 3 or 4 t is 0 or 1, or is 2 when u is 0; and u is 0 or 1 when t is 1;

or a pharmaceutically active salt, a racemic mixture, an enantiomer, an optical isomer or a tautomeric form thereof.

The present compounds of formula I and their pharmaceutically acceptable salts can be prepared by methods, known in the art, for example by the process variant described below, which process comprises a) coupling a compound of formula

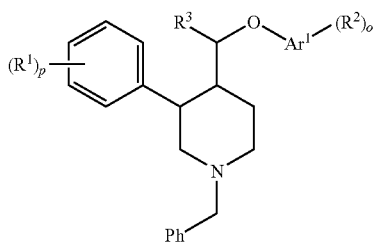

VIII with a corresponding compound of formula A-Hal to obtain a compound of formula

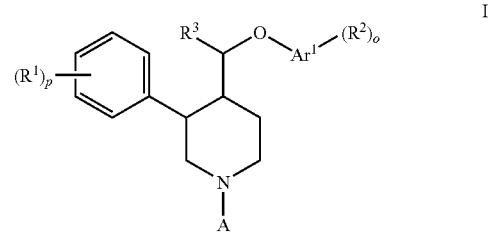

I wherein Hal is Cl, Br or I and the other definitions are as described above, and, if desired, converting the compound obtained into a pharmaceutically acceptable acid addition salt.

General Synthetic Scheme

The preparation of compounds of formula I of the present invention can be carried out in sequential or convergent synthetic routes. Syntheses of the compounds of the invention are shown in the following scheme. The skills required for carrying out the reaction and purification of the resulting products are known to those skilled in the art. The substituents and indices used in the following description of the processes have the significance given herein before unless indicated to the contrary.

In more detail, the compounds of formula I can be manufactured by the methods given below, by the methods given in the examples or by analogous methods given above. Appropriate reaction conditions for the individual reaction steps are known to a person skilled in the art. Also, for reaction conditions described in literature affecting the described reactions see for example: *Comprehensive Organic Transformations: A Guide to Functional Group Preparations,* 2nd Edition, Richard C. Larock. John Wiley & Sons, New York, N.Y. 1999). The described reactions can take place over a wide range of temperatures, and the precise reaction temperature is not critical to the invention. It is convenient to carry out the described reactions in a temperature range between −78° C. to reflux. The time required for the reaction can also vary widely, depending on many factors, notably the reaction temperature and the nature of the reagents. However, a period of from 0.5 h to several days will usually suffice to yield the described intermediates and compounds. The reaction sequence is not limited to the one displayed in scheme 1; however, depending on the starting materials and their respective reactivity, the sequence of reaction steps can be freely altered. Starting materials are either commercially available or can be prepared by methods analogous to the methods given below, by methods described in references cited in the description or in the examples, or by methods known in the art.

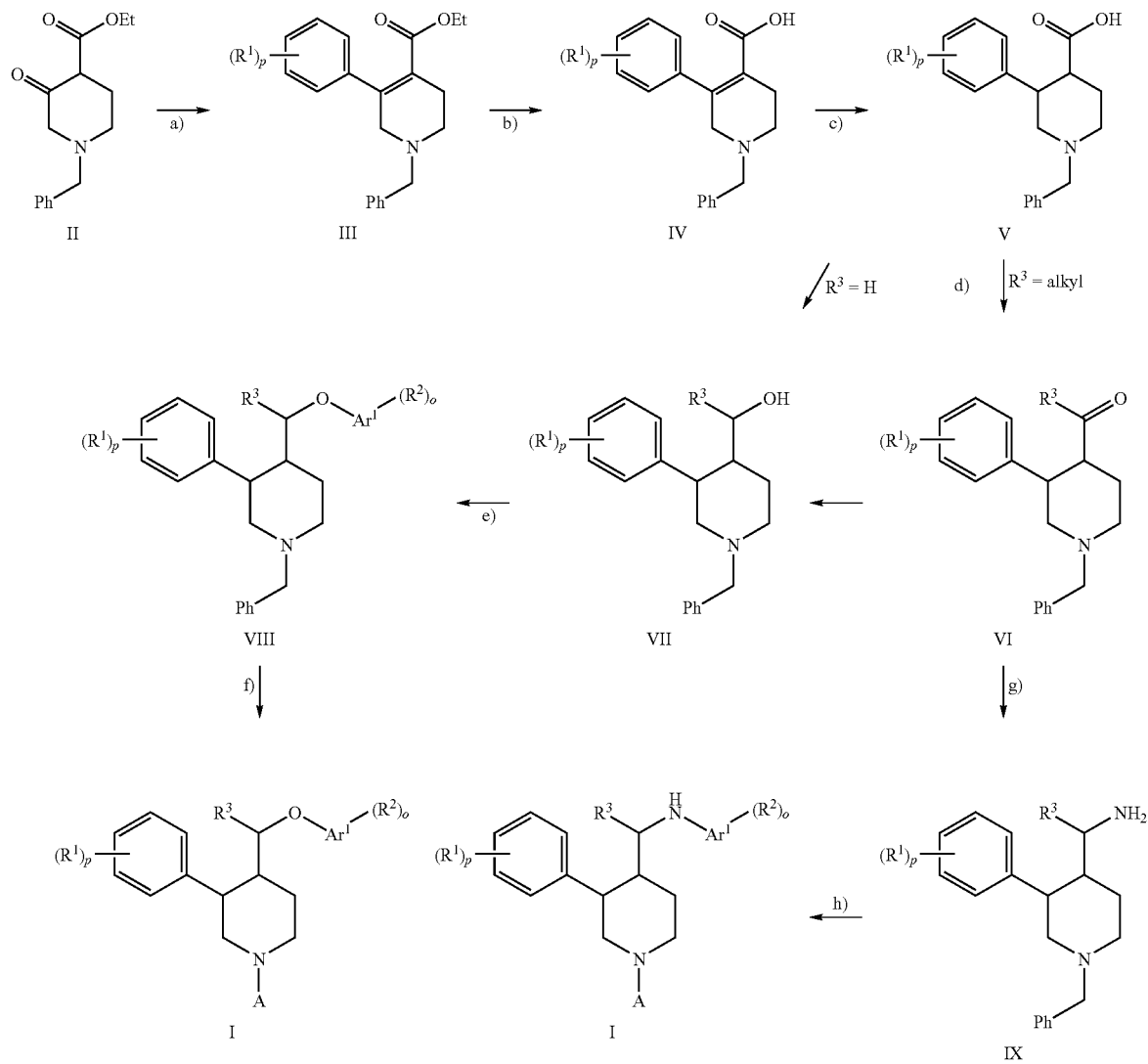

Scheme 1 a) It is convenient to react keto-ester II under basic conditions with triflic anhydride and subsequently under Palladium catalysis with boronic acid to access derivatives III.

b) The ester functionality in III is cleaved under basic aqueous conditions to access acid derivatives IV.

c) Reduction of the double bond in IV to access V can be done under various conditions with several metal catalysts and hydrogen under varying pressure. Chirality can be induced at this step.

d) Introduction of $R_3$ at this stage can be done in several ways. For $R_3$=H it is convenient to transform V to an intermediately built ester which optionally can be epimerized under basic conditions and subsequently reduced to the corresponding alcohol VII. In case $R_3$=alkyl acid V can optionally be transformed to the respective Weinreb amide which can be reacted with alkyl-Grignard reagents to access ketone VI, which can optionally be epimerized at this stage. The resulting ketone can be reduced to the corresponding alcohol VII.

e) Alcohol VII can be transformed to ether derivatives VIII in various ways. We find it convenient to perform a nucleophilc substitution reaction or a Mitsunobu reaction.

f) The transformation of derivatives VIII can be done by removal of the N-benzyl group under various ways and subsequent coupling with the appropriate A-X under various conditions to access the final compounds I.

g) Conversion of the ketone functionality in VI to access amine IX can be done under various conditions, however, we find it convenient to prepare the respective oxime from VI and subsequently reduce it.

h) Amine IX can conveniently be coupled with aromatic electrophiles to introduce $Ar^1(R^2)o$. Subsequently, transformation of these derivatives can be done by removal of the N-benzyl group under various ways and subsequent coupling with the appropriate A-X under various conditions to access the final compounds I.

Example 1

[(3RS,4RS)-3-(4-Chloro-phenyl)-4-(5-chloro-pyridin-2-yloxymethyl)-piperidin-1-yl]-[4-(3-methyl-[1,2,4]oxadiazol-5-yl)-phenyl]-methanone

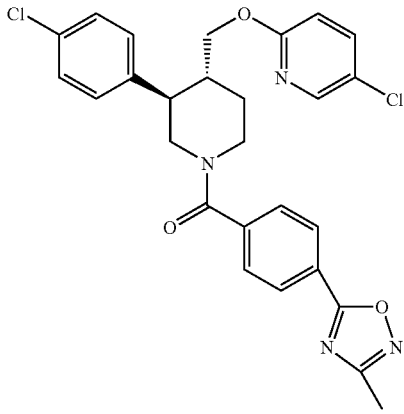

a) 1-Benzyl-5-(4-chloro-phenyl)-1,2,3,6-tetrahydropyridine-4-carboxylic acid ethyl ester

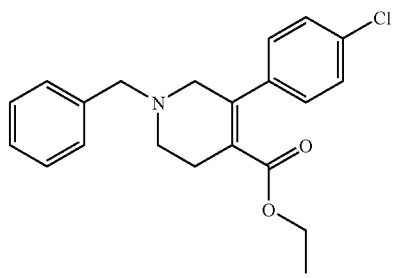

In a 1500 mL four necked flask (with mechanical stirrer) 22 g (84.2 mmol) ethyl N-benzyl-3-oxo-4-piperidine-carboxylate (from the HCl-salt by aq.Na$_2$CO$_3$/CH$_2$Cl$_2$-extraction) and 43.5 mL (252 mmol) DIPEA were dissolved in 300 mL DCM. The amber solution was cooled to −20° C. to −30° C. 28.5 g (101 mmol) trifluoromethanesulfonic anhydride were added drop wise over a period of 45 min. The dark brown solution was stirred for 2 h at −20° C./−30° C. 300 mL water and 300 mL 10% Na$_2$CO$_3$ aq. was added and the mixture was stirred for 15 min at 5-10° C. The organic layer was separated and the aqueous layer was extracted twice with 150 mL DCM. The combined organic layers were dried over Na$_2$SO$_4$ and filtered. The filtrate was evaporated to dryness and dissolved in 500 mL dioxane. 15.8 g (101 mmol) 4-chlorophenylboronic acid, 93 mL Na$_2$CO$_3$ aq. (2M) and 3.8 g (3.36 mmol) tetrakis(triphenylphosphine)palladium(0) was added and the mixture was heated to reflux over night. After cooling to room temperature, the mixture was diluted with 400 g ice-water and extracted twice with 400 mL ethyl acetate. The organic layers were extracted once with 500 mL brine. After drying over Na$_2$SO$_4$ the filtrate was evaporated to dryness. The black oil was absorbed on 60 g isolute HM-N and purified by column chromatography to yield 14.6 g (48%) of the title compound as viscous yellow oil. MS (m/e): 356.3 [(M+H)$^+$].

b) 1-Benzyl-5-(4-chloro-phenyl)-1,2,3,6-tetrahydropyridine-4-carboxylic acid

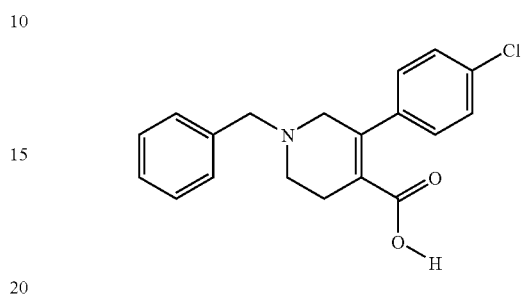

A mixture of 0.555 g (1.26 mmol) 1-benzyl-5-(4-chlorophenyl)-1,2,3,6-tetrahydro-pyridine-4-carboxylic acid ethyl ester and 261 mg (6.2 mmol) LiOH.H$_2$O in 15 mL THF and 5 mL water was stirred at room temperature over night. The mixture was evaporated to dryness, taken up in ethyl acetate, acidified with HCl to pH=1 and extracted with ethyl acetate. The combined organic layers were washed with water, evaporated to dryness and the residue was subjected to preparative HPLC chromatography on reversed phase eluting with a gradient formed from acetonitrile, water and formic acid to yield after evaporation of the product containing fractions 0.254 g (50%) of the title compound as white solid. MS (m/e): 328.2 [(M+H)$^+$].

c) (3RS, 4SR)-1-Benzyl-3-(4-chloro-phenyl)-piperidine-4-carboxylic acid

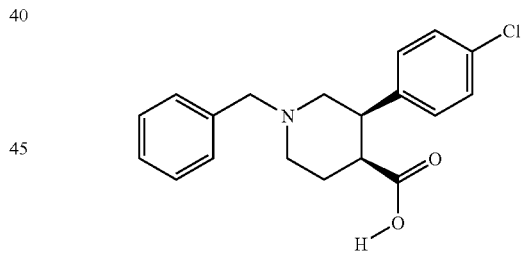

A 185-mL stainless steel autoclave was charged under argon in a glove box (O$_2$ content<2 ppm) with the hydrochloride salt of 1-benzyl-5-(4-chloro-phenyl)-1,2,3,6-tetrahydropyridine-4-carboxylic acid (7.00 g, 21.36 mmol), [Ru(OAc)$_2$((R)-(6,6'-dimethoxybiphenyl-2,2'-diyl)bis(di-2-furylphosphine)] (81.30 mg, 0.11 mol), [Ru(OAc)$_2$((S)-(6,6'-dimethoxybiphenyl-2,2'-diyl)bis(di-2-furylphosphine)] (81.30 mg, 0.11 mol), triethylamine (3.00 mL, 21.42 mmol) and methanol (120 mL). The hydrogenation was run for 20 h at 30° C. under 40 bar of hydrogen. After the pressure was released, the white suspension was evaporated to dryness to yield 9.58 g of the crude title compound. The crude product was dissolved in 1 M NaOH (45 mL). TBME (50 mL) was added, the aqueous layer was separated and diluted with water (250 mL). Under stirring 2 M HCl (20.5 mL) was added (pH value=6.0). The formed precipitate was filtered off and washed with water (50 mL). The filter cake was dissolved in methanol (100 mL) and the colorless solution evaporated to dryness to yield 5.13 g (70%) of the title compound. MS (m/e): 330.2 [(M+H)+].

d) (3RS, 4SR)-1-benzyl-3-(4-chloro-phenyl)-piperidine-4-carboxylic acid methyl ester

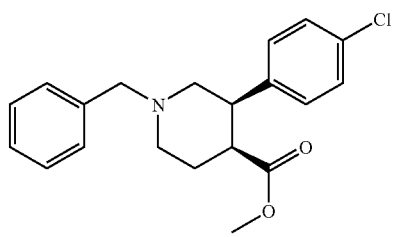

In a 500 ml round bottom flask with a magnetic stirring bar 3 g (9 mmol) (3RS, 4SR)-1-benzyl-3-(4-chloro-phenyl)-piperidine-4-carboxylic acid (SM050/4A) were suspended in 100 ml methanol. 50 mL 1.25 N HCl/MeOH was added and the mixture was stirred over night at reflux (76° C.). Another 50 mL 1.25 N HCl/MeOH was added and the reaction mixture was continued to reflux for 24 h. The solvent was removed by evaporation and the brown residue was diluted with 200 mL Na₂CO₃ aq. sat. and 5 mL 4 N NaOH aq. The mixture was extracted with 3 portions of 200 mL ethyl acetate. The combined organic layers were washed with 150 mL brine, dried over Na₂SO₄, filtered and evaporated. The residue was purified by column chromatography on silica eluting with ethyl acetate/heptane to yield after evaporation of the product containing fractions 2.74 g (88%) of the title compound as light yellow viscous oil. MS (m/e): 344.2 [(M+H)+].

e) (3RS, 4RS)-1-benzyl-3-(4-chloro-phenyl)-piperidine-4-carboxylic acid methyl ester

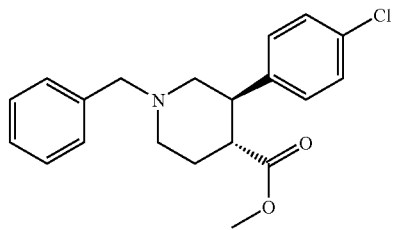

In a 250 ml round bottom flask under N₂ atmosphere and with a magnetic stirring bar, 1.5 g (4.3 mmol) ((3RS, 4SR)-1-benzyl-3-(4-chloro-phenyl)-piperidine-4-carboxylic acid methyl ester were dissolved in 50 mL methanol and 0.7 mL NaOMe (5.4M in MeOH) was added. The solution was stirred for 4 h at reflux. Another 1 mL NaOMe (5.4 M in MeOH) was added and refluxing was continued for 1 day. The solvent was evaporated and the residue dissolved in 40 mL water. The pH was adjusted to pH=12 with NaOH and the mixture was extracted with 2 portions of 50 mL ethyl acetate. The combined organic layers were washed with 30 mL brine, dried over Na₂SO₄, filtrated and evaporated to obtain 1.388 g (92%) of the title compound. MS (m/e): 344.3 [(M+H)+].

f) [3RS,4RS)-1-benzyl-3-(4-chloro-phenyl)-piperidin-4-yl]-methanol

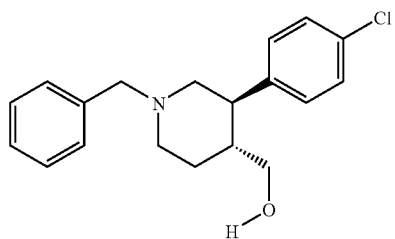

In a three necked 150 mL flushed round bottom flask under N₂ atmosphere and with a magnetic stirring bar, 1.388 g (4 mmol) (3RS, 4RS)-1-benzyl-3-(4-chloro-phenyl)-piperidine-4-carboxylic acid methyl ester were dissolved in 30 mL THF and at −5° C. five portions of 32 mg of LiAlH₄ was added. The reaction was stirred at 0° C. for 1 h and allowed to warm at room temperature during 1 h. The light green solution was cooled to 0° C. and 50 mL water and 15 mL Na₂CO₃ aq. sat. was added drop wise. After 15 min the solution was warmed to room temperature and extracted with two portions of 75 mL ethyl acetate. The combined organic layers were washed with 30 mL of a brine, dried over Na₂SO₄, filtered and evaporated. The viscous oil obtained was filtered over silica eluting with ethyl acetate/heptane. 1.23 g (96%) of the title compound was obtained as colorless viscous oil. MS (m/e): 316.1 [(M+H)+].

g) 2-[(3RS, 4RS)-1-benzyl-3-(4-chloro-phenyl)-piperidin-4-ylmethoxy]-5-chloro-pyridine

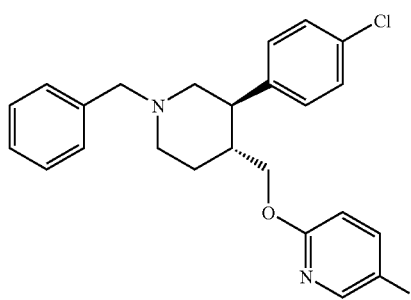

In a 100 mL four necked round bottom flask with a magnetic stirrer and inert atmosphere 1.3 g polymer bound triphenylphosphine was stirred in 15 mL THF. At 0-5° C. a solution of 514 mg (2.23 mmol) di-tert-butyl azodicarboxylate in 8 mL THF and a solution of 271 mg (2.1 mmol) 5-chloro-2-hydroxypyridine in 10 mL THF was added. The mixture was stirred for 20 min at 0° C.-5° C. 441 mg (1.4 mmol) [(3RS, 4RS)-1-benzyl-3-(4-chloro-phenyl)-piperidin-4-yl]-methanol in 8 mL THF was added. The ice bath was removed and the brownish mixture was stirred for 2 h at room temperature. The mixture was filtrated over decalite and washed with ethyl acetate. The solvents were evaporated and the residue purified by column chromatography on silica gel eluting with ethyl acetate/toluene to yield after evaporation of the product containing fractions 0.3 g (50%) of the title compounds as white solid. MS (m/e): 298.3/427.1 [(M+H)+].

h) 5-Chloro-2-[(3RS, 4RS)-3-(4-chloro-phenyl)-piperidin-4-ylmethoxy]-pyridine; hydrochloride

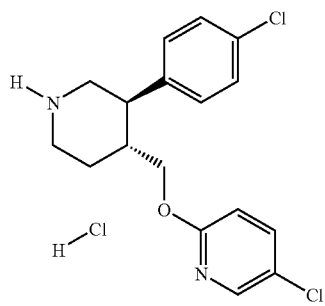

In a 10 mL round bottom flask with a magnetic stirring bar and under N$_2$ atmosphere, 60 mg (0.14 mmol) 2-[(3RS, 4RS)-1-benzyl-3-(4-chloro-phenyl)-piperidin-4-ylmethoxy]-5-chloro-pyridine were dissolved in 1 mL toluene. 23 uL 1-chloroethyl-chloroformate and 31 uL DIPEA was added. The solution was stirred at room temperature for 4 h. The solvent was removed under high vacuum and the residue dissolved in 1 mL methanol and stirred for 2 h at room temperature. The solvent was evaporated and the residue was purified over silica eluting with DCM/methanol/NH$_3$(2N) to yield after evaporation of the product containing fractions 35 mg (67%) of the title compound as colorless viscous oil. MS (m/e): 208.0/337.1 [(M+H)+].

i) [(3RS, 4RS)-3-(4-Chloro-phenyl)-4-(5-chloro-pyridin-2-yloxymethyl)-piperidin-1-yl]-[4-(3-methyl-[1,2,4]oxadiazol-5-yl)-phenyl]-methanone

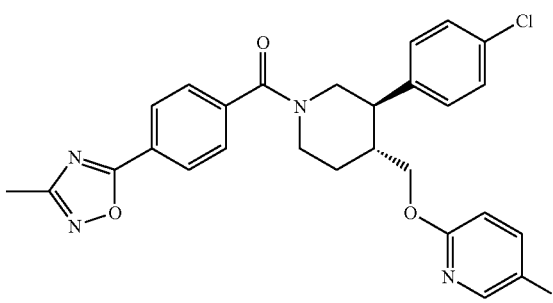

A mixture of 18 mg (0.08 mmol) 4-(3-methyl-1,2,4-oxadiazol-5-yl)benzoic acid, 43 mg (0.11 mmol) HATU, 0.1 mL DIPEA and 32 mg (0.09 mmol) 5-chloro-2-[(3RS, 4RS)-3-(4-chloro-phenyl)-piperidin-4-ylmethoxy]-pyridine; hydrochloride in 2 mL DMF was reacted at room temperature over night. The mixture was subjected to preparative HPLC purification on reversed phase eluting with a gradient formed from acetonitrile, water and NEt$_3$ to yield after evaporation of the product containing fractions 32 mg (64%) of the title compound as white foam. MS (m/e): 523.3 [(M+H)+].

Example 2

[(3RS, 4RS)-3-(4-Chloro-phenyl)-4-(5-trifluoromethyl-pyridin-2-yloxymethyl)-piperidin-1-yl]-[4-(3-methyl-[1,2,4]oxadiazol-5-yl)-phenyl]-methanone

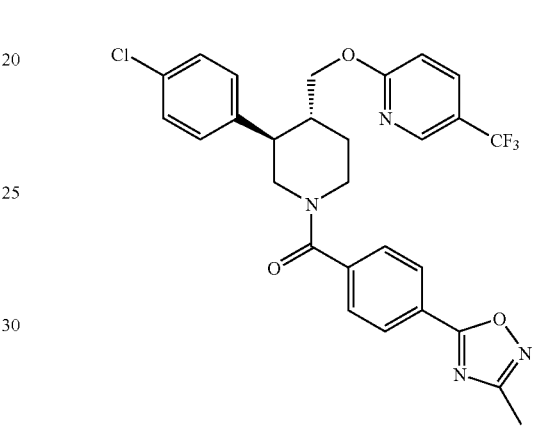

a) 2-[(3RS, 4RS)-1-benzyl-3-(4-chloro-phenyl)-piperidin-4-ylmethoxy]-5-trifluoromethyl-pyridine

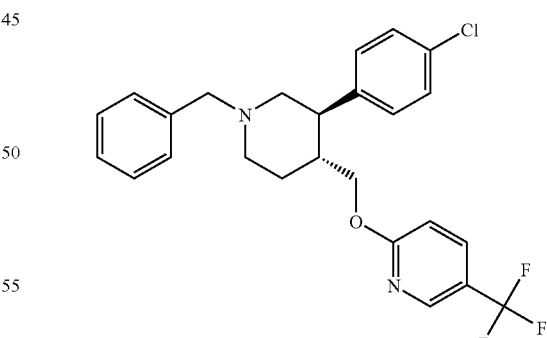

In analogy to the procedure described for the synthesis of 2-[(3RS, 4RS)-1-benzyl-3-(4-chloro-phenyl)-piperidin-4-ylmethoxy]-5-chloro-pyridine (example 1, step g) the title compound was prepared from [(3RS, 4RS)-1-benzyl-3-(4-chloro-phenyl)-piperidin-4-yl]-methanol and 5-trifluoromethyl-pyridin-2-ol (commercially available). MS (m/e): 298.3/461.2 [(M+H)+].

b) 2-[(3RS, 4RS)-3-(4-Chloro-phenyl)-piperidin-4-ylmethoxy]-5-trifluoromethyl-pyridine; hydrochloride

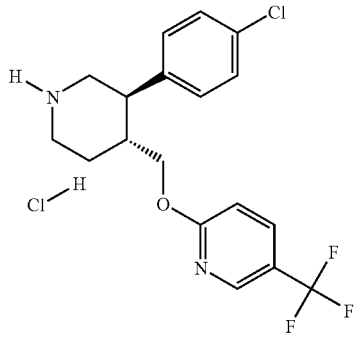

In analogy to the procedure described for the synthesis of 5-chloro-2-[(3RS, 4RS)-3-(4-chloro-phenyl)-piperidin-4-ylmethoxy]-pyridine; hydrochloride (example 1, step h) the title compound was prepared from 2-[(3RS, 4RS)-1-benzyl-3-(4-chloro-phenyl)-piperidin-4-ylmethoxy]-5-trifluoromethyl-pyridine as light yellow viscous oil. MS (m/e): 208.0/371.2 [(M+H)$^+$].

c) [(3RS, 4RS)-3-(4-Chloro-phenyl)-4-(5-trifluoromethyl-pyridin-2-yloxymethyl)-piperidin-1-yl]-[4-(3-methyl-[1,2,4]oxadiazol-5-yl)-phenyl]-methanone In analogy to the procedure described for the synthesis of [(3RS, 4RS)-3-(4-chloro-phenyl)-4-(5-chloro-pyridin-2-yloxymethyl)-piperidin-1-yl]-[4-(3-methyl-[1,2,4]oxadiazol-5-yl)-phenyl]-methanone (example 1, step i) the title compound was prepared from 2-[(3RS, 4RS)-3-(4-Chloro-phenyl)-piperidin-4-ylmethoxy]-5-trifluoromethyl-pyridine; hydrochloride and 4-(3-methyl-1,2,4-oxadiazol-5-yl)benzoic acid (commercially available) as colorless viscous oil. MS (m/e): 557.0 [(M+H)$^+$].

Example 3

{4-[(3RS, 4RS)-3-(4-Chloro-phenyl)-4-(5-trifluoromethyl-pyridin-2-yloxymethyl)-piperidine-1-carbonyl]-piperidin-1-yl}-(1-methyl-cyclopropyl)-methanone

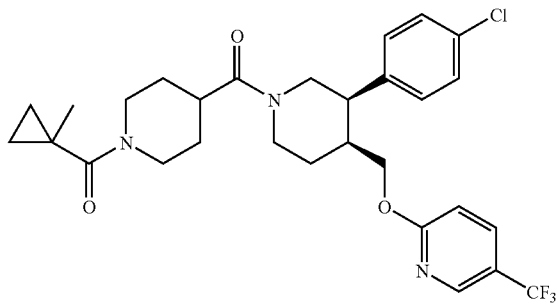

a) 1-(1-Methyl-cyclopropanecarbonyl)-piperidine-4-carboxylic acid ethyl ester

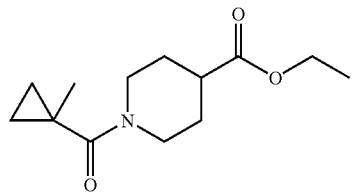

To a stirred solution of 14.4 g (0.144 mol) 1-methyl-cyclopropanecarboxylic acid in 200 mL DCM was added 27.1 g (0.141 mol) EDC, 19.10 g (0.141 g) HOBt and 35.93 mL (0.259 mol) Et$_3$N. After 1 h at room temperature 18.9 g (0.12 mol) piperidine-4-carboxylic acid ethyl ester was added and the mixture was stirred at room temperature over night. The mixture was poured onto water and extracted with DCM. The combined organic phases were dried over Na$_2$SO$_4$ and concentrated under vacuum. Column chromatography (SiO$_2$, EtOAc/H, 1:1) yielded 26.1 g (92%) of the title compound as a light yellow oil.

b) 1-(1-Methyl-cyclopropanecarbonyl)-piperidine-4-carboxylic acid

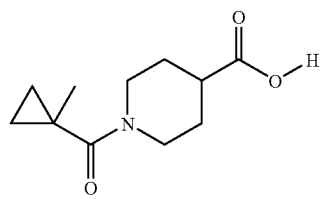

To a stirred solution of 26.09 g (0.109 mol) 1-(1-methyl-cyclopropanecarbonyl)-piperidine-4-carboxylic acid ethyl ester in 500 mL THF, EtOH, water (1/1/1) was added 6.86 g (0.163 mol) LiOH.H$_2$O. After 1 h at room temperature, the solvents were evaporated and the residue taken up in DCM and the organic phase was washed with aqueous HCl 1M. The organic phases were dried over Na$_2$SO$_4$ and evaporated under vacuum to give 19.8 g (86%) of the title compound as a white solid. MS (m/e): 212.1 [(M+H)$^+$].

c) {4-[(3RS 4RS)-3-(4-Chloro-phenyl)-4-(5-trifluoromethyl-pyridin-2-yloxymethyl-piperidine-1-carbonyl]-piperidin-1-yl}-(1-methyl-cyclopropyl)-methanone In analogy to the procedure described for the synthesis of [(3RS, 4RS)-3-(4-Chloro-phenyl)-4-(5-chloro-pyridin-2-yloxymethyl)-piperidin-1-yl]-[4-(3-methyl-[1,2,4]oxadiazol-5-yl)-phenyl]-methanone (example 1, step i) the title compound was prepared from 2-[(3RS, 4RS)-3-(4-Chloro-phenyl)-piperidin-4-ylmethoxy]-5-trifluoromethyl-pyridine;

hydrochloride and 1-(1-methyl-cyclopropanecarbonyl)-piperidine-4-carboxylic acid as white solid. MS (m/e): 564.3 [(M+H)⁺].

Example 4

{4-[(3RS, 4RS)-3-(4-Chloro-phenyl)-4-(5-chloro-pyridin-2-yloxymethyl)-piperidine-1-carbonyl]-piperidin-1-yl}-(1-methyl-cyclopropyl)-methanone

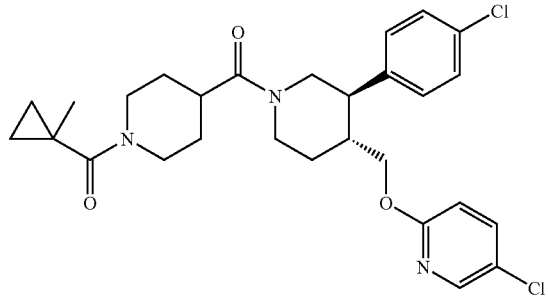

In analogy to the procedure described for the synthesis of [(3RS, 4RS)-3-(4-Chloro-phenyl)-4-(5-chloro-pyridin-2-yloxymethyl)-piperidin-1-yl]-[4-(3-methyl-[1,2,4]oxadiazol-5-yl)-phenyl]-methanone (example 1, step i) the title compound was prepared from 5-chloro-2-[(3RS, 4RS)-3-(4-chloro-phenyl)-piperidin-4-ylmethoxy]-pyridine; hydrochloride and 1-(1-methyl-cyclopropanecarbonyl)-piperidine-4-carboxylic acid as white solid. MS (m/e): 530.2 [(M+H)⁺].

Example 5

(4-{(3SR, 4SR)-3-(4-Chloro-phenyl)-4-[(SR)-1-(5-chloro-pyridin-2-yloxy)-ethyl]-piperidine-1-carbonyl}-piperidin-1-yl)-(1-methyl-cyclopropyl)-methanone

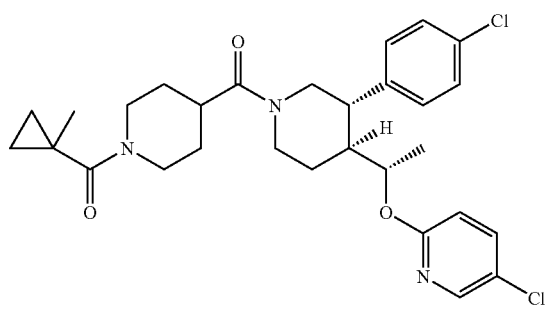

a) (3RS,4SR)-1-Benzyl-3-(4-chloro-phenyl)-piperidine-4-carboxylic acid methoxy-methyl-amide

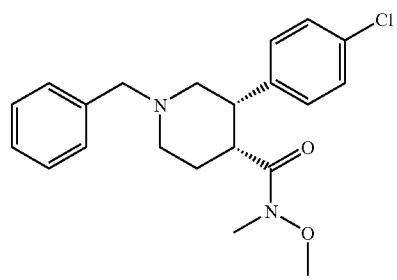

In a 100 mL round bottom flask with a magnetic stirrer 900 mg (2.72 mmol) (3RS,4SR)-1-benzyl-3-(4-chloro-phenyl)-piperidine-4-carboxylic acid and 1.14 g (3 mmol) HATU was dissolved in 20 mL dry DMF. The greenish solution was stirred for 15 min, 320 mg (3.28 mmol) N,O-dimethylhydroxylamine hydrochlorideowed and 2.32 mL DIPEA was added. The mixture was stirred for 3 h at room temperature and concentrated under high vacuum. The green viscous oil was taken up in 60 mL ethyl acetate and 75 mL 5% aqueous NaHCO₃-solution. The aqueous layer was separated and extracted once with 60 mL ethyl acetate. The combined organic layers were washed with 75 mL 1% AcOH/water-solution and once with 100 ml brine, dried over Na₂SO₄, filtered off and concentrated under vacuum. The residue was purified over silica eluting with a gradient formed from ethyl acetate/heptane to yield after evaporation of the product containing fractions 990 mg (97%) of the title compound as colorless viscous oil. MS (m/e): 373.3 [(M+H)⁺].

b) 1-[(3SR,4RS)-1-Benzyl-3-(4-chloro-phenyl)-piperidin-4-yl]-ethanone

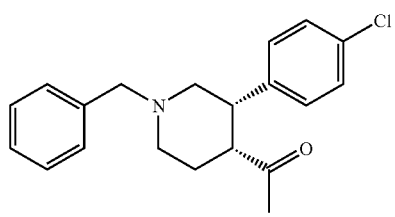

Under an inert atmosphere a 50 mL four necked flask (flame dried) with a magnetic stirrer was charged with 990 mg (2.65 mmol) (3SR,4RS)-1-benzyl-3-(4-chloro-phenyl)-piperidine-4-carboxylic acid methoxy-methyl-amide in 15 ml THF. The light yellow solution was cooled to −40° C. and 2.2 mL methylmagnesium bromide (3M in diethyl ether) was added drop wise over 5 min. The reaction was slowly warmed up to 0° C. over 2 h. The reaction mixture was quenched slowly with 20 mL aqueous NH₄Cl-solution, diluted with 10 mL water and 10 mL ethyl acetate. The aqueous layer was separated and extracted once with 30 mL ethyl acetate. The combined organic layers were washed with 50 mL brine, dried over Na₂SO₄, filtered off and concentrated under vacuum and used without further purification in the consecutive step. MS (m/e): 327.2 [(M+H)⁺].

c) 1-[(3SR,4RS)-1-Benzyl-3-(4-chloro-phenyl)-piperidin-4-yl]-ethanone

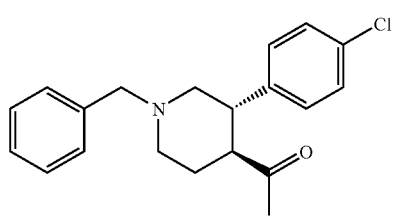

In analogy to the procedure described for the synthesis of (3RS, 4RS)-1-benzyl-3-(4-chloro-phenyl)-piperidine-4-carboxylic acid methyl ester (example 1, step e) the title compound was prepared from 1-[(3SR,4RS)-1-benzyl-3-(4- chloro-phenyl)-piperidin-4-yl]-ethanone through epimerisation with NaOMe. MS (m/e): 328.2/330.2 [(M+H)+].

d) (RS)-1-[(3SR,4SR)-1-Benzyl-3-(4-chloro-phenyl)-piperidin-4-yl]-ethanol

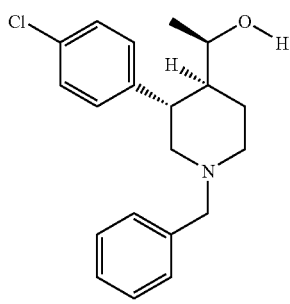

Under an inert atmosphere a 100 mL four necked flask (flame dried) with a magnetic stirrer was charged with 835 mg (2.54 mmol) 1-[(3SR,4SR)-1-benzyl-3-(4-chloro-phenyl)-piperidin-4-yl]-ethanone in 25 mL THF. The yellow solution was cooled to 0° C. and 34 mg (0.89 mmol) LiAlH₄ was added. The mixture was stirred for 30 min at 0° C. and 30 min from 0° C. to 15° C. At 0° C. 10 mL ethyl acetate was added drop-wise, followed by 5 mL THF:water 9:1 and 1 mL 4 N aqueous NaOH and 1 mL water. The mixture was stirred for 30 min at 40-50° C. and Na₂SO₄ was added. The mixture was filtered off and concentrated under vacuum. The residue was purified by chromatography on silica eluting with a gradient formed from DCM, methanol, NH₃aq. to yield after evaporation of the product containing fractions 466 mg (55%) of the title compound as off-white foam. MS (m/e): 330.1 [(M+H)+].

e) 2-{(SR)-1-[(3SR,4SR)-1-Benzyl-3-(4-chloro-phenyl)-piperidin-4-yl]-ethoxy}-5-chloro-pyridine

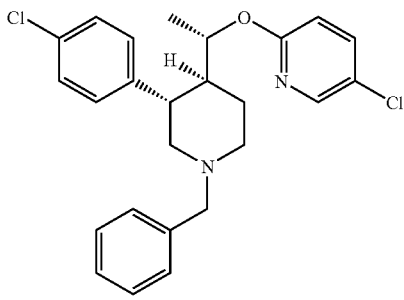

In a 50 mL three-necked round bottom flask (flame dried) charged with a magnetic stirrer and under inert atmosphere to 1080 mg polymer bound triphenylphosphine (3 mmol/g) in 10 mL THF was added 502 mg (2.18 mmol) di-tert-butyl azodicarboxylate in 5 mL THF and 265 mg (2.04 mmol) 5-chloro-2-hydroxypyridine in 10 mL THF at 0-5° C. The brownish suspension was stirred for 20 min at 0-5° C. 450 mg (1.36 mmol) (RS)-1-[(3SR,4SR)-1-benzyl-3-(4-chloro-phenyl)-piperidin-4-yl]-ethanol in 5 mL THF was added and the ice bath was removed and the reaction was stirred for 63 h at room temperature. The suspension was filtered over a Dicalit-filter. The filtrate was concentrated under vacuum and the residue was purified by chromatography over silica eluting with a gradient formed from i-propanol and heptane to yield after evaporation of the product containing fractions 480 mg (80%) of the title compound as yellow viscous oil. MS (m/e): 441.2 [(M+H)+].

f) 5-Chloro-2-{(SR)-1-[3SR,4SR)-3-(4-chloro-phenyl)-piperidin-4-yl]-ethoxy}-pyridine

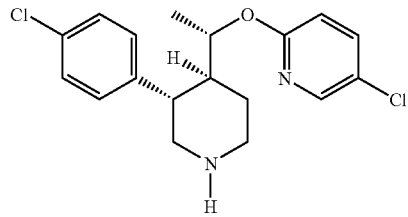

In analogy to the procedure described for the synthesis of 5-chloro-2-[(3RS, 4RS)-3-(4-chloro-phenyl)-piperidin-4-yl-methoxy]-pyridine; hydrochloride (example 1, step h) the title compound was prepared from 2-{(SR)-1-[(3SR,4SR)-1-benzyl-3-(4-chloro-phenyl)-piperidin-4-yl]-ethoxy}-5-chloro-pyridine as light yellow viscous oil. MS (m/e): 222.2/351.2 [(M+H)+].

g) (4-{(3SR, 4SR)-3-(4-Chloro-phenyl)-4-[(SR)-1-(5-chloro-pyridin-2-yloxy)-ethyl]-piperidine-1-carbonyl}-piperidin-1-yl)-(1-methyl-cyclopropyl)-methanone In analogy to the procedure described for the synthesis of [(3RS, 4RS)-3-(4-chloro-phenyl)-4-(5-chloro-pyridin-2-yloxymethyl)-piperidin-1-yl]-[4-(3-methyl-[1,2,4]oxadiazol-5-yl)-phenyl]-methanone (example 1, step i) the title compound was prepared from 5-chloro-2-{(SR)-1-[(3SR, 4SR)-3-(4-chloro-phenyl)-piperidin-4-yl]-ethoxy}-pyridine and 1-(1-methyl-cyclopropanecarbonyl)-piperidine-4-carboxylic acid as white solid. MS (m/e): 544.2 [(M+H)+].

Example 6

(4-{(3R,4R)-3-(4-Chloro-phenyl)-4-[(R)-1-(5-chloro-pyridin-2-yloxy)-ethyl]-piperidine-1-carbonyl}-piperidin-1-yl)-(1-methyl-cyclopropyl)-methanone

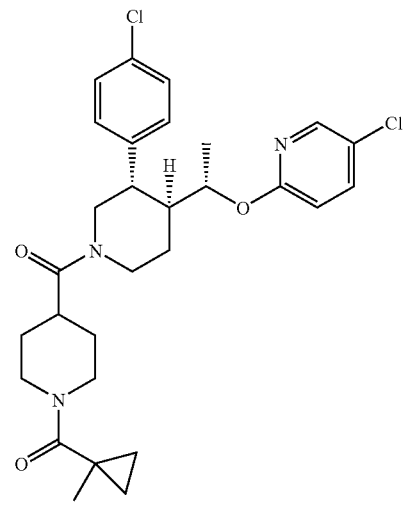

The title compound was assessed through chromatography on Chiralpak AD eluting with ethanol/heptane from (4-{(3SR, 4SR)-3-(4-chloro-phenyl)-4-[(SR)-1-(5-chloro-pyridin-2-yloxy)-ethyl]-piperidine-1-carbonyl}-piperidin-1-yl)-(1-methyl-cyclopropyl)-methanone (example 5) as off white foam. MS (m/e): 544.2 [(M+H)$^+$].

Example 7

(4-{(3S,4S)-3-(4-Chloro-phenyl)-4-[(S)-1-(5-chloro-pyridin-2-yloxy)-ethyl]-piperidine-1-carbonyl}-piperidin-1-yl)-(1-methyl-cyclopropyl)-methanone

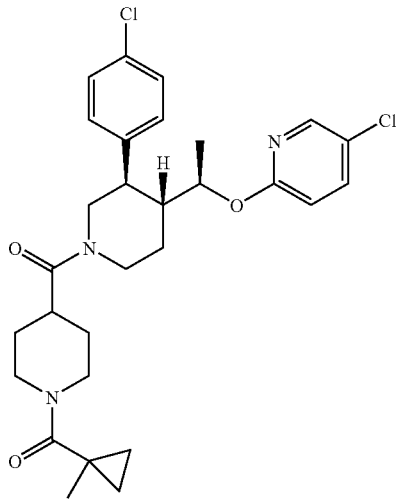

The title compound was assessed through chromatography on Chiralpak AD eluting with ethanol/heptane from (4-{(3SR, 4SR)-3-(4-chloro-phenyl)-4-[(SR)-1-(5-chloro-pyridin-2-yloxy)-ethyl]-piperidine-1-carbonyl}-piperidin-1-yl)-(1-methyl-cyclopropyl)-methanone (example 5) as light yellow foam. MS (m/e): 544.2 [(M+H)$^+$].

Example 8

(4-{(3S,4S)-3-(4-Chloro-phenyl)-4-[(R)-1-(5-chloro-pyridin-2-yloxy)-ethyl]-piperidine-1-carbonyl}-piperidin-1-yl)-(1-methyl-cyclopropyl)-methanone

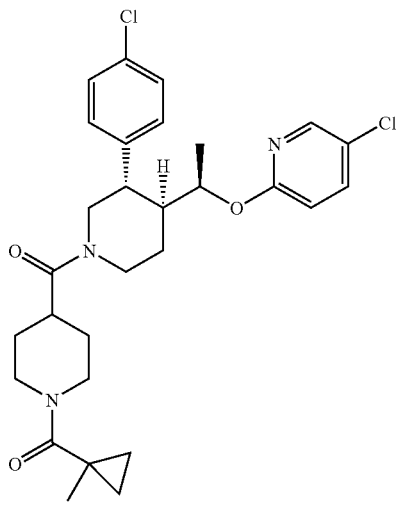

a) (3S,4R)-1-Benzyl-3-(4-chloro-phenyl)-piperidine-4-carboxylic acid

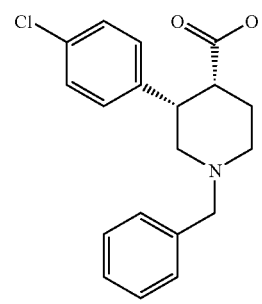

In analogy to the synthesis of (3RS, 4SR)-1-Benzyl-3-(4-chloro-phenyl)-piperidine-4-carboxylic acid (example 1 (c)) the title compound was prepared through hydrogenation of 1-benzyl-5-(4-chloro-phenyl)-1,2,3,6-tetrahydro-pyridine-4-carboxylic acid under Ruthenium catalysis ([Ru(OAc)$_2$((R)-(6,6'-dimethoxybiphenyl-2,2'-diyl)bis(di-2-furylphosphine)]). The title compound was used without further purification in the consecutive step.

b) (3S,4R)-1-Benzyl-3-(4-chloro-phenyl)-piperidine-4-carboxylic acid methoxy-methyl-amide

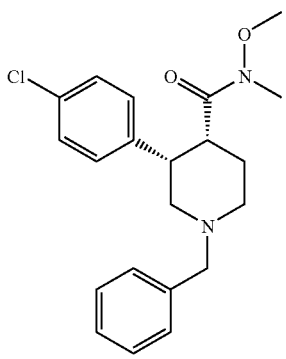

In analogy to the procedure described for the synthesis of (3RS,4SR)-1-Benzyl-3-(4-chloro-phenyl)-piperidine-4-carboxylic acid methoxy-methyl-amide (example 5 (a)) the title compound was prepared from (3S,4R)-1-Benzyl-3-(4-chloro-phenyl)-piperidine-4-carboxylic acid and methoxymethylamine. The title compound was obtained as brown viscous oil. MS (m/e): 373.2 [(M+H)$^+$].

c) 1-[(3S,4S)-1-Benzyl-3-(4-chloro-phenyl)-piperidin-4-yl]-ethanone

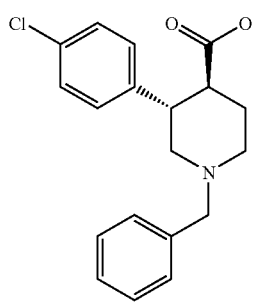

In analogy to the procedure described for the synthesis of 1-[(3SR,4SR)-1-benzyl-3-(4-chloro-phenyl)-piperidin-4-yl]-ethanone (example 5 (c)) the title compound was prepared from (3S,4R)-1-benzyl-3-(4-chloro-phenyl)-piperidine-4-carboxylic acid methoxy-methyl-amide and methylmagnesium bromide with subsequent epimerisation with NaOMe in methanol. The title compound was obtained as off-white solid. MS (m/e): 328.2 [(M+H)$^+$].

d) (R)-1-[(3S,4S)-1-Benzyl-3-(4-chloro-phenyl)-piperidin-4-yl]-ethanol and (S)-1-[(3S,4S)-1-benzyl-3-(4-chloro-phenyl)-piperidin-4-yl]-ethanol

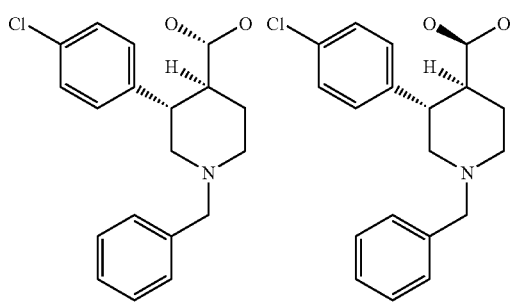

In analogy to the procedure described for the synthesis of (RS)-1-[(3SR,4SR)-1-Benzyl-3-(4-chloro-phenyl)-piperidin-4-yl]-ethanol (example 5 (d)) the title compounds were synthesized from 1-[(3S,4S)-1-Benzyl-3-(4-chloro-phenyl)-piperidin-4-yl]-ethanone through reduction with LiAlH$_4$. (R)-1-[(3S,4S)-1-Benzyl-3-(4-chloro-phenyl)-piperidin-4-yl]-ethanol was obtained as light yellow viscous oil. MS (m/e): 330.1 [(M+H)$^+$] and (S)-1-[(3S,4S)-1-Benzyl-3-(4-chloro-phenyl)-piperidin-4-yl]-ethanol was obtained as colorless foam. MS (m/e): 330.1 [(M+H)$^+$]

e) 2-{(R)-1-[(3S,4S)-1-Benzyl-3-(4-chloro-phenyl)-piperidin-4-yl]-ethoxy}-5-chloro-pyridine

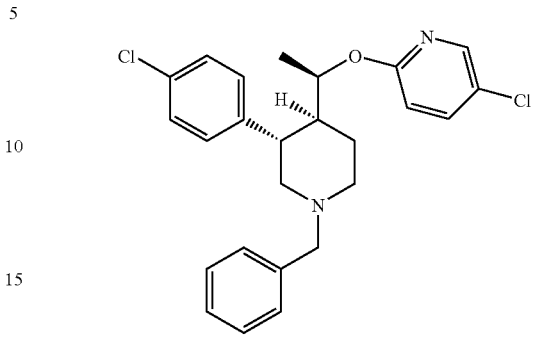

A mixture of 69 mg (1.7 mmol) NaH (55% suspension in mineral oil), 359 mg (1.08 mmol) (S)-1-[(3S,4S)-1-benzyl-3-(4-chloro-phenyl)-piperidin-4-yl]-ethanol and 225 mg (1.52 mmol) 2,5-dichloropyridine in 2 mL DMF was stirred for 20 h at 40° C. Further 0.2 eq. 2,5-dichloropyridine was added and stirring was continued for 20 h at 60° C. After evaporation the residue was purified by column chromatography on silica eluting with a gradient formed from ethyl acetate and heptane to afford after evaporation of the product containing fractions 205 mg (43%) of the title compound as colorless viscous oil. MS (m/e): 441.1 [(M+H)$^+$]

f) 5-Chloro-2-{(R)-1-[(3S,4S)-3-(4-chloro-phenyl)-piperidin-4-yl]-ethoxy}-pyridine

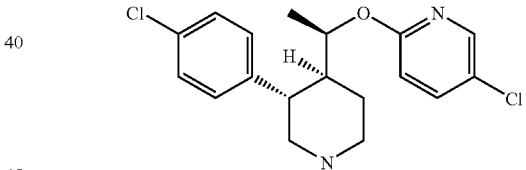

In analogy to the procedure described for the synthesis of 5-chloro-2-[(3RS, 4RS)-3-(4-chloro-phenyl)-piperidin-4-yl-methoxy]-pyridine; hydrochloride (example 1, step h) the title compound was prepared from 2-{(R)-1-[(3S,4S)-1-Benzyl-3-(4-chloro-phenyl)-piperidin-4-yl]-ethoxy}-5-chloro-pyridine as yellow oil. MS (m/e): 351.2 [(M+H)$^+$].

(4-{(3S,4S)-3-(4-Chloro-phenyl)-4-[(R)-1-(5-chloro-pyridin-2-yloxy)-ethyl]-piperidine-1-carbonyl}-piperidin-1-yl)-(1-methyl-cyclopropyl)-methanone In analogy to the procedure described for the synthesis of [(3RS,4RS)-3-(4-chloro-phenyl)-4-(5-chloro-pyridin-2-yloxymethyl)-piperidin-1-yl]-[4-(3-methyl-[1,2,4]oxadiazol-5-yl)-phenyl]-methanone (example 1, step i) the title compound was prepared from 5-Chloro-2-{(R)-1-[(3S,4S)-3-(4-chloro-phenyl)-piperidin-4-yl]-ethoxy}-pyridine and 1-(1-methyl-cyclopropanecarbonyl)-piperidine-4-carboxylic acid as white foam. MS (m/e): 544.2 [(M+H)$^+$].

Example 9

(4-{(3R,4R)-3-(4-Chloro-phenyl)-4-[(S)-1-(5-chloro-pyridin-2-yloxy)-ethyl]-piperidine-1-carbonyl}-piperidin-1-yl)-(1-methyl-cyclopropyl)-methanone

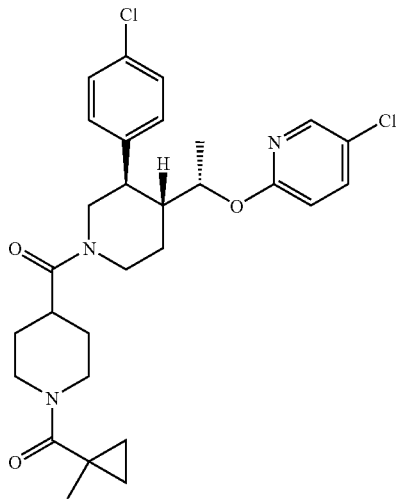

a) (3R,4S)-1-Benzyl-3-(4-chloro-phenyl)-piperidine-4-carboxylic acid

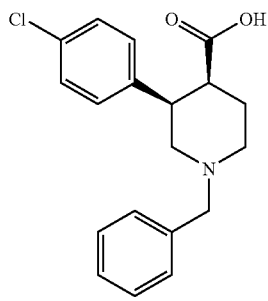

In analogy to the synthesis of (3RS, 4SR)-1-Benzyl-3-(4-chloro-phenyl)-piperidine-4-carboxylic acid (example 1 (c)) the title compound was prepared through hydrogenation of 1-benzyl-5-(4-chloro-phenyl)-1,2,3,6-tetrahydro-pyridine-4-carboxylic acid under Ruthenium catalysis ([Ru(OAc)$_2$ ((S)-(6,6'-dimethoxybiphenyl-2,2'-diyl)bis(di-2-furylphosphine)]). The title compound was used without further purification in the consecutive step.

b) (3R,4S)-1-Benzyl-3-(4-chloro-phenyl)-piperidine-4-carboxylic acid methoxy-methyl-amide

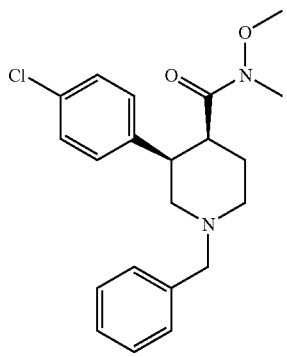

In analogy to the procedure described for the synthesis of (3RS,4SR)-1-Benzyl-3-(4-chloro-phenyl)-piperidine-4-carboxylic acid methoxy-methyl-amide (example 5 (a)) the title compound was prepared from (3R,4S)-1-Benzyl-3-(4-chloro-phenyl)-piperidine-4-carboxylic acid and methoxymethylamine. The title compound was obtained as yellow viscous oil. MS (m/e): 373.1 [(M+H)$^+$].

c) 1-[(3R,4R)-1-Benzyl-3-(4-chloro-phenyl)-piperidin-4-yl]-ethanone

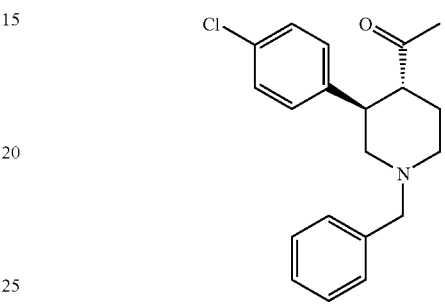

In analogy to the procedure described for the synthesis of 1-[(3SR,4SR)-1-benzyl-3-(4-chloro-phenyl)-piperidin-4-yl]-ethanone (example 5 (c)) the title compound was prepared from (3R,4S)-1-Benzyl-3-(4-chloro-phenyl)-piperidine-4-carboxylic acid methoxy-methyl-amide and methylmagnesium bromide with subsequent epimerisation with NaOMe in methanol. The title compound was obtained as off-white solid. MS (m/e): 327.1 [(M+H)$^+$].

d) (R)-1-[(3R,4R)-1-Benzyl-3-(4-chloro-phenyl)-piperidin-4-yl]-ethanol and (S)-1-[(3R,4R)-1-benzyl-3-(4-chloro-phenyl)-piperidin-4-yl]-ethanol

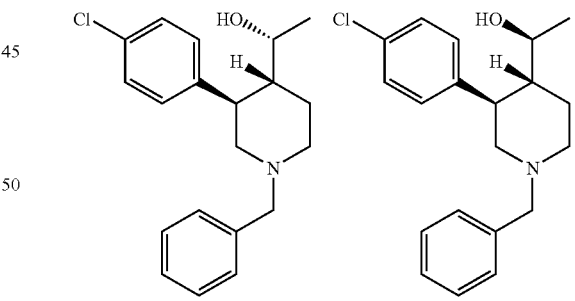

In analogy to the procedure described for the synthesis of (RS)-1-[(3SR,4SR)-1-Benzyl-3-(4-chloro-phenyl)-piperidin-4-yl]-ethanol (example 5 (d)) the title compounds were synthesized from 1-[(3R,4R)-1-Benzyl-3-(4-chloro-phenyl)-piperidin-4-yl]-ethanone through reduction with LiAlH$_4$. (R)-1-[(3R,4R)-1-Benzyl-3-(4-chloro-phenyl)-piperidin-4-yl]-ethanol was obtained as off-white solid. MS (m/e): 330.1 [(M+H)$^+$] and (S)-1-[(3R,4R)-1-Benzyl-3-(4-chloro-phenyl)-piperidin-4-yl]-ethanol was obtained as colorless viscous oil. MS (m/e): 330.1 [(M+H)$^+$]

e) 2-{(S)-1-[(3R,4R)-1-Benzyl-3-(4-chloro-phenyl)-piperidin-4-yl]-ethoxy}-5-chloro-pyridine

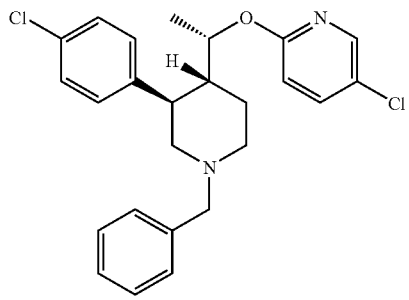

In analogy to the procedure described for the synthesis of 2-{(R)-1-[(3S,4S)-1-Benzyl-3-(4-chloro-phenyl)-piperidin-4-yl]-ethoxy}-5-chloro-pyridine the title compound was prepared from (S)-1-[(3R,4R)-1-Benzyl-3-(4-chloro-phenyl)-piperidin-4-yl]-ethanol and 2,5-dichloropyridine as colorless viscous oil. MS (m/e): 441.1 [(M+H)$^+$].

f) 5-Chloro-2-{(S)-1-[(3R,4R)-3-(4-chloro-phenyl)-piperidin-4-yl]-ethoxy}-pyridine

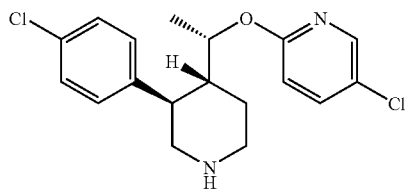

In analogy to the procedure described for the synthesis of 5-chloro-2-[(3RS, 4RS)-3-(4-chloro-phenyl)-piperidin-4-yl-methoxy]-pyridine; hydrochloride (example 1, step h) the title compound was prepared from 2-{(S)-1-[(3R,4R)-1-Benzyl-3-(4-chloro-phenyl)-piperidin-4-yl]-ethoxy}-5-chloro-pyridine as light yellow viscous oil. MS (m/e): 351.2 [(M+H)$^+$].

g) (4-{(3R,4R)-3-(4-Chloro-phenyl)-4-[(s)-1-(5-chloro-pyridin-2-yloxy)-ethyl]-piperidine-1-carbonyl}-piperidin-1-yl)-(1-methyl-cyclopropyl)-methanone In analogy to the procedure described for the synthesis of [(3RS, 4RS)-3-(4-chloro-phenyl)-4-(5-chloro-pyridin-2-yloxymethyl)-piperidin-1-yl]-[4-(3-methyl-[1,2,4]oxadiazol-5-yl)-phenyl]-methanone (example 1, step i) the title compound was prepared from 5-Chloro-2-{(S)-1-[(3R,4R)-3-(4-chloro-phenyl)-piperidin-4-yl]-ethoxy}-pyridine and 1-(1-methyl-cyclopropanecarbonyl)-piperidine-4-carboxylic acid as white foam. MS (m/e): 544.1 [(M+H)$^+$].

Example 10

{(3S,4S)-3-(4-Chloro-phenyl)-4-[(S)-1-(5-chloro-pyridin-2-yloxy)-ethyl]-piperidin-1-yl}-(6-methyl-pyridazin-4-yl)-methanone

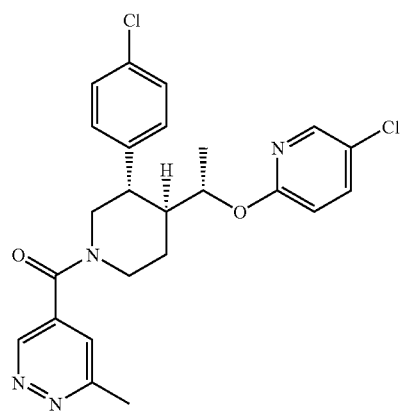

a) 2-{(S)-1-[3S,4S)-1-Benzyl-3-(4-chloro-phenyl)-piperidin-4-yl]-ethoxy}-5-chloro-pyridine

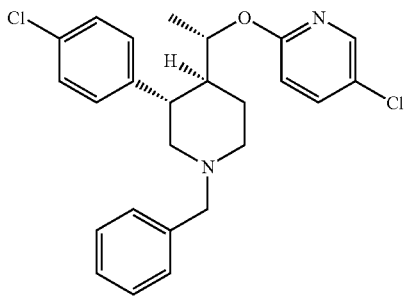

In analogy to the procedure described for the synthesis of 2-{(SR)-1-[(3SR,4SR)-1-Benzyl-3-(4-chloro-phenyl)-piperidin-4-yl]-ethoxy}-5-chloro-pyridine the title compound was prepared from (R)-1-[(3S,4S)-1-Benzyl-3-(4-chloro-phenyl)-piperidin-4-yl]-ethanol and 5-chloro-2-hydroxypyridine as viscous colorless oil. MS (m/e): 441.3 [(M+H)$^+$].

b) 5-Chloro-2-{(S)-1-[(3S,4S)-3-(4-chloro-phenyl)-piperidin-4-yl]-ethoxy}-pyridine

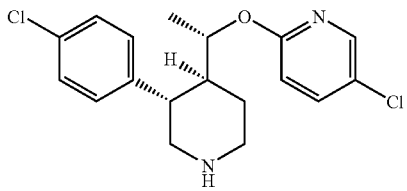

In analogy to the procedure described for the synthesis of 5-chloro-2-[(3RS, 4RS)-3-(4-chloro-phenyl)-piperidin-4-yl-methoxy]-pyridine; hydrochloride (example 1, step h) the title compound was prepared from 2-{(S)-1-[(3S,4S)-1-Benzyl-3-(4-chloro-phenyl)-piperidin-4-yl]-ethoxy}-5-chloro-pyridine as light brown foam as the respective HCl salt. MS (m/e): 351.2 [(M+H)⁺].

c) {(3S,4S)-3-(4-Chloro-phenyl)-4-[(S)-1-(5-chloro-pyridin-2-yloxy)-ethyl]-piperidin-1-yl}-(6-methyl-pyridazin-4-yl)-methanone In analogy to the procedure described for the synthesis of [(3RS,4RS)-3-(4-chloro-phenyl)-4-(5-chloro-pyridin-2-yloxymethyl)-piperidin-1-yl]-[4-(3-methyl-[1,2,4]oxadiazol-5-yl)-phenyl]-methanone (example 1, step i) the title compound was prepared from 5-Chloro-2-{(S)-1-[(3S,4S)-3-(4-chloro-phenyl)-piperidin-4-yl]-ethoxy}-pyridine and 6-Methyl-pyridazine-4-carboxylic acid (WO2009019163) as white solid. MS (m/e): 471.1 [(M+H)⁺].

Example 11

{(3S,4S)-3-(4-Chloro-phenyl)-4-[(S)-1-(5-chloro-pyridin-2-yloxy)-ethyl]-piperidin-1-yl}-[4-(3-methyl-[1,2,4]oxadiazol-5-yl)-phenyl]-methanone

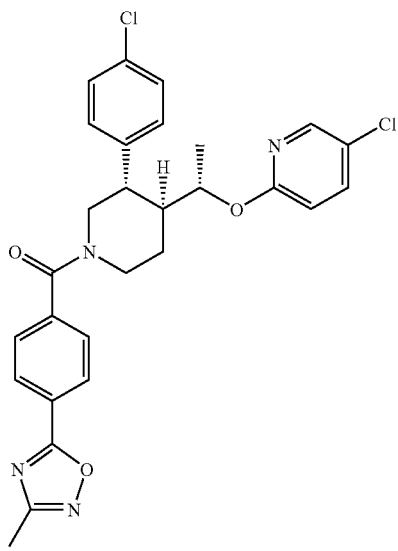

In analogy to the procedure described for the synthesis of [(3RS, 4RS)-3-(4-chloro-phenyl)-4-(5-chloro-pyridin-2-yloxymethyl)-piperidin-1-yl]-[4-(3-methyl-[1,2,4]oxadiazol-5-yl)-phenyl]-methanone (example 1, step i) the title compound was prepared from 5-Chloro-2-{(S)-1-[(3S,4S)-3-(4-chloro-phenyl)-piperidin-4-yl]-ethoxy}-pyridine and 4-(3-Methyl-[1,2,4]oxadiazol-5-yl)-benzoic acid (commercially available) as white solid. MS (m/e): 537.2 [(M+H)⁺].

Example 12

{(3S,4S)-3-(4-Chloro-phenyl)-4-[(S)-1-(5-chloro-pyridin-2-yloxy)-ethyl]-piperidin-1-yl}-[4-(5-methyl-[1,2,4]oxadiazol-3-yl)-phenyl]-methanone

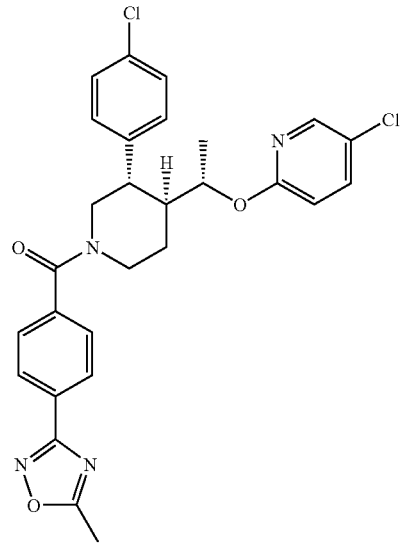

In analogy to the procedure described for the synthesis of [(3RS,4RS)-3-(4-chloro-phenyl)-4-(5-chloro-pyridin-2-yloxymethyl)-piperidin-1-yl]-[4-(3-methyl-[1,2,4]oxadiazol-5-yl)-phenyl]-methanone (example 1, step i) the title compound was prepared from 5-Chloro-2-{(S)-1-[(3S,4S)-3-(4-chloro-phenyl)-piperidin-4-yl]-ethoxy}-pyridine and 445-Methyl-[1,2,4]oxadiazol-3-yl)-benzoic acid (commercially available) as white solid. MS (m/e): 537.3 [(M+H)⁺].

Example 13

4-{(3S,4S)-3-(4-Chloro-phenyl)-4-[(S)-1-(5-chloro-pyridin-2-yloxy)-ethyl]-piperidine-1-carbonyl}-3,4,5,6-tetrahydro-2H-[1,2']bipyridinyl-5'-carbonitrile

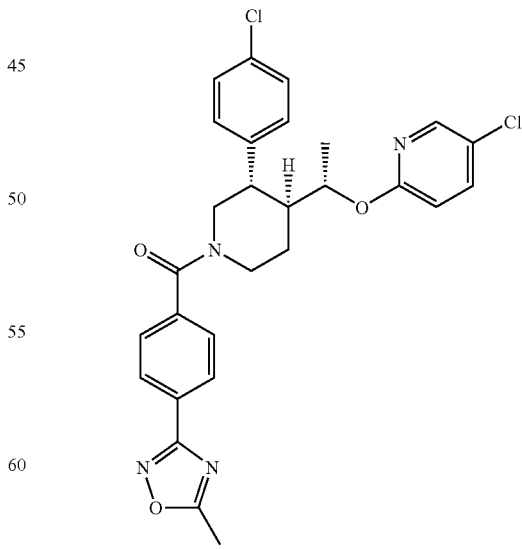

In analogy to the procedure described for the synthesis of [(3RS, 4RS)-3-(4-chloro-phenyl)-4-(5-chloro-pyridin-2-yloxymethyl)-piperidin-1-yl]-[4-(3-methyl-[1,2,4]oxadiazol-5-yl)-phenyl]-methanone (example 1, step i) the title compound was prepared from 5-Chloro-2-{(S)-1-[(3S,4S)-3-(4-chloro-phenyl)-piperidin-4-yl]-ethoxy}-pyridine and 5'-Cyano-3,4,5,6-tetrahydro-2H-[1,2']bipyridinyl-4-carboxylic acid (commercially available) as white solid. MS (m/e): 564.2 [(M+H)$^+$].

Example 14

{(3S,4S)-3-(4-Chloro-phenyl)-4-[(S)-1-(5-chloro-pyridin-2-yloxy)-ethyl]-piperidin-1-yl}-(4-methane-sulfonyl-piperazin-1-yl)-methanone

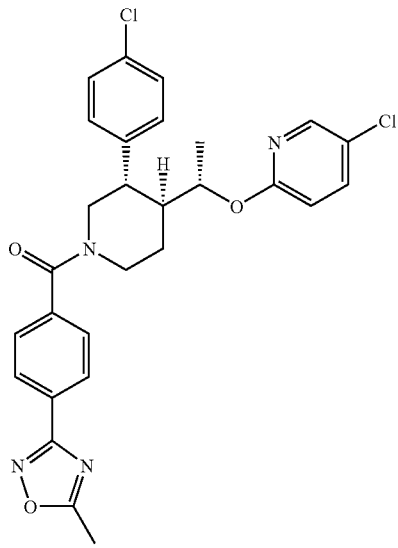

In analogy to the procedure described for the synthesis of [(3RS, 4RS)-3-(4-chloro-phenyl)-4-(5-chloro-pyridin-2-yloxymethyl)-piperidin-1-yl]-[4-(3-methyl-[1,2,4]oxadiazol-5-yl)-phenyl]-methanone (example 1, step i) the title compound was prepared from 5-Chloro-2-{(S)-1-[(3S,4S)-3-(4-chloro-phenyl)-piperidin-4-yl]-ethoxy}-pyridine and 4-Methane sulfonyl-piperazine-1-carbonyl chloride (WO 2009024502) as white solid. MS (m/e): 541.3 [(M+H)$^+$].

Example 15

{(3S,4S)-3-(4-Chloro-phenyl)-4-[(S)-1-(5-chloro-pyridin-2-yloxy)-ethyl]-piperidin-1-yl}-(4'-fluoro-biphenyl-4-yl)-methanone

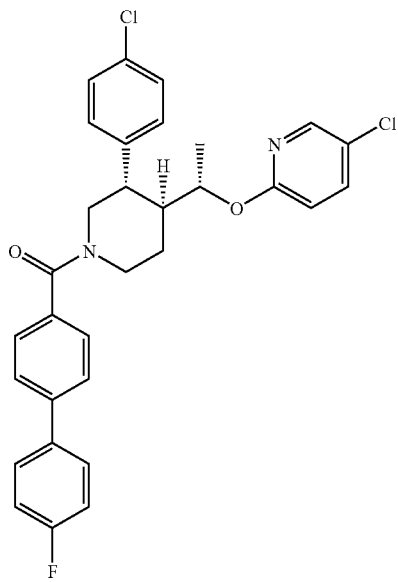

In analogy to the procedure described for the synthesis of [(3RS, 4RS)-3-(4-chloro-phenyl)-4-(5-chloro-pyridin-2-yloxymethyl)-piperidin-1-yl]-[4-(3-methyl-[1,2,4]oxadiazol-5-yl)-phenyl]-methanone (example 1, step i) the title compound was prepared from 5-Chloro-2-{(S)-1-[(3S,4S)-3-(4-chloro-phenyl)-piperidin-4-yl]-ethoxy}-pyridine and 4'-Fluoro-biphenyl-4-carboxylic acid (commercially available) as white solid. MS (m/e): 551.3 [(M+H)$^+$].

Example 16

(4-{(3S,4S)-3-(4-Chloro-phenyl)-4-[(S)-1-(5-trifluoromethyl-pyridin-2-yloxy)-ethyl]-piperidine-1-carbonyl}-piperidin-1-yl)-(1-methyl-cyclopropyl)-methanone

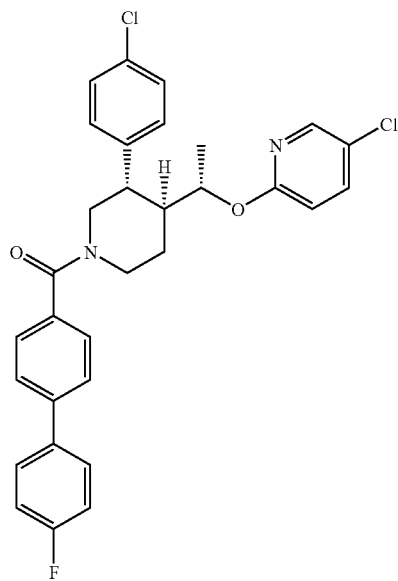

a) 2-{(S)-1-[(3S,4S)-1-Benzyl-3-(4-chloro-phenyl)-piperidin-4-yl]-ethoxy}-5-trifluoromethyl-pyridine

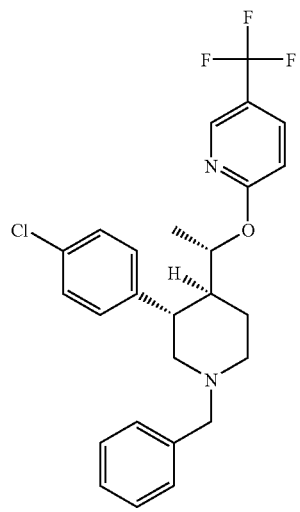

In analogy to the procedure described for the synthesis of 2-{(SR)-1-[(3SR,4SR)-1-Benzyl-3-(4-chloro-phenyl)-piperidin-4-yl]-ethoxy}-5-chloro-pyridine the title compound was prepared from (R)-1-[(3S,4S)-1-Benzyl-3-(4-chloro-phenyl)-piperidin-4-yl]-ethanol and 5-Trifluoromethyl-pyridin-2-ol as viscous colorless oil. MS (m/e): 475.2 [(M+H)+].

b) 2-{(S)-1-[(3S,4S)-3-(4-Chloro-phenyl)-piperidin-4-yl]-ethoxy}-5-trifluoromethyl-pyridine

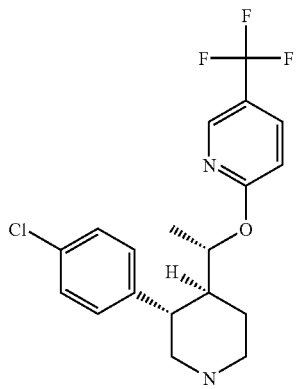

In analogy to the procedure described for the synthesis of 5-chloro-2-[(3RS, 4RS)-3-(4-chloro-phenyl)-piperidin-4-yl-methoxy]-pyridine; hydrochloride (example 1, step h) the title compound was prepared from 2-{(S)-1-[(3S,4S)-1-Benzyl-3-(4-chloro-phenyl)-piperidin-4-yl]-ethoxy}-5-trifluoromethyl-pyridine as off-white foam as the respective HCl salt. MS (m/e): 385.2 [(M+H)+].

c) (4-{(3S,4S)-3-(4-Chloro-phenyl)-4-[(S)-1-(5-trifluoromethyl-pyridin-2-yloxy)-ethyl]-piperidine-1-carbonyl}-piperidin-1-yl)-(1-methyl-cyclopropyl)-methanone In analogy to the procedure described for the synthesis of [(3RS, 4RS)-3-(4-chloro-phenyl)-4-(5-chloro-pyridin-2-yloxymethyl)-piperidin-1-yl]-[4-(3-methyl-[1,2,4]oxadiazol-5-yl)-phenyl]-methanone (example 1, step i) the title compound was prepared from 2-{(S)-1-[(3S,4S)-3-(4-Chloro-phenyl)-piperidin-4-yl]-ethoxy}-5-trifluoromethyl-pyridine and 1-(1-methyl-cyclopropanecarbonyl)-piperidine-4-carboxylic acid as white solid. MS (m/e): 578.2 [(M+H)+].

Example 17

{(3S,4S)-3-(4-Chloro-phenyl)-4-[(S)-1-(5-trifluoromethyl-pyridin-2-yloxy)-ethyl]-piperidin-1-yl}-(6-methyl-pyridazin-4-yl)-methanone

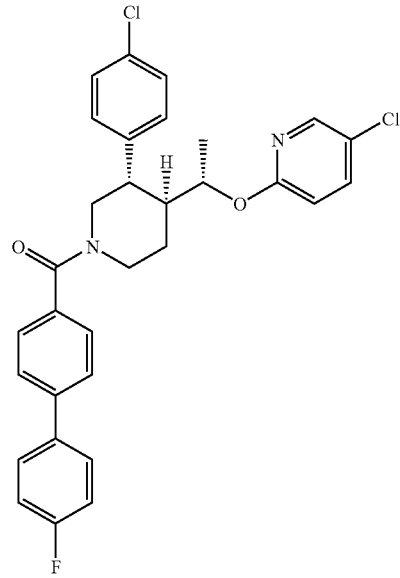

In analogy to the procedure described for the synthesis of [(3RS, 4RS)-3-(4-chloro-phenyl)-4-(5-chloro-pyridin-2-yloxymethyl)-piperidin-1-yl]-[4-(3-methyl-[1,2,4]oxadiazol-5-yl)-phenyl]-methanone (example 1, step i) the title compound was prepared from 2-{(S)-1-[(3S,4S)-3-(4-Chloro-phenyl)-piperidin-4-yl]-ethoxy}-5-trifluoromethyl-pyridine and 6-Methyl-pyridazine-4-carboxylic acid (WO2009019163) as white solid. MS (m/e): 505.2 [(M+H)+].

Example 18

{(3S,4S)-3-(4-Chloro-phenyl)-4-[(S)-1-(5-trifluoromethyl-pyridin-2-yloxy)-ethyl]-piperidin-1-yl}-[4-(3-methyl-[1,2,4]oxadiazol-5-yl)-phenyl]-methanone

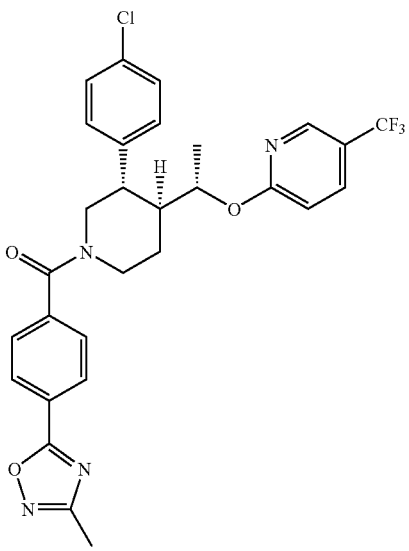

In analogy to the procedure described for the synthesis of [(3RS, 4RS)-3-(4-chloro-phenyl)-4-(5-chloro-pyridin-2-yloxymethyl)-piperidin-1-yl]-[4-(3-methyl-[1,2,4]oxadiazol-5-yl)-phenyl]-methanone (example 1, step i) the title compound was prepared from 2-{(S)-1-[(3S,4S)-3-(4-Chloro-phenyl)-piperidin-4-yl]-ethoxy}-5-trifluoromethyl-pyridine and 4-(3-Methyl-[1,2,4]oxadiazol-5-yl)-benzoic acid (commercially available) as white solid. MS (m/e): 571.3 [(M+H)⁺].

Example 19

{(3S,4S)-3-(4-Chloro-phenyl)-4-[(S)-1-(5-trifluoromethyl-pyridin-2-yloxy)-ethyl]-piperidin-1-yl}-[4-(5-methyl-[1,2,4]oxadiazol-3-yl)-phenyl]-methanone

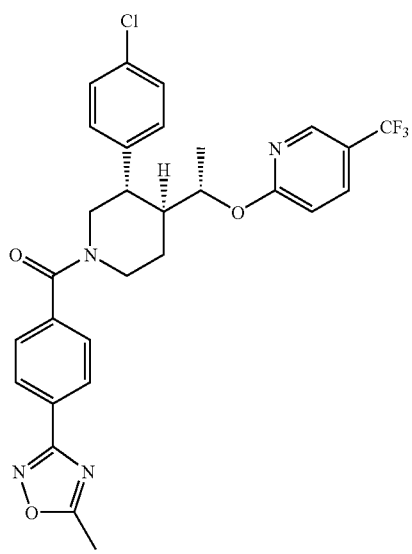

In analogy to the procedure described for the synthesis of [(3RS, 4RS)-3-(4-chloro-phenyl)-4-(5-chloro-pyridin-2-yloxymethyl)-piperidin-1-yl]-[4-(3-methyl-[1,2,4]oxadiazol-5-yl)-phenyl]-methanone (example 1, step i) the title compound was prepared from 2-{(S)-1-[(3S,4S)-3-(4-Chloro-phenyl)-piperidin-4-yl]-ethoxy}-5-trifluoromethyl-pyridine and 445-M ethyl-[1,2,4]oxadiazol-3-yl)-benzoic acid (commercially available) as white solid. MS (m/e): 571.2 [(M+H)⁺].

Example 20

4-{(3S,4S)-3-(4-Chloro-phenyl)-4-[(S)-1-(5-trifluoromethyl-pyridin-2-yloxy)-ethyl]-piperidine-1-carbonyl}-3,4,5,6-tetrahydro-2H-[1,2']bipyridinyl-5'-carbonitrile

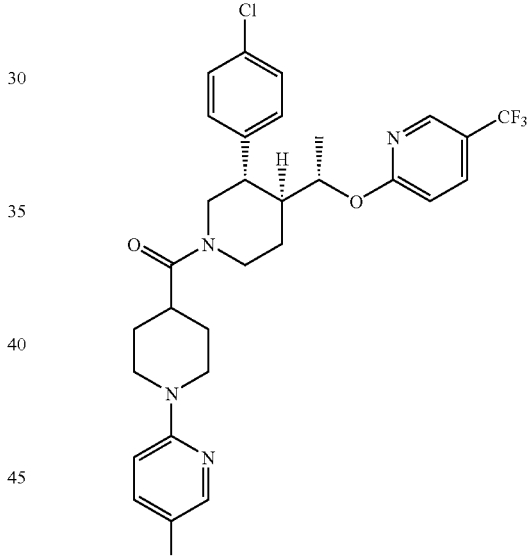

In analogy to the procedure described for the synthesis of [(3RS, 4RS)-3-(4-chloro-phenyl)-4-(5-chloro-pyridin-2-yloxymethyl)-piperidin-1-yl]-[4-(3-methyl-[1,2,4]oxadiazol-5-yl)-phenyl]-methanone (example 1, step i) the title compound was prepared from 2-{(S)-1-[(3S,4S)-3-(4-Chloro-phenyl)-piperidin-4-yl]-ethoxy}-5-trifluoromethyl-pyridine and 5'-Cyano-3,4,5,6-tetrahydro-2H-[1,2']bipyridinyl-4-carboxylic acid (commercially available) as white solid. MS (m/e): 598.3 [(M+H)⁺].

Example 21

{(3S,4S)-3-(4-Chloro-phenyl)-4-[(S)-1-(5-trifluoromethyl-pyridin-2-yloxy)-ethyl]-piperidin-1-yl}-(4-methanesulfonyl-piperazin-1-yl)-methanone

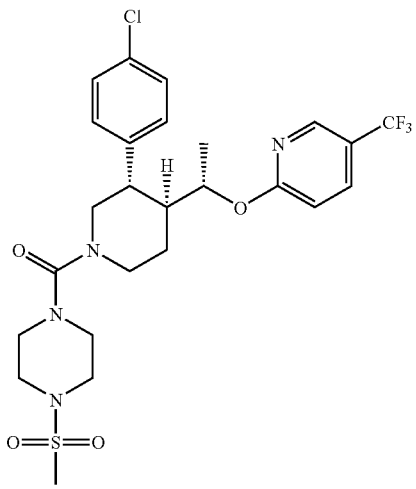

In analogy to the procedure described for the synthesis of [(3RS, 4RS)-3-(4-chloro-phenyl)-4-(5-chloro-pyridin-2-yloxymethyl)-piperidin-1-yl]-[4-(3-methyl-[1,2,4]oxadiazol-5-yl)-phenyl]-methanone (example 1, step i) the title compound was prepared from 2-{(S)-1-[(3S,4S)-3-(4-Chloro-phenyl)-piperidin-4-yl]-ethoxy}-5-trifluoromethyl-pyridine and 4-Methanesulfonyl-piperazine-1-carbonyl chloride (WO 2009024502) as white solid. MS (m/e): 575.3 [(M+H)$^+$].

Example 22

{(3S,4S)-3-(4-Chloro-phenyl)-4-[(S)-1-(5-trifluoromethyl-pyridin-2-yloxy)-ethyl]-piperidin-1-yl}-(4'-fluoro-biphenyl-4-yl)-methanone

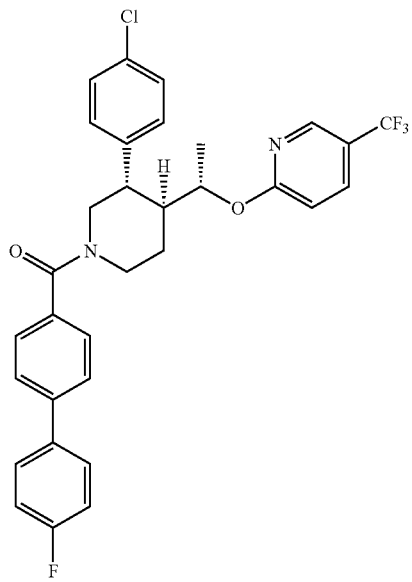

In analogy to the procedure described for the synthesis of [(3RS, 4RS)-3-(4-chloro-phenyl)-4-(5-chloro-pyridin-2-yloxymethyl)-piperidin-1-yl]-[4-(3-methyl-[1,2,4]oxadiazol-5-yl)-phenyl]-methanone (example 1, step i) the title compound was prepared from 2-{(S)-1-[(3S,4S)-3-(4-Chloro-phenyl)-piperidin-4-yl]-ethoxy}-5-trifluoromethyl-pyridine and 4'-Fluoro-biphenyl-4-carboxylic acid (commercially available) as white solid. MS (m/e): 583.2 [(M+H)$^+$].

Example 23

6-((S)-1-{(3S,4S)-3-(4-Chloro-phenyl)-1-[1-(1-methyl-cyclopropanecarbonyl)-piperidine-4-carbonyl]-piperidin-4-yl}-ethoxy)-nicotinonitrile

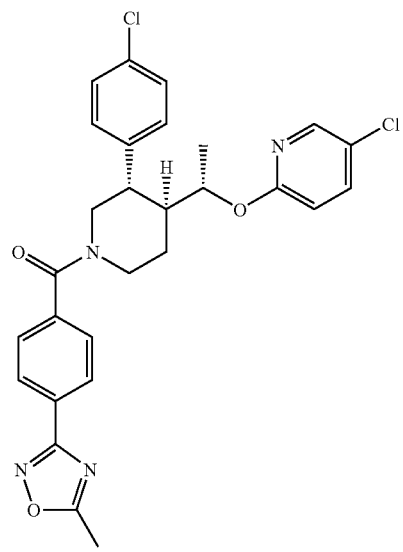

a) 6-{(S)-1-[(3S,4S)-1-Benzyl-3-(4-chloro-phenyl)-piperidin-4-yl]-ethoxy}-nicotinonitrile

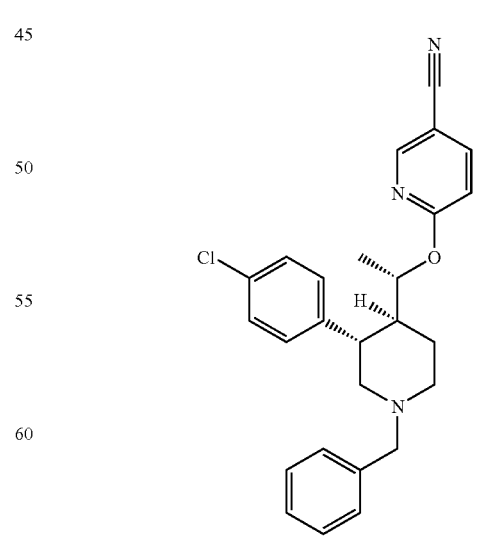

In analogy to the procedure described for the synthesis of 2-{(SR)-1-[(3SR,4SR)-1-Benzyl-3-(4-chloro-phenyl)-piperidin-4-yl]-ethoxy}-5-chloro-pyridine the title compound was prepared from (R)-1-[(3S,4S)-1-Benzyl-3-(4-chloro-phenyl)-piperidin-4-yl]-ethanol and 6-Hydroxy-nicotinonitrile. MS (m/e): 432.3 [(M+H)⁺].

b) 6-{(S)-1-[(3S,4S)-3-(4-Chloro-phenyl)-piperidin-4-yl]-ethoxy}-nicotinonitrile

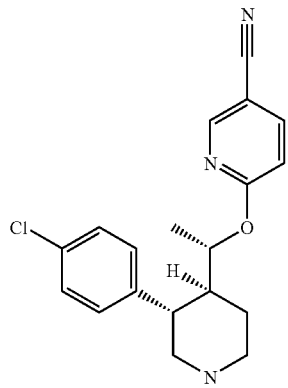

In analogy to the procedure described for the synthesis of 5-chloro-2-[(3RS, 4RS)-3-(4-chloro-phenyl)-piperidin-4-yl-methoxy]-pyridine; hydrochloride (example 1, step h) the title compound was prepared from 2-{(S)-1-[(3S,4S)-1-Benzyl-3-(4-chloro-phenyl)-piperidin-4-yl]-ethoxy}-5-trifluoromethyl-pyridine as white foam as the respective HCl salt. MS (m/e): 342.1 [(M+H)⁺].

c) 6-((S)-1-{(3S,4S)-3-(4-Chloro-phenyl)-1-[1-(1-methyl-cyclopropanecarbonyl)-piperidine-4-carbonyl]-piperidin-4-yl}-ethoxy)-nicotinonitrile In analogy to the procedure described for the synthesis of [(3RS, 4RS)-3-(4-chloro-phenyl)-4-(5-chloro-pyridin-2-yloxymethyl)-piperidin-1-yl]-[4-(3-methyl-[1,2,4]oxadiazol-5-yl)-phenyl]-methanone (example 1, step i) the title compound was prepared from 6-{(S)-1-[(3S,4S)-3-(4-Chloro-phenyl)-piperidin-4-yl]-ethoxy}-nicotinonitrile and 1-(1-methyl-cyclopropanecarbonyl)-piperidine-4-carboxylic acid as white solid. MS (m/e): 535.4 [(M+H)⁺].

Example 24

6-{(S)-1-[(3S,4S)-3-(4-Chloro-phenyl)-1-(6-methyl-pyridazine-4-carbonyl)-piperidin-4-yl]-ethoxy}-nicotinonitrile

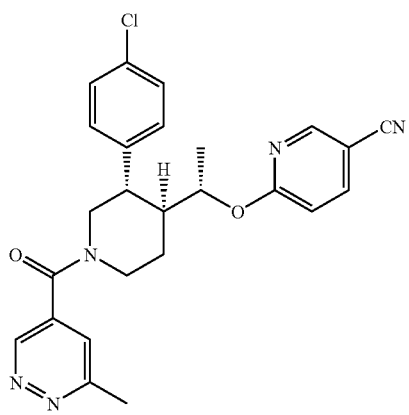

In analogy to the procedure described for the synthesis of [(3RS, 4RS)-3-(4-chloro-phenyl)-4-(5-chloro-pyridin-2-yloxymethyl)-piperidin-1-yl]-[4-(3-methyl-[1,2,4]oxadiazol-5-yl)-phenyl]-methanone (example 1, step i) the title compound was prepared from 6-{(S)-1-[(3S,4S)-3-(4-Chloro-phenyl)-piperidin-4-yl]-ethoxy}-nicotinonitrile and 6-Methyl-pyridazine-4-carboxylic acid (WO2009019163) as white solid. MS (m/e): 462.1 [(M+H)⁺].

Example 25

6-((S)-1-{(3S,4S)-3-(4-Chloro-phenyl)-1-[4-(3-methyl-[1,2,4]oxadiazol-5-yl)-benzoyl]-piperidin-4-yl}-ethoxy)-nicotinonitrile

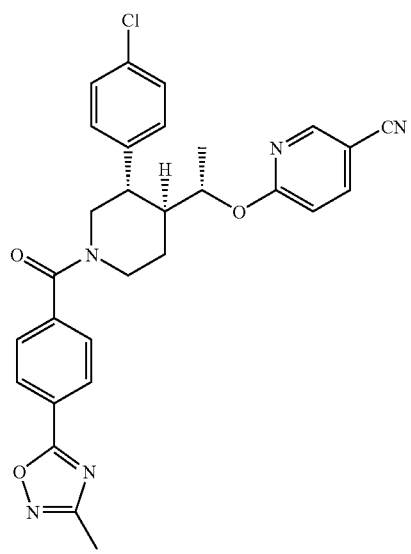

In analogy to the procedure described for the synthesis of [(3RS, 4RS)-3-(4-chloro-phenyl)-4-(5-chloro-pyridin-2-yloxymethyl)-piperidin-1-yl]-[4-(3-methyl-[1,2,4]oxadiazol-5-yl)-phenyl]-methanone (example 1, step i) the title compound was prepared from 6-{(S)-1-[(3S,4S)-3-(4-Chloro-phenyl)-piperidin-4-yl]-ethoxy}-nicotinonitrile and 4-(3-Methyl-[1,2,4]oxadiazol-5-yl)-benzoic acid (commercially available) as white solid. MS (m/e): 528.3 [(M+H)⁺].

Example 26

6-((S)-1-{(3S,4S)-3-(4-Chloro-phenyl)-1-[4-(5-methyl-[1,2,4]oxadiazol-3-yl)-benzoyl]-piperidin-4-yl}-ethoxy)-nicotinonitrile

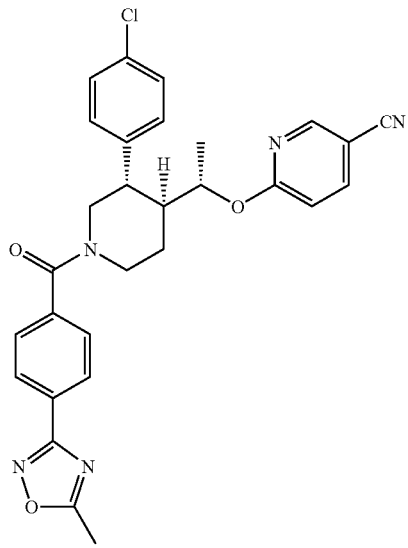

In analogy to the procedure described for the synthesis of [(3RS, 4RS)-3-(4-chloro-phenyl)-4-(5-chloro-pyridin-2-yloxymethyl)-piperidin-1-yl]-[4-(3-methyl-[1,2,4]oxadiazol-5-yl)-phenyl]-methanone (example 1, step i) the title compound was prepared from 6-{(S)-1-[(3S,4S)-3-(4-Chloro-phenyl)-piperidin-4-yl]-ethoxy}-nicotinonitrile and 4-(5-Methyl-[1,2,4]oxadiazol-3-yl)-benzoic acid (commercially available) as white solid. MS (m/e): 528.3 [(M+H)+].

Example 27

4-{(3S,4S)-3-(4-Chloro-phenyl)-4-[(S)-1-(5-cyano-pyridin-2-yloxy)-ethyl]-piperidine-1-carbonyl}-3,4,5,6-tetrahydro-2H-[1,2']bipyridinyl-5'-carbonitrile

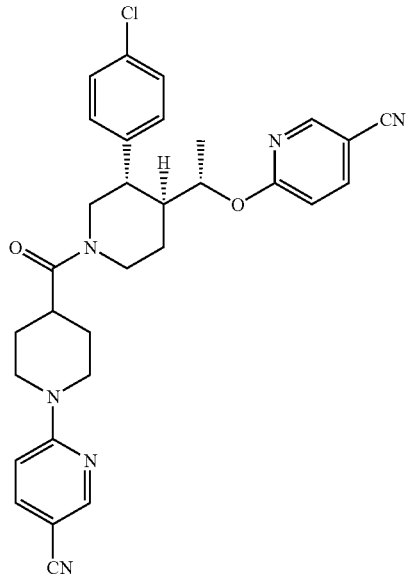

In analogy to the procedure described for the synthesis of [(3RS, 4RS)-3-(4-chloro-phenyl)-4-(5-chloro-pyridin-2-yloxymethyl)-piperidin-1-yl]-[4-(3-methyl-[1,2,4]oxadiazol-5-yl)-phenyl]-methanone (example 1, step i) the title compound was prepared from 6-{(S)-1-[(3S,4S)-3-(4-Chloro-phenyl)-piperidin-4-yl]-ethoxy}-nicotinonitrile and 5'-Cyano-3,4,5,6-tetrahydro-2H-[1,2']bipyridinyl-4-carboxylic acid (commercially available) as white solid. MS (m/e): 555.3 [(M+H)+].

Example 28

6-{(S)-1-[(3S,4S)-3-(4-Chloro-phenyl)-1-(4-methanesulfonyl-piperazine-1-carbonyl)-piperidin-4-yl]-ethoxy}-nicotinonitrile

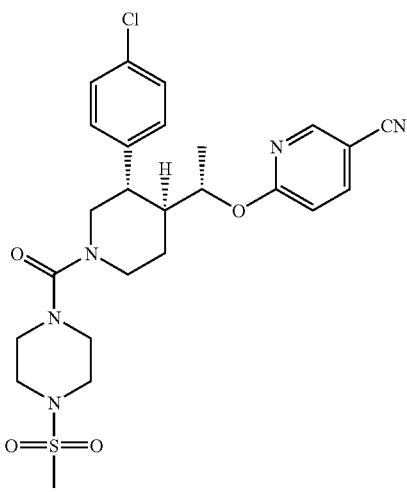

In analogy to the procedure described for the synthesis of [(3RS, 4RS)-3-(4-chloro-phenyl)-4-(5-chloro-pyridin-2-yloxymethyl)-piperidin-1-yl]-[4-(3-methyl-[1,2,4]oxadiazol-5-yl)-phenyl]-methanone (example 1, step i) the title compound was prepared from 6-{(S)-1-[(3S,4S)-3-(4-Chloro-phenyl)-piperidin-4-yl]-ethoxy}-nicotinonitrile and 4-Methanesulfonyl-piperazine-1-carbonyl chloride (WO 2009024502) as white solid. MS (m/e): 532.2 [(M+H)+].

Example 29

6-{(S)-1-[(3S,4S)-3-(4-Chloro-phenyl)-1-(4'-fluoro-biphenyl-4-carbonyl)-piperidin-4-yl]-ethoxy}-nicotinonitrile

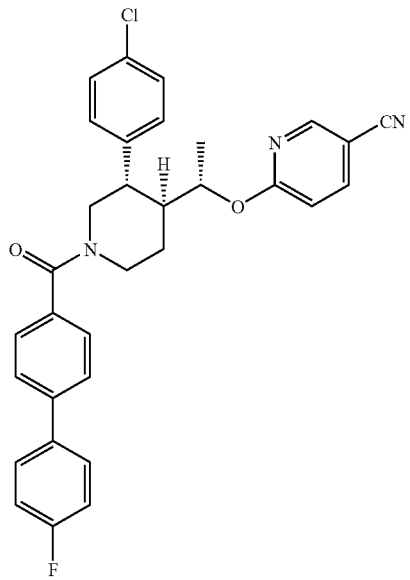

In analogy to the procedure described for the synthesis of [(3RS, 4RS)-3-(4-chloro-phenyl)-4-(5-chloro-pyridin-2-yloxymethyl)-piperidin-1-yl]-[4-(3-methyl-[1,2,4]oxadiazol-5-yl)-phenyl]-methanone (example 1, step i) the title compound was prepared from 6-{(S)-1-[(3S,4S)-3-(4-Chloro-phenyl)-piperidin-4-yl]-ethoxy}-nicotinonitrile and 4'-Fluoro-biphenyl-4-carboxylic acid (commercially available) as white solid. MS (m/e): 540.4 [(M+H)$^+$].

Example 30

[(3SR,4SR)-4-(5-Chloro-pyridin-2-yloxymethyl)-3-(3,4-difluoro-phenyl)-piperidin-1-yl]-(4'-fluoro-biphenyl-4-yl)-methanone

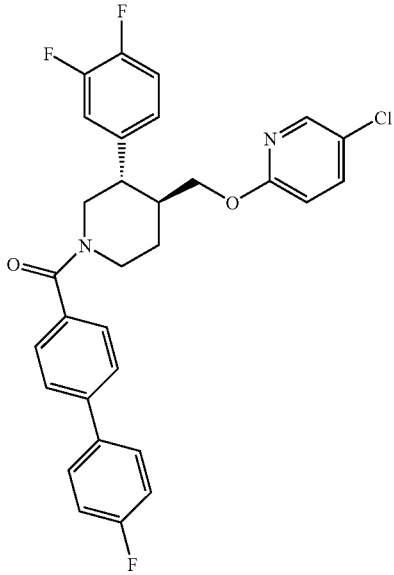

a) 1-Benzyl-5-(3,4-difluoro-phenyl)-1,2,3,6-tetrahydro-pyridine-4-carboxylic acid ethyl ester

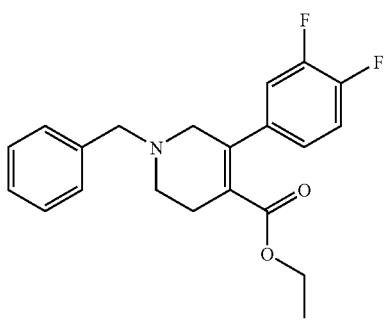

In analogy to the procedure described for the synthesis of 1-Benzyl-5-(4-chloro-phenyl)-1,2,3,6-tetrahydro-pyridine-4-carboxylic acid ethyl ester (example 1 a)) the title compound was obtained from ethyl N-benzyl-3-oxo-4-piperidine-carboxylate (commercially available) and 3,4-difluorophenylboronic acid as yellow viscous oil. MS (m/e): 358.2 [(M+H)$^+$].

b) (3SR,4RS)-3-(3,4-Difluoro-phenyl)-piperidine-4-carboxylic acid ethyl ester

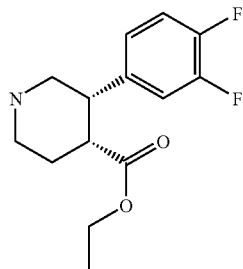

A solution of 2.73 g (7.6 mmol) 1-benzyl-5-(3,4-difluoro-phenyl)-1,2,3,6-tetrahydro-pyridine-4-carboxylic acid ethyl ester in 150 mL ethanol was hydrogenated over 600 mg Pd/C (10%). The catalyst was filtered off and the filtrate was evaporated to dryness to yield 2 g (87%) of the title compound which was used without further purification in the subsequent step. MS (m/e): 270.3 [(M+H)$^+$].

c) (3SR,4RS)-3-(3,4-Difluoro-phenyl)-piperidine-1,4-dicarboxylic acid 1-tert-butyl ester 4-ethyl ester

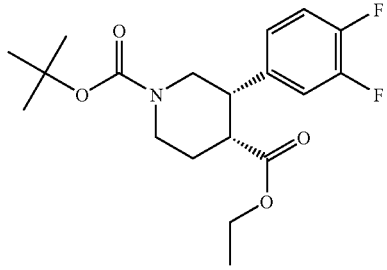

A mixture of 2 g (7.4 mmol) (3SR,4RS)-3-(3,4-Difluoro-phenyl)-piperidine-4-carboxylic acid ethyl ester, 1.78 g (8.1 mmol) di-tert.-butyl-dicarbonate and catalytic amount DMAP in 60 mL THF was stirred at room temperature. After evaporation the residue was subjected to column chromatography on silica eluting with gradient formed from heptane and TBME to afford after evaporation of the product containing fractions 2.2 g (80%) of the title compound as light yellow viscous oil. MS (m/e): 270.1 [(M+H-Boc)+].

d) (3SR,4SR)-3-(3,4-Difluoro-phenyl)-piperidine-1, 4-dicarboxylic acid 1-tert-butyl ester 4-methyl ester

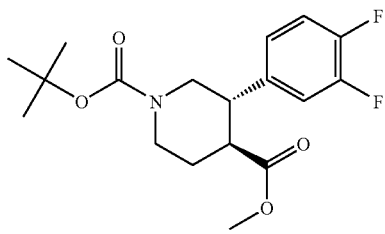

A mixture of 2.2 g (5.9 mmol) (3SR,4RS)-3-(3,4-Difluoro-phenyl)-piperidine-1,4-dicarboxylic acid 1-tert-butyl ester 4-ethyl ester and 0.18 mL NaOMe (5.4N in methanol) in 60 mL methanol was first stirred at room temperature and subsequently ar reflux until consumption of the starting material. The mixture was evaporated to dryness and the residue subjected to column chromatography on silica eluting with a gradient formed from ethyl acetate and heptane to afford after evaporation of the product containing fractions 1.5 g (71%) of the title compound as colorless oil. MS (m/e): 256.1 [(M+H-Boc)+].

e) (3SR,4SR)-3-(3,4-Difluoro-phenyl)-4-hydroxymethyl-piperidine-1-carboxylic acid tert-butyl ester

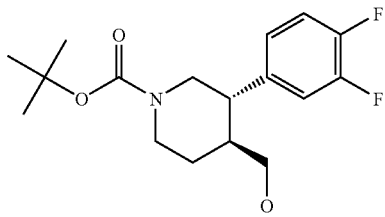

A mixture of 1.5 g (4.2 mmol) (3SR,4SR)-3-(3,4-Difluoro-phenyl)-piperidine-1,4-dicarboxylic acid 1-tert-butyl ester 4-methyl ester and 0.16 g (4.2 mmol) LiAlH4 in 50 mL THF was stirred at room temperature for 1 h. Ethyl acetate, THF, water and NaOH aq. was added. Na2SO4 was added, the mixture was filtered off and evaporated to dryness. The residue was subjected to column chromatography on silica eluting with a gradient formed from ethyl acetate and heptane to afford after evaporation of the product containing fractions 1.06 g (77%) of the title compound as viscous colorless oil. MS (m/e): 228.1 [(M+H-Boc)+].

f) (3SR,4SR)-4-(5-Chloro-pyridin-2-yloxymethyl)-3-(3,4-difluoro-phenyl)-piperidine-1-carboxylic acid tert-butyl ester

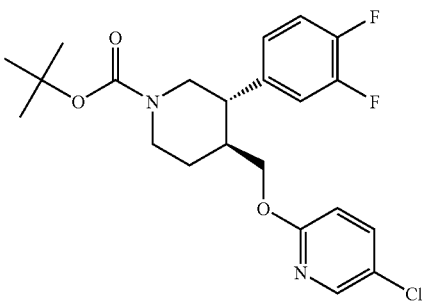

A mixture of 1 g (3 mmol) (3SR,4SR)-3-(3,4-Difluoro-phenyl)-4-hydroxymethyl-piperidine-1-carboxylic acid tert-butyl ester, 0.59 g (4.5 mmol) 5-chloro-2-hydroxy pyridine, 1.1 g (4.8 mmol) di-tert-butyl azodicarboxylate and 2.42 g (5 mmol) triphenylphosphine (polymer bound) in 70 mL THF was stirred at room temperature over night. the mixture was filtered through decalite and evaporated to dryness. The residue was subjected to column chromatography on silica eluting with a gradient formed from ethyl acetate and heptane to afford after evaporation of the product containing fractions 1.2 g (91%) of the title compound as viscous colorless oil. MS (m/e): 439.1 [(M+H)+].

g) 5-Chloro-2-[(3SR,4SR)-3-(3,4-difluoro-phenyl)-piperidin-4-ylmethoxy]-pyridine; hydrochloride

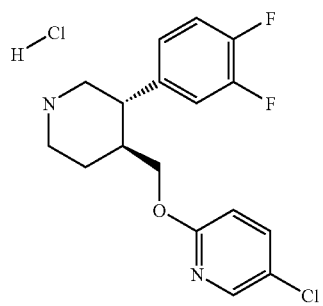

A solution of 1.2 g (2.7 mmol) (3SR,4SR)-4-(5-Chloro-pyridin-2-yloxymethyl)-3-(3,4-difluoro-phenyl)-piperidine-1-carboxylic acid tert-butyl ester in 15 mL methanol was treated with 6.8 mL HCl in dioxane (4N) and stirred for 4 h at room temperature. The mixture was evaporated to dryness and dried under high vacuum to afford the title compound which was used without further purification in the subsequent step. MS (m/e): 339.3 [(M+H)+].

h [(3SR,4SR)-4-(5-Chloro-pyridin-2-yloxymethyl)-3-(3,4-difluoro-phenyl)-piperidin-1-yl]-(4'-fluoro-biphenyl-4-yl)-methanone In analogy to the procedure described for the synthesis of [(3RS, 4RS)-3-(4-chloro-phenyl)-4-(5-chloro-pyridin-2-yloxymethyl)-piperidin-1-yl]-[4-(3-methyl-[1,2,4]oxadiazol-5-yl)-phenyl]-methanone (example 1, step i) the title compound was prepared from 5-Chloro-2-[(3SR,4SR)-3-(3, 4-difluoro-phenyl)-piperidin-4-ylmethoxy]-pyridine; hydrochloride and 4'-Fluoro-biphenyl-4-carboxylic acid (commercially available) as off-white solid. MS (m/e): 537.3 [(M+H)+].

Example 31

[(3SR,4SR)-4-(5-Chloro-pyridin-2-yloxymethyl)-3-(3,4-difluoro-phenyl)-piperidin-1-yl]-[4-(3-methyl-[1,2,4]oxadiazol-5-yl)-phenyl]-methanone

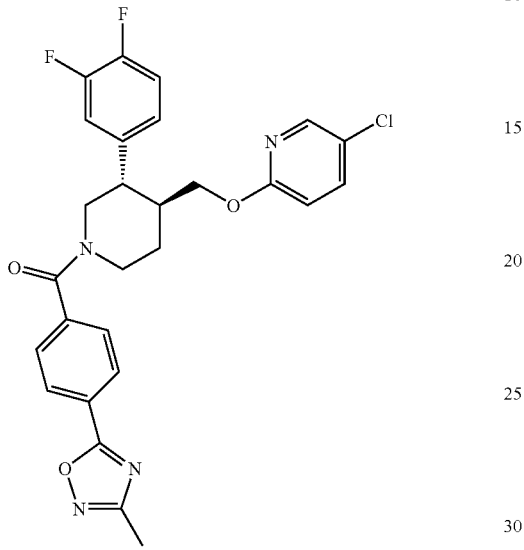

In analogy to the procedure described for the synthesis of [(3RS, 4RS)-3-(4-chloro-phenyl)-4-(5-chloro-pyridin-2-yloxymethyl)-piperidin-1-yl]-[4-(3-methyl-[1,2,4]oxadiazol-5-yl)-phenyl]-methanone (example 1, step i) the title compound was prepared from 5-Chloro-2-[(3SR,4SR)-3-(3,4-difluoro-phenyl)-piperidin-4-ylmethoxy]-pyridine; hydrochloride and 4-(3-Methyl-[1,2,4]oxadiazol-5-yl)-benzoic acid (commercially available) as off-white solid. MS (m/e): 525.3 [(M+H)+].

Example 32

{4-[(3SR,4SR)-4-(5-Chloro-pyridin-2-yloxymethyl)-3-(3,4-difluoro-phenyl)-piperidine-1-carbonyl]-piperidin-1-yl}-(1-methyl-cyclopropyl)-methanone

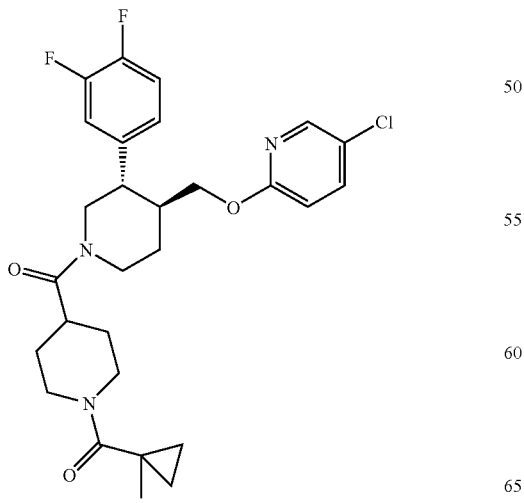

In analogy to the procedure described for the synthesis of [(3RS, 4RS)-3-(4-chloro-phenyl)-4-(5-chloro-pyridin-2-yloxymethyl)-piperidin-1-yl]-[4-(3-methyl-[1,2,4]oxadiazol-5-yl)-phenyl]-methanone (example 1, step i) the title compound was prepared from 5-Chloro-2-[(3SR,4SR)-3-(3,4-difluoro-phenyl)-piperidin-4-ylmethoxy]-pyridine; hydrochloride and 1-(1-methyl-cyclopropanecarbonyl)-piperidine-4-carboxylic acid (commercially available) as off-white solid. MS (m/e): 532.3 [(M+H)+].

Example 33

4-[(3S,4S)-4-(5-Chloro-pyridin-2-yloxymethyl)-3-(3,4-difluoro-phenyl)-piperidine-1-carbonyl]-3,4,5,6-tetrahydro-2H-[1,3']bipyridinyl-6'-carbonitrile

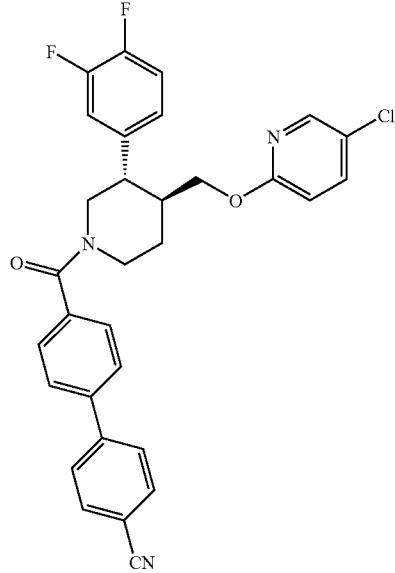

In analogy to the procedure described for the synthesis of [(3RS, 4RS)-3-(4-chloro-phenyl)-4-(5-chloro-pyridin-2-yloxymethyl)-piperidin-1-yl]-[4-(3-methyl-[1,2,4]oxadiazol-5-yl)-phenyl]-methanone (example 1, step i) the title compound was prepared from 5-Chloro-2-[(3SR,4SR)-3-(3,4-difluoro-phenyl)-piperidin-4-ylmethoxy]-pyridine; hydrochloride and 5'-Cyano-3,4,5,6-tetrahydro-2H-[1,2']bipyridinyl-4-carboxylic acid (commercially available) as off-white solid. MS (m/e): 552.4 [(M+H)+].

Example 34

[(3SR,4SR)-4-(5-Chloro-pyridin-2-yloxymethyl)-3-(3,4-difluoro-phenyl)-piperidin-1-yl]-(4-methanesulfonyl-piperazin-1-yl)-methanone

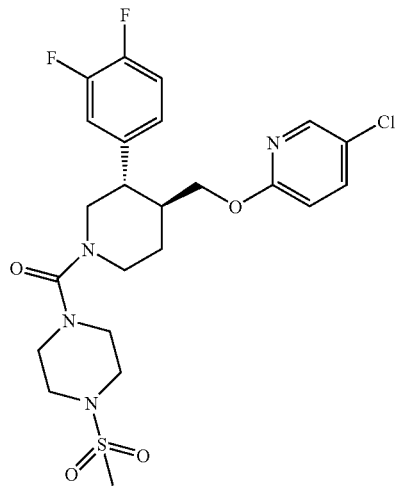

In analogy to the procedure described for the synthesis of [(3RS, 4RS)-3-(4-chloro-phenyl)-4-(5-chloro-pyridin-2-yloxymethyl)-piperidin-1-yl]-[4-(3-methyl-[1,2,4]oxadiazol-5-yl)-phenyl]-methanone (example 1, step i) the title compound was prepared from 5-Chloro-2-[(3SR,4SR)-3-(3,4-difluoro-phenyl)-piperidin-4-ylmethoxy]-pyridine; hydrochloride and 4-Methanesulfonyl-piperazine-1-carbonyl chloride (WO2009024502) as off-white solid. MS (m/e): 529.2 [(M+H)+].

Example 35

[(3S,4S)-4-(5-Chloro-pyridin-2-yloxymethyl)-3-(3,4-difluoro-phenyl)-piperidin-1-yl]-(6-methyl-pyridazin-4-yl)-methanone

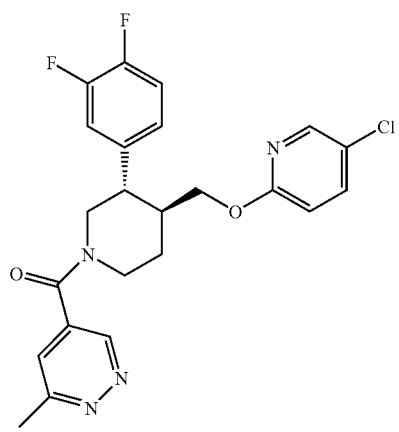

In analogy to the procedure described for the synthesis of [(3RS, 4RS)-3-(4-chloro-phenyl)-4-(5-chloro-pyridin-2-yloxymethyl)-piperidin-1-yl]-[4-(3-methyl-[1,2,4]oxadiazol-5-yl)-phenyl]-methanone (example 1, step i) the title compound was prepared from 5-Chloro-2-[(3SR,4SR)-3-(3,4-difluoro-phenyl)-piperidin-4-ylmethoxy]-pyridine; hydrochloride and 6-Methyl-pyridazine-4-carboxylic acid (WO2009019163) as off-white solid. MS (m/e): 459.3 [(M+H)+].

Example 36

4-[(3SR,4SR)-4-(5-Chloro-pyridin-2-yloxymethyl)-3-(3,4-difluoro-phenyl)-piperidine-1-carbonyl]-3,4,5,6-tetrahydro-2H-[1,2']bipyridinyl-4'-carbonitrile

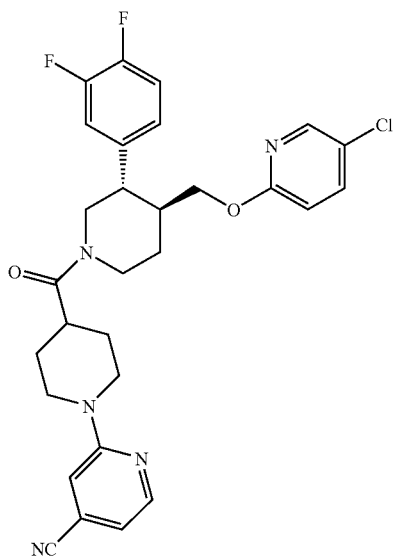

In analogy to the procedure described for the synthesis of [(3RS, 4RS)-3-(4-chloro-phenyl)-4-(5-chloro-pyridin-2-yloxymethyl)-piperidin-1-yl]-[4-(3-methyl-[1,2,4]oxadiazol-5-yl)-phenyl]-methanone (example 1, step i) the title compound was prepared from 5-Chloro-2-[(3SR,4SR)-3-(3,4-difluoro-phenyl)-piperidin-4-ylmethoxy]-pyridine; hydrochloride and 4'-Cyano-3,4,5,6-tetrahydro-2H-[1,2']bipyridinyl-4-carboxylic acid (commercially available) as off-white solid. MS (m/e): 552.1 [(M+H)+].

Example 37

[4-(5-Chloro-pyridin-2-yloxymethyl)-3-(4-fluoro-phenyl)-piperidin-1-yl]-[1-(1-methyl-cyclopropanecarbonyl)-piperidin-4-yl]-methanone

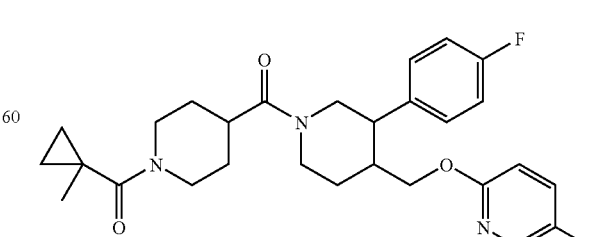

a) (3SR,4RS)-3-(4-Fluoro-phenyl)-piperidine-4-carboxylic acid methyl ester

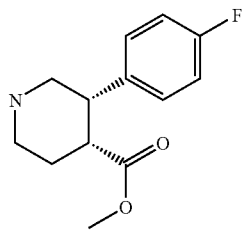

A mixture of 3.6 g (1.03 mmol) 1-Benzyl-5-(4-fluoro-phenyl)-1,2,3,6-tetrahydro-pyridine-4-carboxylic acid (Bioorganic & Medicinal Chemistry Letters 2003, 2513-2518); hydrochloride, 16.6 mL HCl in methanol (1.25 N) in 250 mL methanol was stirred at room temperature over night. Further 16.6 mL HCl in methanol (1.25 N) was added and the mixture was stirred at 70° C. and subsequently hydrogenated with $H_2$ over 360 mg Pd/C (10%) for 44 h at room temperature. The mixture was filtered off and evaporated to dryness to yield 2.3 g (94%) of the title compound as colorless oil. MS (m/e): 238.1 [(M+H)$^+$].

b) (3SR,4RS)-3-(4-Fluoro-phenyl)-piperidine-1,4-dicarboxylic acid 1-tert-butyl ester 4-methyl ester

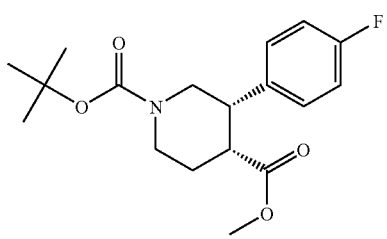

In analogy to the procedure described for the synthesis of (3SR,4RS)-3-(3,4-Difluoro-phenyl)-piperidine-1,4-dicarboxylic acid 1-tert-butyl ester 4-ethyl ester the title compound was prepared from (3SR,4RS)-3-(4-Fluoro-phenyl)-piperidine-4-carboxylic acid methyl ester and di-tert.-butyl-dicarbonate and catalytic amount DMAP as colorless viscous oil. MS (m/e): 238.1 [(M+H-Boc)$^+$].

c) 3-(4-Fluoro-phenyl)-piperidine-1,4-dicarboxylic acid 1-tert-butyl ester 4-methyl ester

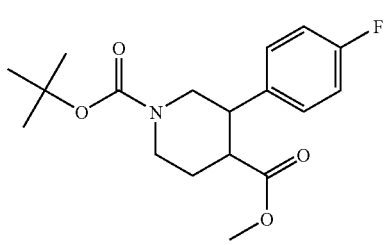

In analogy to the procedure described for the synthesis of (3SR,4SR)-3-(3,4-Difluoro-phenyl)-piperidine-1,4-dicarboxylic acid 1-tert-butyl ester 4-methyl ester the title compound was prepared from (3SR,4RS)-3-(4-Fluoro-phenyl)-piperidine-1,4-dicarboxylic acid 1-tert-butyl ester 4-methyl ester through epimerization with NaOMe in methanol as a 7:3 mixture cis:trans as colorless viscous oil. MS (m/e): 238.1 [(M+H-Boc)$^+$].

d) 3-(4-Fluoro-phenyl)-4-hydroxymethyl-piperidine-1-carboxylic acid tert-butyl ester

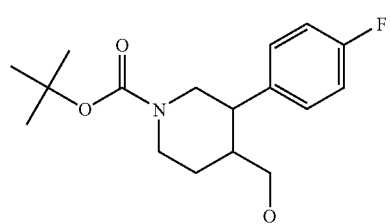

In analogy to the procedure described for the synthesis of (3SR,4SR)-3-(3,4-Difluoro-phenyl)-4-hydroxymethyl-piperidine-1-carboxylic acid tert-butyl ester the title compound was prepared from 3-(4-Fluoro-phenyl)-piperidine-1,4-dicarboxylic acid 1-tert-butyl ester 4-methyl ester through reduction as colorless viscous oil (7:3 mixture cis:trans). MS (m/e): 210.1 [(M+H-Boc)$^+$].

e) 4-(5-Chloro-pyridin-2-yloxymethyl)-3-(4-fluoro-phenyl)-piperidine-1-carboxylic acid tert-butyl ester

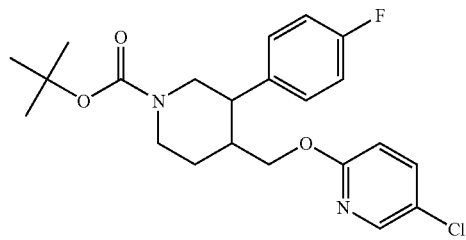

In analogy to the procedure described for the synthesis of (3SR,4SR)-4-(5-Chloro-pyridin-2-yloxymethyl)-3-(3,4-difluoro-phenyl)-piperidine-1-carboxylic acid tert-butyl ester the title compound was prepared through Mitsunobu reaction of 3-(4-Fluoro-phenyl)-4-hydroxymethyl-piperidine-1-carboxylic acid tert-butyl ester with 5-chloro-2-hydroxy pyridine as colorless viscous oil (7:3 mixture cis:trans). MS (m/e): 421.2 [(M+H)$^+$].

f) 5-Chloro-2-[3-(4-fluoro-phenyl)-piperidin-4-ylmethoxy]-pyridine; hydrochloride

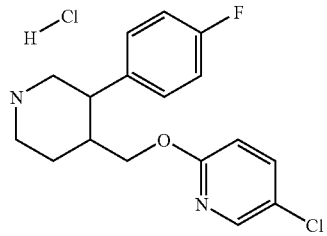

In analogy to the procedure described for the synthesis of 5-Chloro-2-[(3SR,4SR)-3-(3,4-difluoro-phenyl)-piperidin-4-ylmethoxy]-pyridine; hydrochloride the title compound was prepared from 445-Chloro-pyridin-2-yloxymethyl)-3-(4-fluoro-phenyl)-piperidine-1-carboxylic acid tert-butyl ester as off-white foam (7:3 mixture cis:trans). MS (m/e): 421.2 [(M+H)+].

g) [4-(5-Chloro-pyridin-2-yloxymethyl)-3-(4-fluoro-phenyl)-piperidin-1-yl]-[1-(1-methyl-cyclopropanecarbonyl)-piperidin-4-yl]-methanone In analogy to the procedure described for the synthesis of [(3RS, 4RS)-3-(4-chloro-phenyl)-4-(5-chloro-pyridin-2-yloxymethyl)-piperidin-1-yl]-[4-(3-methyl-[1,2,4]oxadiazol-5-yl)-phenyl]-methanone (example 1, step i) the title compound was prepared from 5-Chloro-2-[3-(4-fluoro-phenyl)-piperidin-4-ylmethoxy]-pyridine; hydrochloride and 1-(1-methyl-cyclopropanecarbonyl)-piperidine-4-carboxylic acid (commercially available) as off-white solid (7:3 mixture cis:trans). MS (m/e): 514.4 [(M+H)+].

Example 38

[4-(5-Chloro-pyridin-2-yloxymethyl)-3-(4-fluoro-phenyl)-piperidin-1-yl]-[4-(3-methyl-[1,2,4]oxadiazol-5-yl)-phenyl]-methanone

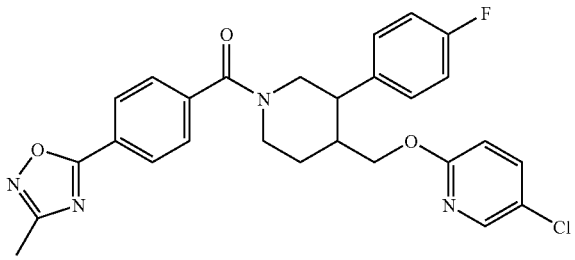

In analogy to the procedure described for the synthesis of [(3RS, 4RS)-3-(4-chloro-phenyl)-4-(5-chloro-pyridin-2-yloxymethyl)-piperidin-1-yl]-[4-(3-methyl-[1,2,4]oxadiazol-5-yl)-phenyl]-methanone (example 1, step i) the title compound was prepared from [4-(5-Chloro-pyridin-2-yloxymethyl)-3-(4-fluoro-phenyl)-piperidin-1-yl]-[1-(1-methyl-cyclopropanecarbonyl)-piperidin-4-yl]-methanone and 4-(3-Methyl-[1,2,4]oxadiazol-5-yl)-benzoic acid (commercially available) as off-white solid (7:3 mixture cis:trans). MS (m/e): 507.3 [(M+H)+].

Example 39

[4-(5-Chloro-pyridin-2-yloxymethyl)-3-(4-fluoro-phenyl)-piperidin-1-yl]-(4-methanesulfonyl-piperazin-1-yl)-methanone

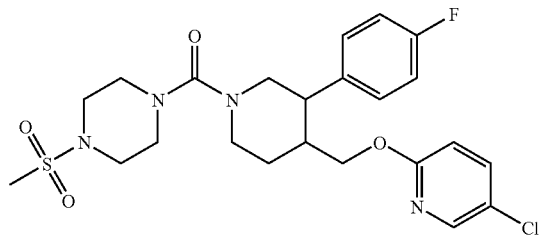

In analogy to the procedure described for the synthesis of [(3RS, 4RS)-3-(4-chloro-phenyl)-4-(5-chloro-pyridin-2-yloxymethyl)-piperidin-1-yl]-[4-(3-methyl-[1,2,4]oxadiazol-5-yl)-phenyl]-methanone (example 1, step i) the title compound was prepared from [4-(5-Chloro-pyridin-2-yloxymethyl)-3-(4-fluoro-phenyl)-piperidin-1-yl]-[1-(1-methyl-cyclopropanecarbonyl)-piperidin-4-yl]-methanone and 4-Methanesulfonyl-piperazine-1-carbonyl chloride (WO2009024502) as off-white solid (7:3 mixture cis:trans). MS (m/e): 511.3 [(M+H)+].

Example 40

[4-(5-Chloro-pyridin-2-yloxymethyl)-3-(4-methoxy-phenyl)-piperidin-1-yl]-[1-(1-methyl-cyclopropanecarbonyl)-piperidin-4-yl]-methanone

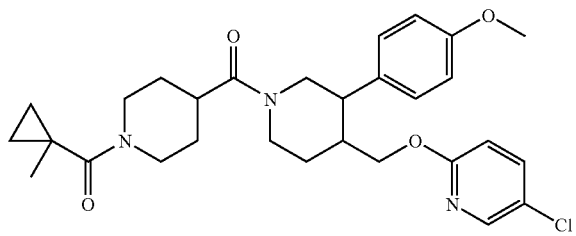

a) 1-Benzyl-5-(4-methoxy-phenyl)-1,2,3,6-tetrahydro-pyridine-4-carboxylic acid ethyl ester

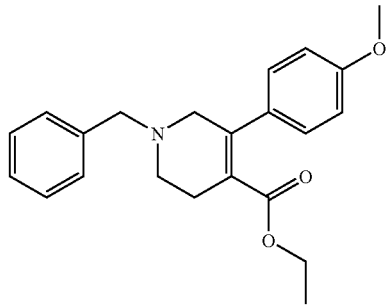

In analogy to the procedure described for the synthesis of 1-Benzyl-5-(4-chloro-phenyl)-1,2,3,6-tetrahydro-pyridine-4-carboxylic acid ethyl ester the title compound was prepared from ethyl N-benzyl-3-oxo-4-piperidine-carboxylate and 4-methoxyphenylboronic acid as yellow viscous oil. MS (m/e): 352.3 [(M+H)+].

b) (3SR,4RS)-3-(4-Methoxy-phenyl)-piperidine-4-carboxylic acid ethyl ester

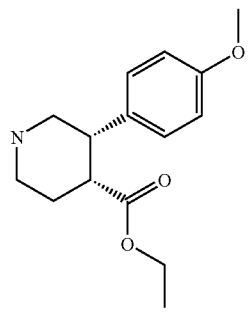

In analogy to the procedure described for the synthesis of (3SR,4RS)-3-(3,4-Difluoro-phenyl)-piperidine-4-carboxylic acid ethyl ester the title compound was prepared from 1-Benzyl-5-(4-methoxy-phenyl)-1,2,3,6-tetrahydro-pyridine-4-carboxylic acid ethyl ester through hydrogenation over Pd/C as colorless viscous oil. MS (m/e): 264.1 [(M+H)⁺].

c) (3SR,4RS)-3-(4-Methoxy-phenyl)-piperidine-1,4-dicarboxylic acid 1-tert-butyl ester 4-ethyl ester

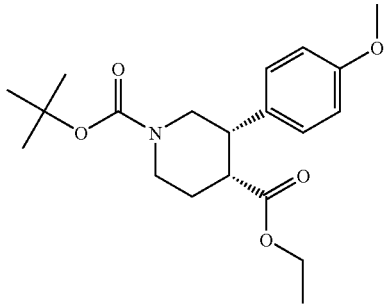

In analogy to the procedure described for the synthesis of (3SR,4RS)-3-(3,4-Difluoro-phenyl)-piperidine-1,4-dicarboxylic acid 1-tert-butyl ester 4-ethyl ester the title compound was prepared from (3SR,4RS)-3-(4-Methoxy-phenyl)-piperidine-4-carboxylic acid ethyl ester and di-tert.-butyl-dicarbonate and catalytic amount DMAP as colorless viscous oil. MS (m/e): 264.1 [(M+H-Boc)⁺].

d) 3-(4-Methoxy-phenyl)-piperidine-1,4-dicarboxylic acid 1-tert-butyl ester 4-ethyl ester

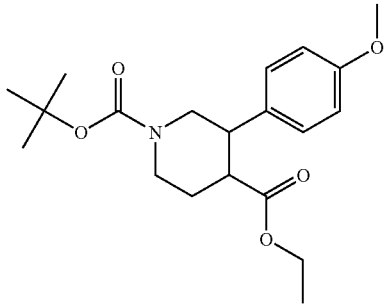

In analogy to the procedure described for the synthesis of (3SR,4SR)-3-(3,4-Difluoro-phenyl)-piperidine-1,4-dicarboxylic acid 1-tert-butyl ester 4-methyl ester the title compound was prepared from (3SR,4RS)-3-(4-Methoxy-phenyl)-piperidine-1,4-dicarboxylic acid 1-tert-butyl ester 4-ethyl ester through epimerization with NaOEt in ethanol as a 1:1 mixture cis:trans as colorless viscous oil. MS (m/e): 264.1 [(M+H-Boc)⁺].

e) 4-Hydroxymethyl-3-(4-methoxy-phenyl)-piperidine-1-carboxylic acid tert-butyl ester

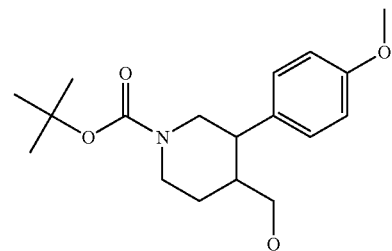

In analogy to the procedure described for the synthesis of (3SR,4SR)-3-(3,4-Difluoro-phenyl)-4-hydroxymethyl-piperidine-1-carboxylic acid tert-butyl ester the title compound was prepared from 3-(4-Methoxy-phenyl)-piperidine-1,4-dicarboxylic acid 1-tert-butyl ester 4-ethyl ester through reduction as colorless viscous oil (1:1 mixture cis:trans). MS (m/e): 222.1 [(M+H-Boc)⁺].

f) 4-(5-Chloro-pyridin-2-yloxymethyl)-3-(4-methoxy-phenyl)-piperidine-1-carboxylic acid tert-butyl ester

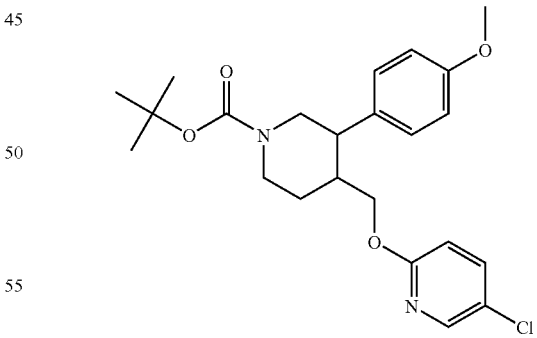

In analogy to the procedure described for the synthesis of (3SR,4SR)-4-(5-Chloro-pyridin-2-yloxymethyl)-3-(3,4-difluoro-phenyl)-piperidine-1-carboxylic acid tert-butyl ester the title compound was prepared through Mitsunobu reaction of 4-Hydroxymethyl-3-(4-methoxy-phenyl)-piperidine-1-carboxylic acid tert-butyl ester with 5-chloro-2-hydroxy pyridine as colorless viscous oil (1:1 mixture cis:trans). MS (m/e): 433.2 [(M+H)⁺].

g) 5-Chloro-2-[3-(4-methoxy-phenyl)-piperidin-4-ylmethoxy]-pyridine, hydrochloride

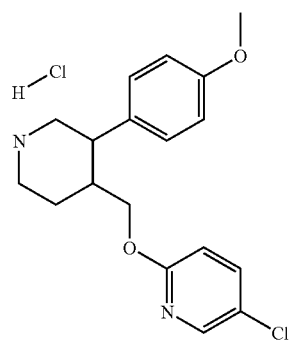

In analogy to the procedure described for the synthesis of 5-Chloro-2-[(3SR,4SR)-3-(3,4-difluoro-phenyl)-piperidin-4-ylmethoxy]-pyridine; hydrochloride the title compound was prepared from 445-Chloro-pyridin-2-yloxymethyl)-3-(4-methoxy-phenyl)-piperidine-1-carboxylic acid tert-butyl ester as off-white foam (1:1 mixture cis:trans). MS (m/e): 333.4 [(M+H)$^+$].

h) [4-(5-Chloro-pyridin-2-yloxymethyl)-3-(4-methoxy-phenyl)-piperidin-1-yl]-[1-(1-methyl-cyclopropanecarbonyl)-piperidin-4-yl]-methanone In analogy to the procedure described for the synthesis of [(3RS, 4RS)-3-(4-chloro-phenyl)-4-(5-chloro-pyridin-2-yloxymethyl)-piperidin-1-yl]-[4-(3-methyl-[1,2,4]oxadiazol-5-yl)-phenyl]-methanone (example 1, step i) the title compound was prepared from 5-Chloro-2-[3-(4-methoxy-phenyl)-piperidin-4-ylmethoxy]-pyridine, hydrochloride and 1-(1-methyl-cyclopropanecarbonyl)-piperidine-4-carboxylic acid (commercially available) as off-white solid (1:1 mixture cis:trans). MS (m/e): 526.4 [(M+H)$^+$].

Example 41

[4-(5-Chloro-pyridin-2-yloxymethyl)-3-(4-methoxy-phenyl)-piperidin-1-yl]-[4-(3-methyl-[1,2,4]oxadiazol-5-yl)-phenyl]-methanone

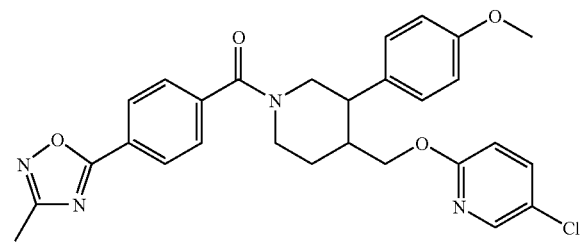

In analogy to the procedure described for the synthesis of [(3RS, 4RS)-3-(4-chloro-phenyl)-4-(5-chloro-pyridin-2-yloxymethyl)-piperidin-1-yl]-[4-(3-methyl-[1,2,4]oxadiazol-5-yl)-phenyl]-methanone (example 1, step i) the title compound was prepared from 5-Chloro-2-[3-(4-methoxy-phenyl)-piperidin-4-ylmethoxy]-pyridine, hydrochloride and 4-(3-Methyl-[1,2,4]oxadiazol-5-yl)-benzoic acid (commercially available) as off-white solid (1:1 mixture cis:trans). MS (m/e): 519.3 [(M+H)$^+$].

Example 42

4-[4-(5-Chloro-pyridin-2-yloxymethyl)-3-(4-methoxy-phenyl)-piperidine-1-carbonyl]-3,4,5,6-tetrahydro-2H-[1,2']bipyridinyl-5'-carbonitrile

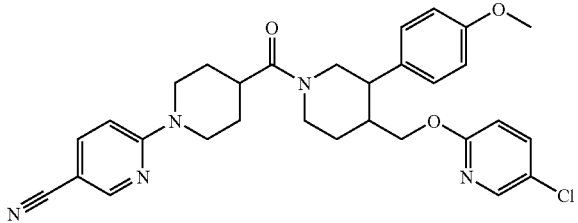

In analogy to the procedure described for the synthesis of [(3RS, 4RS)-3-(4-chloro-phenyl)-4-(5-chloro-pyridin-2-yloxymethyl)-piperidin-1-yl]-[4-(3-methyl-[1,2,4]oxadiazol-5-yl)-phenyl]-methanone (example 1, step i) the title compound was prepared from 5-Chloro-2-[3-(4-methoxy-phenyl)-piperidin-4-ylmethoxy]-pyridine, hydrochloride and 5'-Cyano-3,4,5,6-tetrahydro-2H-[1,2']bipyridinyl-4-carboxylic acid (commercially available) as off-white solid (1:1 mixture cis:trans). MS (m/e): 546.2 [(M+H)$^+$].

Example 43

[4-(5-Chloro-pyridin-2-yloxymethyl)-3-(4-methoxy-phenyl)-piperidin-1-yl]-(4-methanesulfonyl-piperazin-1-yl)-methanone

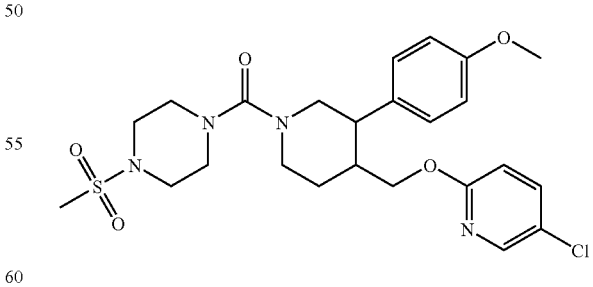

In analogy to the procedure described for the synthesis of [(3RS, 4RS)-3-(4-chloro-phenyl)-4-(5-chloro-pyridin-2-yloxymethyl)-piperidin-1-yl]-[4-(3-methyl-[1,2,4]oxadiazol-5-yl)-phenyl]-methanone (example 1, step i) the title compound was prepared from 5-Chloro-2-[3-(4-methoxy-phenyl)-piperidin-4-ylmethoxy]-pyridine, hydrochloride and 4-Methanesulfonyl-piperazine-1-carbonyl chloride (WO2009024502) as off-white solid (1:1 mixture cis:trans). MS (m/e): 523.5 [(M+H)⁺].

Example 44

[(3SR,4SR)-4-(5-Chloro-pyridin-2-yloxymethyl)-3-phenyl-piperidin-1-yl]-[1-(1-methyl-cyclopropanecarbonyl)-piperidin-4-yl]-methanone

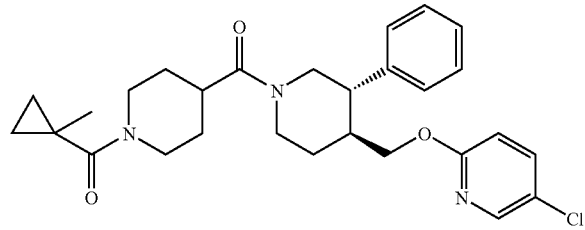

a) (3SR,4RS)-3-Phenyl-piperidine-4-carboxylic acid ethyl ester

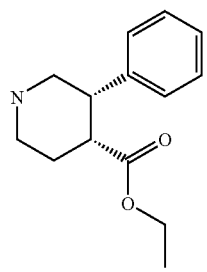

In analogy to the procedure described for the synthesis of (3SR,4RS)-3-(3,4-Difluoro-phenyl)-piperidine-4-carboxylic acid ethyl ester the title compound was prepared from 1-Benzyl-5-phenyl-1,2,3,6-tetrahydro-pyridine-4-carboxylic acid ethyl ester ((Bioorganic & Medicinal Chemistry Letters 2003, 2513-2518) through hydrogenation over Pd/C as colorless viscous oil. MS (m/e): 234.1 [(M+H)⁺].

b) (3SR,4RS)-3-Phenyl-piperidine-1,4-dicarboxylic acid 1-tert-butyl ester 4-ethyl ester

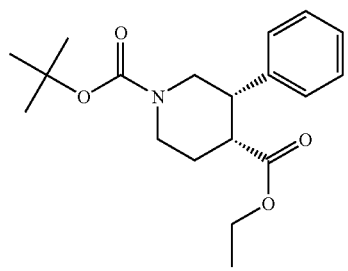

In analogy to the procedure described for the synthesis of (3SR,4RS)-3-(3,4-Difluoro-phenyl)-piperidine-1,4-dicarboxylic acid 1-tert-butyl ester 4-ethyl ester the title compound was prepared from (3SR,4RS)-3-Phenyl-piperidine-4-carboxylic acid ethyl ester and di-tert.-butyl-dicarbonate and catalytic amount DMAP as colorless viscous oil. MS (m/e): 234.1 [(M+H-Boc)⁺].

c) (3SR,4SR)-3-Phenyl-piperidine-1,4-dicarboxylic acid 1-tert-butyl ester 4-ethyl ester

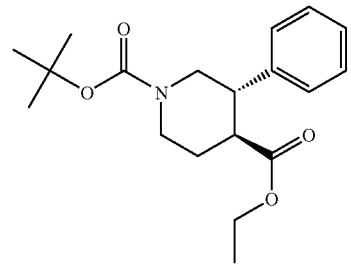

In analogy to the procedure described for the synthesis of (3SR,4SR)-3-(3,4-Difluoro-phenyl)-piperidine-1,4-dicarboxylic acid 1-tert-butyl ester 4-methyl ester the title compound was prepared from (3SR,4RS)-3-Phenyl-piperidine-1,4-dicarboxylic acid 1-tert-butyl ester 4-ethyl ester through epimerization with NaOEt in ethanol as white solid. MS (m/e): 234.1 [(M+H-Boc)⁺].

d) (3SR,4SR)-4-Hydroxymethyl-3-phenyl-piperidine-1-carboxylic acid tert-butyl ester

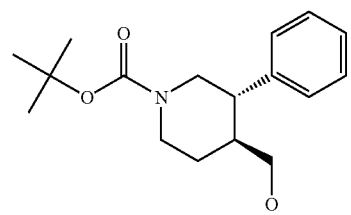

In analogy to the procedure described for the synthesis of (3SR,4SR)-3-(3,4-Difluoro-phenyl)-4-hydroxymethyl-piperidine-1-carboxylic acid tert-butyl ester the title compound was prepared from) (3SR,4SR)-3-Phenyl-piperidine-1,4-dicarboxylic acid 1-tert-butyl ester 4-ethyl ester through reduction as colorless viscous oil. MS (m/e): 314.0 [(M+Na)⁺].

e) (3SR,4SR)-4-(5-Chloro-pyridin-2-yloxymethyl)-3-phenyl-piperidine-1-carboxylic acid tert-butyl ester

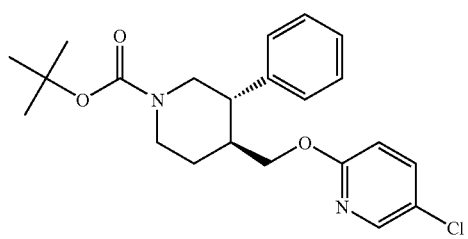

In analogy to the procedure described for the synthesis of (3SR,4SR)-4-(5-Chloro-pyridin-2-yloxymethyl)-3-(3,4-difluoro-phenyl)-piperidine-1-carboxylic acid tert-butyl ester the title compound was prepared through Mitsunobu reaction of (3SR,4SR)-4-Hydroxymethyl-3-phenyl-piperidine-1-carboxylic acid tert-butyl ester with 5-chloro-2-hydroxy pyridine as colorless viscous oil. MS (m/e): 403.2 [(M+H)+].

f) 5-Chloro-2-((3S,4S)-3-phenyl-piperidin-4-yl-methoxy)-pyridine, hydrochloride

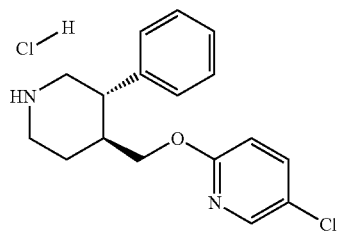

In analogy to the procedure described for the synthesis of 5-Chloro-2-[(3SR,4SR)-3-(3,4-difluoro-phenyl)-piperidin-4-ylmethoxy]-pyridine; hydrochloride the title compound was prepared from (3SR,4 SR)-4-(5-Chloro-pyridin-2-yloxymethyl)-3-phenyl-piperidine-1-carboxylic acid tert-butyl ester as off-white foam. MS (m/e): 303.3 [(M+H)+].

g) [(3SR,4SR)-4-(5-Chloro-pyridin-2-yloxymethyl)-3-phenyl-piperidin-1-yl]-[1-(1-methyl-cyclopropanecarbonyl)-piperidin-4-yl]-methanone In analogy to the procedure described for the synthesis of [(3RS, 4RS)-3-(4-chloro-phenyl)-4-(5-chloro-pyridin-2-yloxymethyl)-piperidin-1-yl]-[4-(3-methyl-[1,2,4]oxadiazol-5-yl)-phenyl]-methanone (example 1, step i) the title compound was prepared from 5-Chloro-2-((3S,4S)-3-phenyl-piperidin-4-ylmethoxy)-pyridine, hydrochloride and 1-(1-methyl-cyclopropanecarbonyl)-piperidine-4-carboxylic acid (commercially available) as off-white solid. MS (m/e): 496.4 [(M+H)+].

Example 45

[(3SR,4SR)-4-(5-Chloro-pyridin-2-yloxymethyl)-3-phenyl-piperidin-1-yl]-(6-methyl-pyridazin-4-yl)-methanone

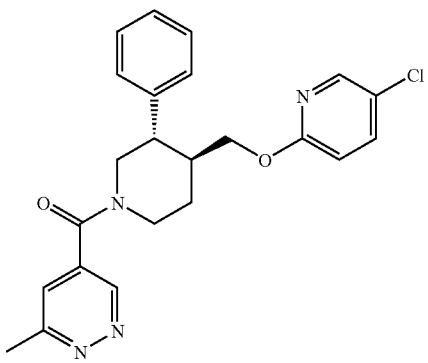

In analogy to the procedure described for the synthesis of [(3RS, 4RS)-3-(4-chloro-phenyl)-4-(5-chloro-pyridin-2-yloxymethyl)-piperidin-1-yl]-[4-(3-methyl-[1,2,4]oxadiazol-5-yl)-phenyl]-methanone (example 1, step i) the title compound was prepared from 5-Chloro-2-((3S,4S)-3-phenyl-piperidin-4-ylmethoxy)-pyridine, hydrochloride and 6-Methyl-pyridazine-4-carboxylic acid (WO2009019163) as off-white solid. MS (m/e): 423.3 [(M+H)+].

Example 46

[(3SR,4SR)-4-(5-Chloro-pyridin-2-yloxymethyl)-3-phenyl-piperidin-1-yl]-[4-(3-methyl-[1,2,4]oxadiazol-5-yl)-phenyl]-methanone

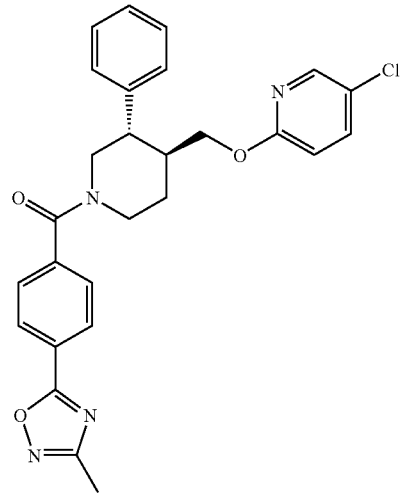

In analogy to the procedure described for the synthesis of [(3RS, 4RS)-3-(4-chloro-phenyl)-4-(5-chloro-pyridin-2-yloxymethyl)-piperidin-1-yl]-[4-(3-methyl-[1,2,4]oxadiazol-5-yl)-phenyl]-methanone (example 1, step i) the title compound was prepared from 5-Chloro-2-((3S,4S)-3-phenyl-piperidin-4-ylmethoxy)-pyridine, hydrochloride and 4-(3-M ethyl-[1,2,4]oxadiazol-5-yl)-benzoic acid (commercially available) as off-white solid. MS (m/e): 489.3 [(M+H)+].

Example 47

4-[(3S,4S)-4-(5-Chloro-pyridin-2-yloxymethyl)-3-phenyl-piperidine-1-carbonyl]-3,4,5,6-tetrahydro-2H-[1,2']bipyridinyl-5'-carbonitrile

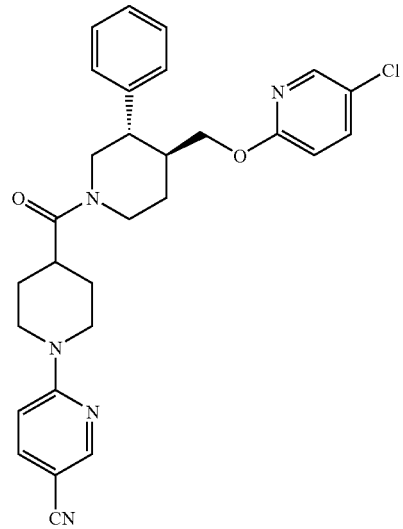

In analogy to the procedure described for the synthesis of [(3RS, 4RS)-3-(4-chloro-phenyl)-4-(5-chloro-pyridin-2- yloxymethyl)-piperidin-1-yl]-[4-(3-methyl-[1,2,4]oxadiazol-5-yl)-phenyl]-methanone (example 1, step i) the title compound was prepared from 5-Chloro-2-((3S,4S)-3-phenyl-piperidin-4-ylmethoxy)-pyridine, hydrochloride and 5'-Cyano-3,4,5,6-tetrahydro-2H-[1,2']bipyridinyl-4-carboxylic acid (commercially available) as off-white solid. MS (m/e): 516.4 [(M+H)⁺].

Example 48

[(3S,4S)-4-(5-Chloro-pyridin-2-yloxymethyl)-3-phenyl-piperidin-1-yl]-(4-methanesulfonyl-piperazin-1-yl)-methanone

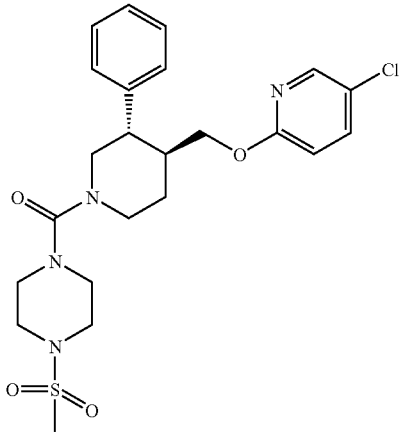

In analogy to the procedure described for the synthesis of [(3RS, 4RS)-3-(4-chloro-phenyl)-4-(5-chloro-pyridin-2-yloxymethyl)-piperidin-1-yl]-[4-(3-methyl-[1,2,4]oxadiazol-5-yl)-phenyl]-methanone (example 1, step i) the title compound was prepared from 5-Chloro-2-((3S,4S)-3-phenyl-piperidin-4-ylmethoxy)-pyridine, hydrochloride and 4-Methanesulfonyl-piperazine-1-carbonyl chloride (WO2009024502) as off-white solid. MS (m/e): 493.2 [(M+H)⁺].

Example 49

4-{(3S,4S)-3-(4-Chloro-phenyl)-4-[(S)-1-(3,4-dichloro-phenoxy)-ethyl]-piperidine-1-carbonyl}-3,4,5,6-tetrahydro-2H-[1,2']bipyridinyl-5'-carbonitrile

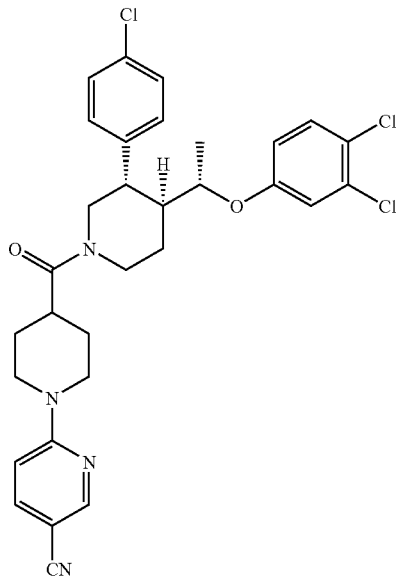

a) (3S,4S)-3-(4-Chloro-phenyl)-4-[(S)-1-(3,4-dichloro-phenoxy)-ethyl]-piperidine

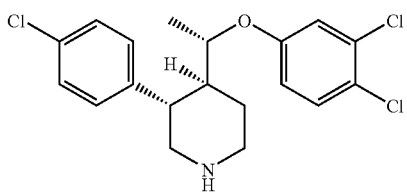

In analogy to the procedure described for the synthesis of 2-{(SR)-1-[(3SR,4SR)-1-Benzyl-3-(4-chloro-phenyl)-piperidin-4-yl]-ethoxy}-5-chloro-pyridine the title compound was prepared from (R)-1-[(3S,4S)-1-Benzyl-3-(4-chlorophenyl)-piperidin-4-yl]-ethanol and 3,4-Dichloro-phenol followed by removal of the benzyl protecting group by treatment with 1-chloroethyl-chloroformate, DIPEA and methanol and used without further purification in the subsequent step.

b) 4-{(3S,4S)-3-(4-Chloro-phenyl)-4-[(S)-1-(3,4-dichloro-phenoxy)-ethyl]-piperidine-1-carbonyl}-3,4,5,6-tetrahydro-2H-[1,2']bipyridinyl-5'-carbonitrile In analogy to the procedure described for the synthesis of [(3RS, 4RS)-3-(4-chloro-phenyl)-4-(5-chloro-pyridin-2-yloxymethyl)-piperidin-1-yl]-[4-(3-methyl-[1,2,4]oxadiazol-5-yl)-phenyl]-methanone (example 1, step i) the title compound was prepared from (3S,4S)-3-(4-Chloro-phenyl)-4-[(S)-1-(3,4-dichloro-phenoxy)-ethyl]-piperidine and 5'-Cyano-3,4,5,6-tetrahydro-2H-[1,2']bipyridinyl-4-carboxylic acid (commercially available) as viscous yellow oil. MS (m/e): 597.4 [(M+H)⁺].

Example 50

4-{(3S,4S)-3-(4-Chloro-phenyl)-4-[(S)-1-(4-trifluoromethyl-phenoxy)-ethyl]-piperidine-1-carbonyl}-3,4,5,6-tetrahydro-2H-[1,2']bipyridinyl-5'-carbonitrile

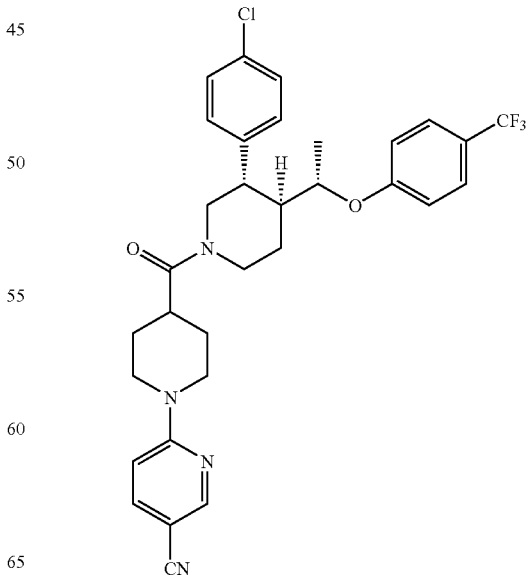

In analogy to the procedure described for the synthesis of 4-{(3S,4S)-3-(4-Chloro-phenyl)-4-[(S)-1-(3,4-dichloro-phenoxy)-ethyl]-piperidine-1-carbonyl}-3,4,5,6-tetrahydro-2H-[1,2']bipyridinyl-5'-carbonitrile (example 49) the respective piperidine derivative was prepared from (R)-1-[(3S,4S)-1-Benzyl-3-(4-chloro-phenyl)-piperidin-4-yl]-ethanol and 4-trifluoromethyl-phenol via Mitsunobu reaction and subsequently the benzyl group was cleaved by treatment with 1-chloroethyl-chloroformate, DIPEA and methanol. Coupling with 5'-Cyano-3,4,5,6-tetrahydro-2H-[1,2']bipyridinyl-4-carboxylic acid (commercially available) yielded the title compound as viscous yellow oil. MS (m/e): 597.4 [(M+H)+].

Example 51

4-{(3S,4S)-3-(4-Chloro-phenyl)-4-[(S)-1-(4-cyano-phenoxy)-ethyl]-piperidine-1-carbonyl}-3,4,5,6-tetrahydro-2H-[1,2']bipyridinyl-5'-carbonitrile

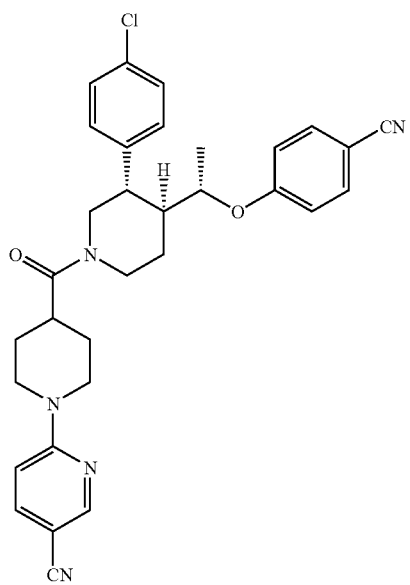

In analogy to the procedure described for the synthesis of 4-{(3S,4S)-3-(4-Chloro-phenyl)-4-[(S)-1-(3,4-dichloro-phenoxy)-ethyl]-piperidine-1-carbonyl}-3,4,5,6-tetrahydro-2H-[1,2']bipyridinyl-5'-carbonitrile (example 49) the respective piperidine derivative was prepared from (R)-1-[(3S,4S)-1-Benzyl-3-(4-chloro-phenyl)-piperidin-4-yl]-ethanol and 4-cyano-phenol via Mitsunobu reaction and subsequently the benzyl group was cleaved by treatment with 1-chloroethyl-chloroformate, DIPEA and methanol. Coupling with 5'-Cyano-3,4,5,6-tetrahydro-2H-[1,2']bipyridinyl-4-carboxylic acid (commercially available) yielded the title compound as viscous yellow oil. MS (m/e): 554.3 [(M+H)+].

Example 52

4-{(3S,4S)-3-(4-Chloro-phenyl)-4-[(S)-1-(5-fluoro-pyridin-2-yloxy)-ethyl]-piperidine-1-carbonyl}-3,4,5,6-tetrahydro-2H-[1,2']bipyridinyl-5'-carbonitrile

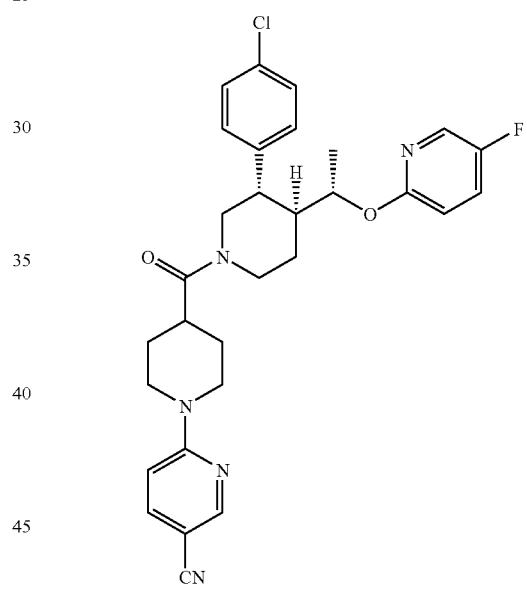

In analogy to the procedure described for the synthesis of 4-{(3S,4S)-3-(4-Chloro-phenyl)-4-[(S)-1-(3,4-dichloro-phenoxy)-ethyl]-piperidine-1-carbonyl}-3,4,5,6-tetrahydro-2H-[1,2']bipyridinyl-5'-carbonitrile (example 49) the respective piperidine derivative was prepared from (R)-1-[(3S,4S)-1-Benzyl-3-(4-chloro-phenyl)-piperidin-4-yl]-ethanol and 5-fluoro-2-hydroxy pyridine via Mitsunobu reaction and subsequently the benzyl group was cleaved by treatment with 1-chloroethyl-chloroformate, DIPEA and methanol. Coupling with 5'-Cyano-3,4,5,6-tetrahydro-2H-[1,2']bipyridinyl-4-carboxylic acid (commercially available) yielded the title compound as viscous yellow oil. MS (m/e): 548.4 [(M+H)+].

Example 53

4-{(3S,4S)-3-(4-Chloro-phenyl)-4-[(S)-1-(4-fluoro-phenoxy)-ethyl]-piperidine-1-carbonyl}-3,4,5,6-tetrahydro-2H-[1,2']bipyridinyl-5'-carbonitrile

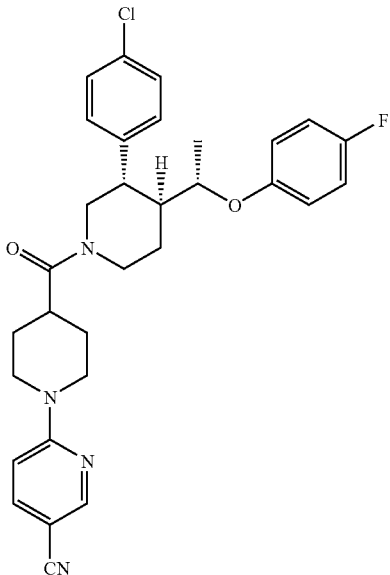

In analogy to the procedure described for the synthesis of 4-{(3S,4S)-3-(4-Chloro-phenyl)-4-[(S)-1-(3,4-dichloro-phenoxy)-ethyl]-piperidine-1-carbonyl}-3,4,5,6-tetrahydro-2H-[1,2']bipyridinyl-5'-carbonitrile (example 49) the respective piperidine derivative was prepared from (R)-1-[(3S,4S)-1-Benzyl-3-(4-chloro-phenyl)-piperidin-4-yl]-ethanol and 4-fluoro-phenol via Mitsunobu reaction and subsequently the benzyl group was cleaved by treatment with 1-chloroethyl-chloroformate, DIPEA and methanol. Coupling with 5'-Cyano-3,4,5,6-tetrahydro-2H-[1,2']bipyridinyl-4-carboxylic acid (commercially available) yielded the title compound as off-white foam. MS (m/e): 547.3 [(M+H)$^+$].

Example 54

4-{(3S,4S)-3-(4-Chloro-phenyl)-4-[(S)-1-(3,4-difluoro-phenoxy)-ethyl]-piperidine-1-carbonyl}-3,4,5,6-tetrahydro-2H-[1,2']bipyridinyl-5'-carbonitrile

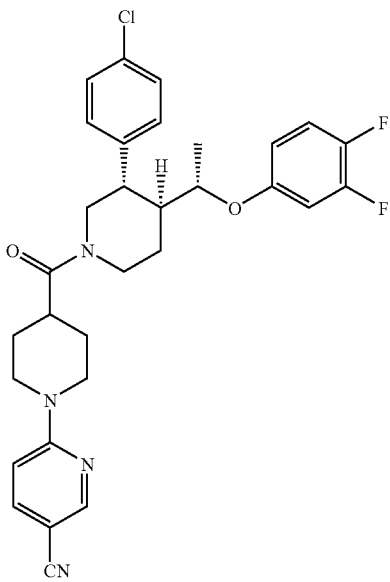

In analogy to the procedure described for the synthesis of 4-{(3S,4S)-3-(4-Chloro-phenyl)-4-[(S)-1-(3,4-dichloro-phenoxy)-ethyl]-piperidine-1-carbonyl}-3,4,5,6-tetrahydro-2H-[1,2']bipyridinyl-5'-carbonitrile (example 49) the respective piperidine derivative was prepared from (R)-1-[(3S,4S)-1-Benzyl-3-(4-chloro-phenyl)-piperidin-4-yl]-ethanol and 3,4-difluoro-phenol via Mitsunobu reaction and subsequently the benzyl group was cleaved by treatment with 1-chloroethyl-chloroformate, DIPEA and methanol. Coupling with 5'-Cyano-3,4,5,6-tetrahydro-2H-[1,2']bipyridinyl-4-carboxylic acid (commercially available) yielded the title compound as yellow foam. MS (m/e): 565.4 [(M+H)$^+$].

Example 55

4-[(3S,4S)-4-[(S)-1-(4-Chloro-phenoxy)-ethyl]-3-(4-chloro-phenyl)-piperidine-1-carbonyl]-3,4,5,6-tetrahydro-2H-[1,2']bipyridinyl-5'-carbonitrile

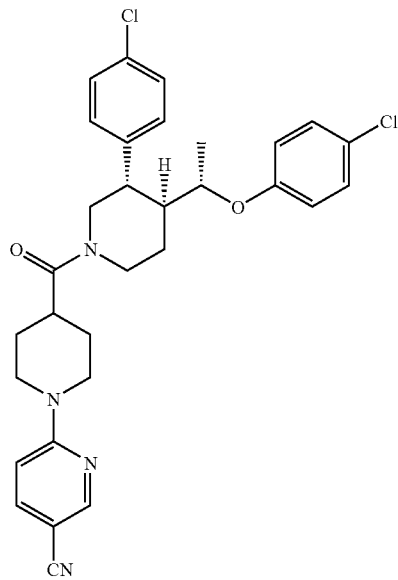

In analogy to the procedure described for the synthesis of 4-{(3S,4S)-3-(4-Chloro-phenyl)-4-[(S)-1-(3,4-dichloro-phenoxy)-ethyl]-piperidine-1-carbonyl}-3,4,5,6-tetrahydro-2H-[1,2']bipyridinyl-5'-carbonitrile (example 49) the respective piperidine derivative was prepared from (R)-1-[(3S,4S)-1-Benzyl-3-(4-chloro-phenyl)-piperidin-4-yl]-ethanol and 4-chloro-phenol via Mitsunobu reaction and subsequently the benzyl group was cleaved by treatment with 1-chloroethyl-chloroformate, DIPEA and methanol. Coupling with 5'-Cyano-3,4,5,6-tetrahydro-2H-[1,2']bipyridinyl-4-carboxylic acid (commercially available) yielded the title compound as viscous yellow oil. MS (m/e): 565.6 [(M+H)$^+$].

Example 56

4-{(3S,4S)-3-(4-Chloro-phenyl)-4-[(S)-1-(3-fluoro-phenoxy)-ethyl]-piperidine-1-carbonyl}-3,4,5,6-tetrahydro-2H-[1,2']bipyridinyl-5'-carbonitrile

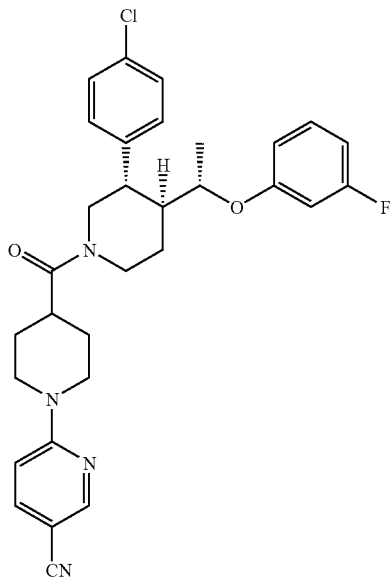

In analogy to the procedure described for the synthesis of 4-{(3S,4S)-3-(4-Chloro-phenyl)-4-[(S)-1-(3,4-dichloro-phenoxy)-ethyl]-piperidine-1-carbonyl}-3,4,5,6-tetrahydro-2H-[1,2']bipyridinyl-5'-carbonitrile (example 49) the respective piperidine derivative was prepared from (R)-1-[(3S,4S)-1-Benzyl-3-(4-chloro-phenyl)-piperidin-4-yl]-ethanol and 3-fluoro-phenol via Mitsunobu reaction and subsequently the benzyl group was cleaved by treatment with 1-chloroethyl-chloroformate, DIPEA and methanol. Coupling with 5'-Cyano-3,4,5,6-tetrahydro-2H-[1,2']bipyridinyl-4-carboxylic acid (commercially available) yielded the title compound as viscous yellow oil. MS (m/e): 547.4 [(M+H)$^+$].

Example 57

4-[(3S,4S)-3-(4-Chloro-phenyl)-4-((S)-1-p-tolyloxy-ethyl)-piperidine-1-carbonyl]-3,4,5,6-tetrahydro-2H-[1,2']bipyridinyl-5'-carbonitrile

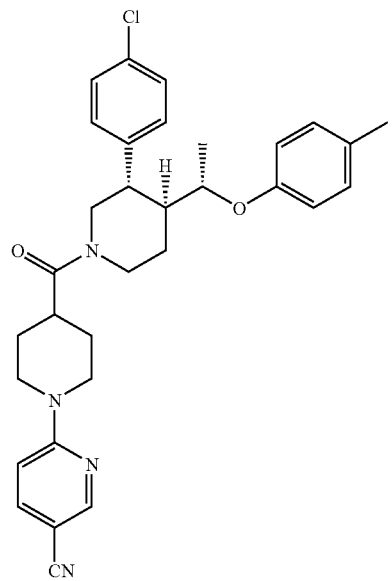

In analogy to the procedure described for the synthesis of 4-{(3S,4S)-3-(4-Chloro-phenyl)-4-[(S)-1-(3,4-dichloro-phenoxy)-ethyl]-piperidine-1-carbonyl}-3,4,5,6-tetrahydro-2H-[1,2']bipyridinyl-5'-carbonitrile (example 49) the respective piperidine derivative was prepared from (R)-1-[(3S,4S)-1-Benzyl-3-(4-chloro-phenyl)-piperidin-4-yl]-ethanol and 4-methyl-phenol via Mitsunobu reaction and subsequently the benzyl group was cleaved by treatment with 1-chloroethyl-chloroformate, DIPEA and methanol. Coupling with 5'-Cyano-3,4,5,6-tetrahydro-2H-[1,2']bipyridinyl-4-carboxylic acid (commercially available) yielded the title compound as viscous yellow oil. MS (m/e): 543.5 [(M+H)$^+$].

Example 58

4-{(3S,4S)-3-(4-Chloro-phenyl)-4-[(S)-1-(5-methyl-pyridin-2-yloxy)-ethyl]piperidine-1-carbonyl}-3,4,5,6-tetrahydro-2H-[1,2']bipyridinyl-5'-carbonitrile

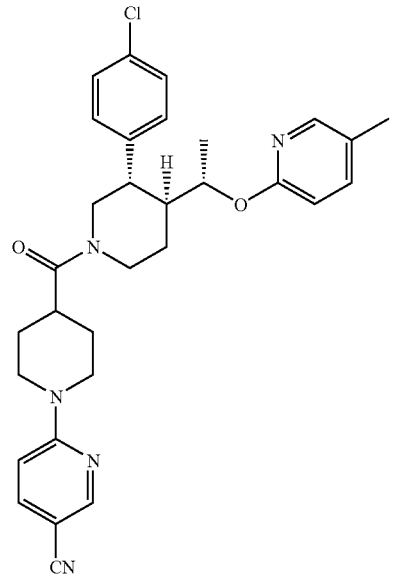

In analogy to the procedure described for the synthesis of 4-{(3S,4S)-3-(4-Chloro-phenyl)-4-[(S)-1-(3,4-dichloro-phenoxy)-ethyl]-piperidine-1-carbonyl}-3,4,5,6-tetrahydro-2H-[1,2']bipyridinyl-5'-carbonitrile (example 49) the respective piperidine derivative was prepared from (R)-1-[(3S,4S)-1-Benzyl-3-(4-chloro-phenyl)-piperidin-4-yl]-ethanol and 5-methyl-pyridin-2-ol via Mitsunobu reaction and subsequently the benzyl group was cleaved by treatment with 1-chloroethyl-chloroformate, DIPEA and methanol. Coupling with 5'-Cyano-3,4,5,6-tetrahydro-2H-[1,2']bipyridinyl-4-carboxylic acid (commercially available) yielded the title compound as viscous light yellow oil. MS (m/e): 544.4 [(M+H)$^+$].

Example 59

4-{(3S,4S)-3-(4-Chloro-phenyl)-4-[(S)-1-(1H-indol-5-yloxy)-ethyl]-piperidine-1-carbonyl}-3,4,5,6-tetrahydro-2H-[1,2']bipyridinyl-5'-carbonitrile

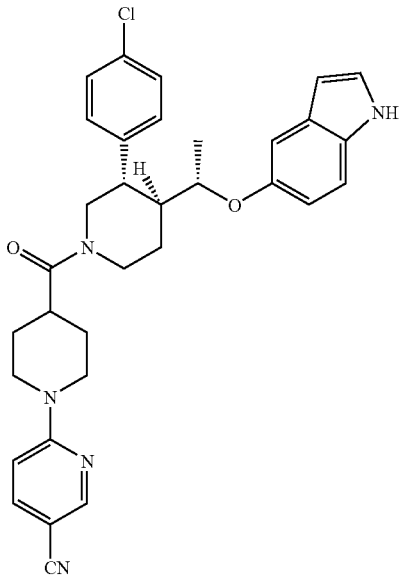

In analogy to the procedure described for the synthesis of 4-{(3S,4S)-3-(4-Chloro-phenyl)-4-[(S)-1-(3,4-dichloro-phenoxy)-ethyl]-piperidine-1-carbonyl}-3,4,5,6-tetrahydro-2H-[1,2']bipyridinyl-5'-carbonitrile (example 49) the respective piperidine derivative was prepared from (R)-1-[(3S,4S)-1-Benzyl-3-(4-chloro-phenyl)-piperidin-4-yl]-ethanol and 1H-indol-5-ol via Mitsunobu reaction and subsequently the benzyl group was cleaved by treatment with 1-chloroethyl-chloroformate, DIPEA and methanol. Coupling with 5'-Cyano-3,4,5,6-tetrahydro-2H-[1,2']bipyridinyl-4-carboxylic acid (commercially available) yielded the title compound as viscous yellow oil. MS (m/e): 568.3 [(M+H)+].

Example 60

4-[(3S,4S)-4-[(S)-1-(4-Chloro-3-fluoro-phenoxy)-ethyl]-3-(4-chloro-phenyl)-piperidine-1-carbonyl]-3,4,5,6-tetrahydro-2H-[1,2']bipyridinyl-5'-carbonitrile

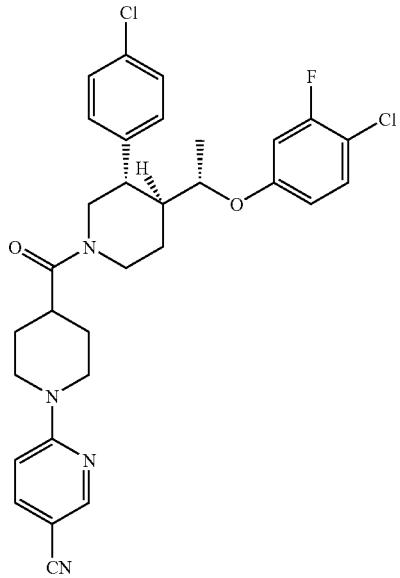

In analogy to the procedure described for the synthesis of 4-{(3S,4S)-3-(4-Chloro-phenyl)-4-[(S)-1-(3,4-dichloro-phenoxy)-ethyl]-piperidine-1-carbonyl}-3,4,5,6-tetrahydro-2H-[1,2']bipyridinyl-5'-carbonitrile (example 49) the respective piperidine derivative was prepared from (R)-1-[(3S,4S)-1-Benzyl-3-(4-chloro-phenyl)-piperidin-4-yl]-ethanol and 4-Chloro-3-fluoro-phenol via Mitsunobu reaction and subsequently the benzyl group was cleaved by treatment with 1-chloroethyl-chloroformate, DIPEA and methanol. Coupling with 5'-Cyano-3,4,5,6-tetrahydro-2H-[1,2']bipyridinyl-4-carboxylic acid (commercially available) yielded the title compound as viscous yellow oil. MS (m/e): 581.5 [(M+H)+].

Example 61

4-{(3S,4S)-3-(4-Chloro-phenyl)-4-[(S)-1-(5-fluoro-pyrimidin-2-yloxy)-ethyl]-piperidine-1-carbonyl}-3,4,5,6-tetrahydro-2H-[1,2']bipyridinyl-5'-carbonitrile

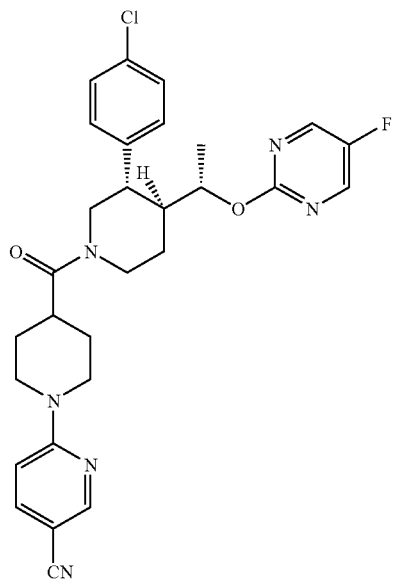

In analogy to the procedure described for the synthesis of 4-{(3S,4S)-3-(4-Chloro-phenyl)-4-[(S)-1-(3,4-dichloro-phenoxy)-ethyl]-piperidine-1-carbonyl}-3,4,5,6-tetrahydro-2H-[1,2']bipyridinyl-5'-carbonitrile (example 49) the respective piperidine derivative was prepared from (R)-1-[(3S,4S)-1-Benzyl-3-(4-chloro-phenyl)-piperidin-4-yl]-ethanol and 5-fluoro-pyrimidin-2-ol via Mitsunobu reaction and subsequently the benzyl group was cleaved by treatment with 1-chloroethyl-chloroformate, DIPEA and methanol. Coupling with 5'-Cyano-3,4,5,6-tetrahydro-2H-[1,2']bipyridinyl-4-carboxylic acid (commercially available) yielded the title compound as viscous yellow oil. MS (m/e): 549.4 [(M+H)+].

Example 62

4-[(3S,4S)-4-[(S)-1-(5-Chloro-pyridin-2-yloxy)-ethyl]-3-(3,4-difluoro-phenyl)-piperidine-1-carbonyl]-3,4,5,6-tetrahydro-2H-[1,2']bipyridinyl-5'-carbonitrile

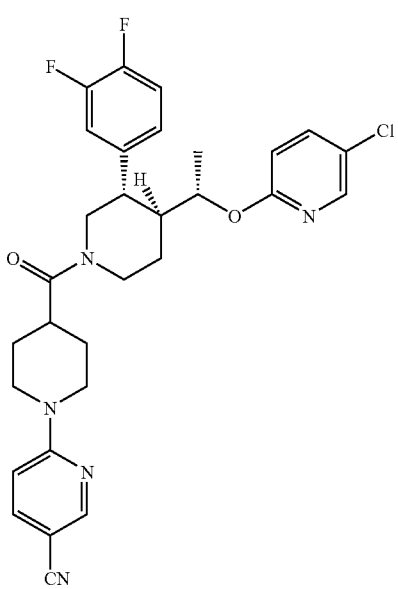

a) 1-Benzyl-5-(3,4-difluoro-phenyl)-1,2,3,6-tetrahydro-pyridine-4-carboxylic acid, hydrochloride

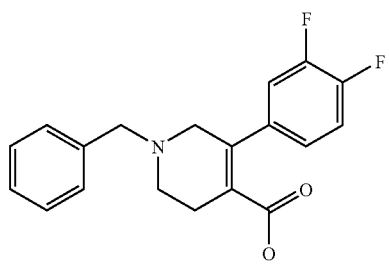

In analogy to the procedure described for the synthesis of 1-Benzyl-5-(4-chloro-phenyl)-1,2,3,6-tetrahydro-pyridine-4-carboxylic acid the title compound was prepared from 1-Benzyl-5-(3,4-difluoro-phenyl)-1,2,3,6-tetrahydro-pyridine-4-carboxylic acid ethyl ester through saponificatin with LiOH.H$_2$O and subsequent formation of the salt with HCl in diethyl ether. MS (m/e): 330.1 [(M+H)$^+$].

b) (3S,4R)-1-Benzyl-3-(3,4-difluoro-phenyl)-piperidine-4-carboxylic acid

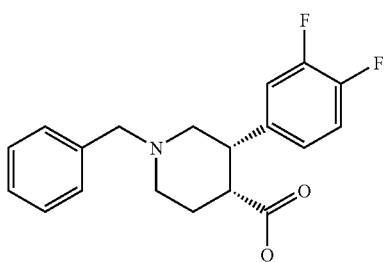

In analogy to the synthesis of (3RS, 4SR)-1-Benzyl-3-(4-chloro-phenyl)-piperidine-4-carboxylic acid (example 1 (c)) the title compound was prepared through hydrogenation of 1-Benzyl-5-(3,4-difluoro-phenyl)-1,2,3,6-tetrahydro-pyridine-4-carboxylic acid, hydrochloride under Ruthenium catalysis ([Ru(OAc)$_2$((R)-(6,6'-dimethoxybiphenyl-2,2'-diyl)bis(di-2-furylphosphine)]). The title compound was used without further purification in the consecutive step.

c) (3S,4R)-1-Benzyl-3-(3,4-difluoro-phenyl)-piperidine-4-carboxylic acid methoxy-methyl-amide In analogy to the procedure described for the synthesis of (3RS,4SR)-1-Benzyl-3-(4-chloro-phenyl)-piperidine-4-carboxylic acid methoxy-methyl-amide (example 5 (a)) the title compound was prepared from (3S,4R)-1-Benzyl-3-(3,4-difluoro-phenyl)-piperidine-4-carboxylic acid and methoxymethylamine. The title compound was obtained as light brown foam. MS (m/e): 375.4 [(M+H)$^+$].

d) 1-[(3S,4S)-1-Benzyl-3-(3,4-difluoro-phenyl)-piperidin-4-yl]-ethanone

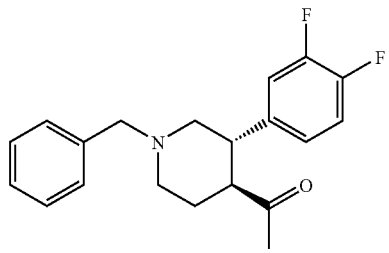

In analogy to the procedure described for the synthesis of 1-[(3SR,4SR)-1-benzyl-3-(4-chloro-phenyl)-piperidin-4-yl]-ethanone (example 5 (c)) the title compound was prepared from (3S,4R)-1-Benzyl-3-(3,4-difluoro-phenyl)-piperidine-4-carboxylic acid methoxy-methyl-amide and methylmagnesium bromide with subsequent epimerisation with NaOMe in methanol. The title compound was obtained as light brown solid. MS (m/e): 330.3 [(M+H)$^+$].

e) (S)-1-[(3S,4S)-1-Benzyl-3-(3,4-difluoro-phenyl)-piperidin-4-yl]-ethanol and (R)-1-[(3S,4S)-1-Benzyl-3-(3,4-difluoro-phenyl)-piperidin-4-yl]-ethanol

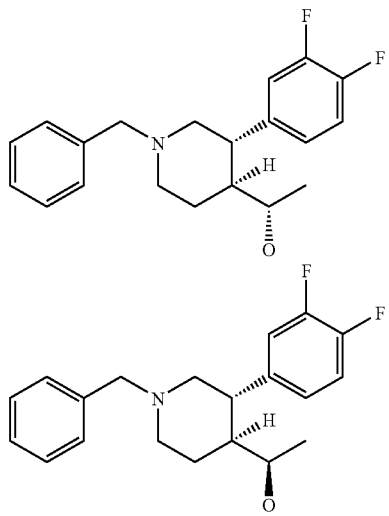

In analogy to the procedure described for the synthesis of (RS)-1-[(3SR,4SR)-1-Benzyl-3-(4-chloro-phenyl)-piperidin-4-yl]-ethanol (example 5 (d)) the title compounds were synthesized from 1-[(3S,4S)-1-Benzyl-3-(3,4-difluoro-phenyl)-piperidin-4-yl]-ethanone through reduction with LiAlH$_4$. (S)-1-[(3S,4S)-1-Benzyl-3-(3,4-difluoro-phenyl)-piperidin-4-yl]-ethanol was obtained as light yellow waxy solid. MS (m/e): 332.1 [(M+H)$^+$] and (R)-1-[(3S,4S)-1-Benzyl-3-(3,4-difluoro-phenyl)-piperidin-4-yl]-ethanol was obtained as light yellow viscous oil. MS (m/e): 332.1 [(M+H)$^+$].

4-[(3S,4S)-4-[(S)-1-(5-Chloro-pyridin-2-yloxy)-ethyl]-3-(3,4-difluoro-phenyl)-piperidine-1-carbonyl]-3,4,5,6-tetrahydro-2H-[1,2]bipyridinyl-5'-carbonitrile In analogy to the procedure described for the synthesis of 4-{(3S,4S)-3-(4-Chloro-phenyl)-4-[(S)-1-(3,4-dichlorophenoxy)-ethyl]-piperidine-1-carbonyl}-3,4,5,6-tetrahydro-2H-[1,2']bipyridinyl-5'-carbonitrile (example 49) the respective piperidine derivative was prepared from (R)-1-[(3S,4S)-1-Benzyl-3-(3,4-difluoro-phenyl)-piperidin-4-yl]-ethanol and 5-Chloro-2-hydroxy-pyridine via Mitsunobu reaction and subsequently the benzyl group was cleaved by treatment with 1-chloroethyl-chloroformate, DIPEA and methanol to yield 5-Chloro-2-{(S)-1-[(3S,4S)-3-(3,4-difluoro-phenyl)-piperidin-4-yl]-ethoxy}-pyridine. Coupling with 5'-Cyano-3,4,5,6-tetrahydro-2H-[1,2']bipyridinyl-4-carboxylic acid (commercially available) yielded the title compound as off-white solid. MS (m/e): 566.4 [(M+H)$^+$].

Example 63

{4-[(3S,4S)-4-[(S)-1-(5-Chloro-pyridin-2-yloxy)-ethyl]-3-(3,4-difluoro-phenyl)-piperidine-1-carbonyl]piperidin-1-yl}-(1-methyl-cyclopropyl)-methanone

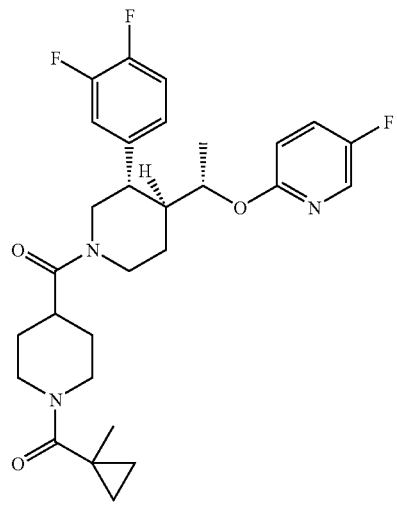

In analogy to the procedure described for the synthesis of [(3RS, 4RS)-3-(4-chloro-phenyl)-4-(5-chloro-pyridin-2-yloxymethyl)-piperidin-1-yl]-[4-(3-methyl-[1,2,4]oxadiazol-5-yl)-phenyl]-methanone (example 1, step i) the title compound was prepared from 5-Chloro-2-{(S)-1-[(3S,4S)-3-(3,4-difluoro-phenyl)-piperidin-4-yl]-ethoxy}-pyridine and 1-(1-methyl-cyclopropanecarbonyl)-piperidine-4-carboxylic acid (commercially available) as off-white solid. MS (m/e): 546.3 [(M+H)$^+$].

Example 64

[(3S,4S)-4-[(S)-1-(5-Chloro-pyridin-2-yloxy)-ethyl]-3-(3,4-difluoro-phenyl)-piperidin-1-yl]-(6-methyl-pyridazin-4-yl)-methanone

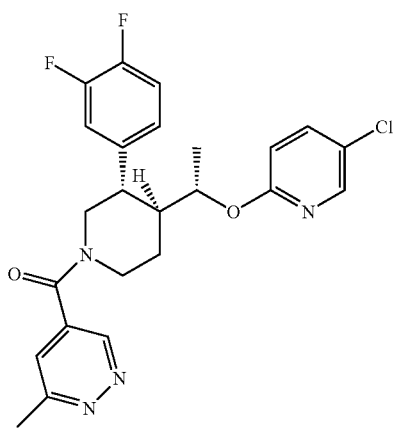

In analogy to the procedure described for the synthesis of [(3RS, 4RS)-3-(4-chloro-phenyl)-4-(5-chloro-pyridin-2-yloxymethyl)-piperidin-1-yl]-[4-(3-methyl-[1,2,4]oxadiazol-5-yl)-phenyl]-methanone (example 1, step i) the title compound was prepared from 5-Chloro-2-{(S)-1-[(3S,4S)-3-(3,4-difluoro-phenyl)-piperidin-4-yl]-ethoxy}-pyridine and 6-Methyl-pyridazine-4-carboxylic acid (WO2009019163) as light brown solid. MS (m/e): 473.2 [(M+H)$^+$].

Example 65

4-[(3S,4S)-4-[(S)-1-(5-Cyano-pyridin-2-yloxy)-ethyl]-3-(3,4-difluoro-phenyl)-piperidine-1-carbonyl]-3,4,5,6-tetrahydro-2H-[1,2']bipyridinyl-5'-carbonitrile

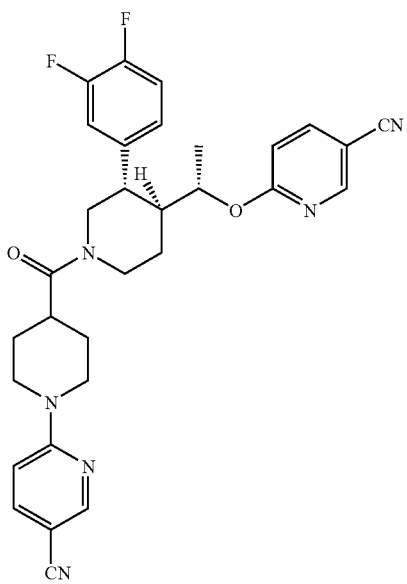

In analogy to the procedure described for the synthesis of 4-{(3S,4S)-3-(4-Chloro-phenyl)-4-[(S)-1-(3,4-dichloro-phenoxy)-ethyl]-piperidine-1-carbonyl}-3,4,5,6-tetrahydro-2H-[1,2']bipyridinyl-5'-carbonitrile (example 49) the respective piperidine derivative was prepared from (R)-1-[(3S,4S)-1-Benzyl-3-(3,4-difluoro-phenyl)-piperidin-4-yl]-ethanol and 3-cyano-6-hydroxy-pyridine via Mitsunobu reaction and subsequently the benzyl group was cleaved by treatment with 1-chloroethyl-chloroformate, DIPEA and methanol to yield 6-{(S)-1-[(3S,4S)-3-(3,4-Difluoro-phenyl)-piperidin-4-yl]-ethoxy}-nicotinonitrile. Coupling with 5'-Cyano-3,4,5,6-tetrahydro-2H-[1,2']bipyridinyl-4-carboxylic acid (commercially available) yielded the title compound as off-white solid. MS (m/e): 557.3 [(M+H)$^+$].

Example 66

6-((S)-1-{(3S,4S)-3-(3,4-Difluoro-phenyl)-1-[1-(1-methyl-cyclopropanecarbonyl)-piperidine-4-carbonyl]-piperidin-4-yl}-ethoxy)-nicotinonitrile

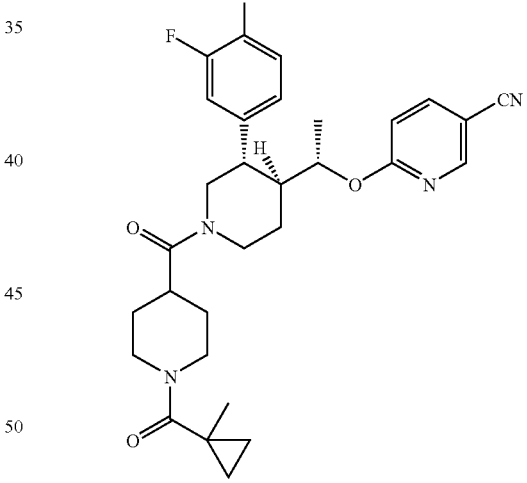

In analogy to the procedure described for the synthesis of [(3RS, 4RS)-3-(4-chloro-phenyl)-4-(5-chloro-pyridin-2-yloxymethyl)-piperidin-1-yl]-[4-(3-methyl-[1,2,4]oxadiazol-5-yl)-phenyl]-methanone (example 1, step i) the title compound was prepared from 6-{(S)-1-[(3S,4S)-3-(3,4-Difluoro-phenyl)-piperidin-4-yl]-ethoxy}-nicotinonitrile and 1-(1-methyl-cyclopropanecarbonyl)-piperidine-4-carboxylic acid (commercially available) as light brown solid. MS (m/e): 537.4 [(M+H)$^+$].

Example 67

6-{(S)-1-[(3S,4S)-3-(3,4-Difluoro-phenyl)-1-(6-methyl-pyridazine-4-carbonyl)-piperidin-4-yl]-ethoxy}-nicotinonitrile

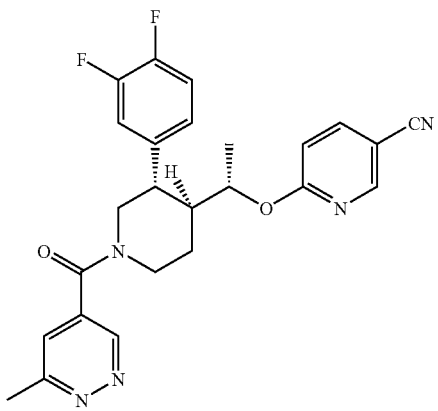

In analogy to the procedure described for the synthesis of [(3RS, 4RS)-3-(4-chloro-phenyl)-4-(5-chloro-pyridin-2-yloxymethyl)-piperidin-1-yl]-[4-(3-methyl-[1,2,4]oxadiazol-5-yl)-phenyl]-methanone (example 1, step i) the title compound was prepared from 6-{(S)-1-[(3S,4S)-3-(3,4-Difluoro-phenyl)-piperidin-4-yl]-ethoxy}-nicotinonitrile and 6-Methyl-pyridazine-4-carboxylic acid (WO2009019163) as light brown solid. MS (m/e): 464.3 [(M+H)$^+$].

Example 68 & Example 69

4-{(3S,4S)-3-(4-Chloro-phenyl)-4-[(SR)-1-(5-cyano-pyridin-2-ylamino)-ethyl]-piperidine-1-carbonyl}-3,4,5,6-tetrahydro-2H-[1,2']bipyridinyl-5'-carbonitrile & 4-{(3S,4S)-3-(4-Chloro-phenyl)-4-[(RS)-1-(5-cyano-pyridin-2-ylamino)-ethyl]-piperidine-1-carbonyl}-3,4,5,6-tetrahydro-2H-[1,2']bipyridinyl-5'-carbonitrile

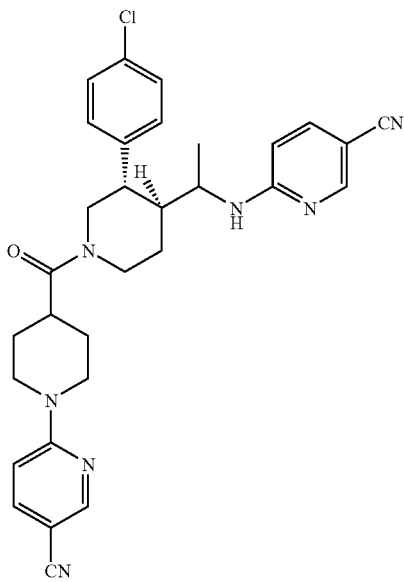

a) 1-[(3S,4S)-1-Benzyl-3-(4-chloro-phenyl)-piperidin-4-yl]-ethanone oxime

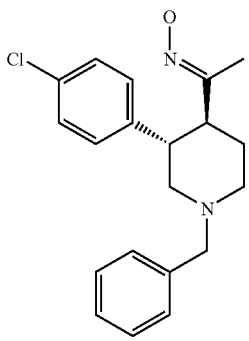

A mixture of 2 g (6.1 mmol) 1-[(3S,4S)-1-Benzyl-3-(4-chloro-phenyl)-piperidin-4-yl]-ethanone, 0.869 g (12.5 mmol) hydroxylamine, hydrochloride and 1.03 g (12.5 mmol) sodium acetate in 25 mL ethanol was heated to reflux for 2 h. After cooling to room temperature water was added and the mixture was extracted with ethyl acetate. The combined organic phases were dried with Na$_2$SO$_4$, filtered and evaporated to dryness. The residue was purified by flash column chromatography on silica eluting with a ethyl acetate. The product containing fractions were evaporated to yield 1.6 g (77%) of the title compound as colorless viscous oil. MS (m/e): 343.2 [(M+H)$^+$].

b) 1-[(3S,4S)-1-Benzyl-3-(4-chloro-phenyl)-piperidin-4-yl]-ethylamine

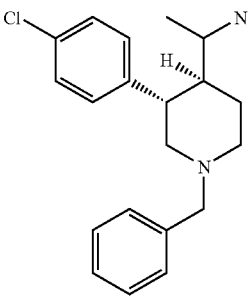

A solution of 1.6 g (4.7 mmol) 1-[(3S,4S)-1-Benzyl-3-(4-chloro-phenyl)-piperidin-4-yl]-ethanone oxime in 300 mL methanol was hydrogenated over Raney Nickel (3.5 bar, 30° C., 23 h). The mixture was filtered and evaporated to dryness. The residue was purified by column chromatography over silica eluting with a gradient formed from DCM, methanol and NH$_3$aq. to yield after evaporation of the product containing fractions 0.7 g (45%) of the title compound as colorless viscous oil. MS (m/e): 329.4 [(M+H)$^+$].

c) 6-{1-[(3S,4S)-1-Benzyl-3-(4-chloro-phenyl)-piperidin-4-yl]-ethylamino}-nicotinonitrile

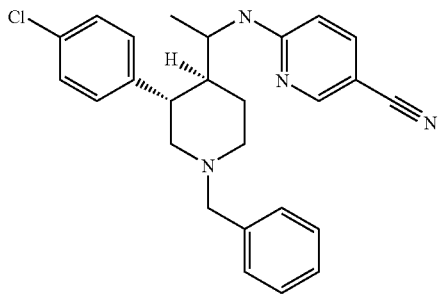

A mixture of 610 mg (1.8 mmol) 1-[(3S,4S)-1-Benzyl-3-(4-chloro-phenyl)-piperidin-4-yl]-ethylamine, 1.18 g (2.8 mmol) 2-bromo-5-cyano-pyridine and 0.838 g (2.8 mmol) DIPEA in 3.5 mL DMF was heated to 60° C. for 3 days. The mixture was evaporated, $Na_2CO_3$aq. was added and the mixture was extracted with ethyl acetate. The combined organic phases were dried with $Na_2SO_4$ and evaporated to dryness. The residue was purified by column chromatography on silica eluting with a gradient formed from DCM, methanol and $NH_3$aq. to yield after evaporation of the product containing fractions 0.526 g (66%) of the title compound as off-white foam. MS (m/e): 431.4 [(M+H)$^+$].

d) 6-{1-[(3S,4S)-3-(4-Chloro-phenyl)-piperidin-4-yl]-ethylamino}-nicotinonitrile

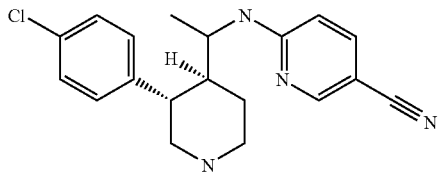

In analogy to the procedure described for the synthesis of 5-chloro-2-[(3RS, 4RS)-3-(4-chloro-phenyl)-piperidin-4-yl-methoxy]-pyridine; hydrochloride (example 1, step h) the title compound was prepared from 6-{1-[(3S,4S)-1-Benzyl-3-(4-chloro-phenyl)-piperidin-4-yl]-ethylamino}-nicotinonitrile as light yellow viscous oil. MS (m/e): 341.2 [(M+H)$^+$].

e) 4-{(3S,4S)-3-(4-Chloro-phenyl)-4-[(SR)-1-(5-cyano-pyridin-2-ylamino)-ethyl]-piperidine-1-carbonyl}-3,4,5,6-tetrahydro-2H-[1,2']bipyridinyl-5'-carbonitrile & 4-{(3S,4S)-3-(4-Chloro-phenyl)-4-[(RS)-1-(5-cyano-pyridin-2-ylamino)-ethyl]-piperidine-1-carbonyl}-3,4,5,6-tetrahydro-2H-[1,2']bipyridinyl-5'-carbonitrile In analogy to the procedure described for the synthesis of [(3RS, 4RS)-3-(4-chloro-phenyl)-4-(5-chloro-pyridin-2-yloxymethyl)-piperidin-1-yl]-[4-(3-methyl-[1,2,4]oxadiazol-5-yl)-phenyl]-methanone (example 1, step i) the title compounds were prepared from 6-{1-[(3S,4S)-3-(4-Chloro-phenyl)-piperidin-4-yl]-ethylamino}-nicotinonitrile and 5'-Cyano-3,4,5,6-tetrahydro-2H-[1,2']bipyridinyl-4-carboxylic acid (commercially available) with subsequent separation via preparative HPLC on chiral pak AD eluting with heptane/ethanol to yield 4-{(3S,4S)-3-(4-Chloro-phenyl)-4-[(SR)-1-(5-cyano-pyridin-2-ylamino)-ethyl]-piperidine-1-carbonyl}-3,4,5,6-tetrahydro-2H-[1,2']bipyridinyl-5'-carbonitrile as off-white solid. MS (m/e): 554.4 [(M+H)$^+$] and 4-{(3S,4S)-3-(4-Chloro-phenyl)-4-[(RS)-1-(5-cyano-pyridin-2-ylamino)-ethyl]-piperidine-1-carbonyl}-3,4,5,6-tetrahydro-2H-[1,2']bipyridinyl-5'-carbonitrile as off-white solid. MS (m/e): 554.4 [(M+H)$^+$]

As mentioned earlier, the compounds of formula I and their pharmaceutically acceptable addition salts possess valuable pharmacological properties. Compounds of the present invention are antagonists of neurokinin 3 (NK-3) receptors. The compounds were investigated in accordance with the tests given hereinafter.

Experimental Procedure

The compounds were investigated in accordance with the tests given hereinafter. [$^3$H]SR142801 competition binding assay hNK3 receptor binding experiment were performed using [$^3$H]SR142801 (Catalog No. TRK1035, specific activity: 74.0 Ci/mmol, Amersham, GE Healthcare UK limited, Buckinghamshire, UK) and membrane isolated from HEK293 cells transiently expressing recombinant human NK3 receptor. After thawing, the membrane homogenates were centrifuged at 48,000×g for 10 min at 4° C., the pellets were resuspended in the 50 mM Tris-HCl, 4 mM $MnCl_2$, 1 µM phosphoramidon, 0.1% BSA binding buffer at pH 7.4 to a final assay concentration of 5 µg protein/well. For inhibition experiments, membranes were incubated with [$^3$H]SR142801 at a concentration equal to $K_D$ value of radioligand and 10 concentrations of the inhibitory compound (0.0003-10 µM) (in a total reaction volume of 500 µl) for 75 min at room temperature (RT). At the end of the incubation, membranes were filtered onto unitfilter (96-well white microplate with bonded GF/C filter preincubated 1 h in 0.3% PEI+0.3% BSA, Packard BioScience, Meriden, Conn.) with a Filtermate 196 harvester (Packard BioScience) and washed 4 times with ice-cold 50 mM Tris-HCl, pH 7.4 buffer. Nonspecific binding was measured in the presence of 10 µM SB222200 for both radioligands. The radioactivity on the filter was counted (5 min) on a Packard Top-count microplate scintillation counter with quenching correction after addition of 45 µl of microscint 40 (Can berra Packard S. A., Zürich, Switzerland) and shaking for 1 h. Inhibition curves were fitted according to the Hill equation: $y=100/(1+(x/IC_{50})^{nH})$, where $n_H$=slope factor using Excel-fit 4 software (Microsoft). $IC_{50}$ values were derived from the inhibition curve and the affinity constant ($K_i$) values were calculated using the Cheng-Prussoff equation $K_i=IC_{50}/(1+[L]/K_D)$ where [L] is the concentration of radioligand and $K_D$ is its dissociation constant at the receptor, derived from the saturation isotherm. All experiments were performed in duplicate and the mean±standard error (SEM) of the individual $K_i$ values was calculated.

Compounds with a hNK-3 receptor affinity<0.010 µM are preferred. Results for some compounds of the invention are shown in the following Table 1.

TABLE 1

| Example | Data $K_i$ [µM] |
| --- | --- |
| 5 | 0.0041 |
| 7 | 0.0026 |

TABLE 1-continued

| Example | Data $K_i$ [µM] |
|---|---|
| 10 | 0.0036 |
| 11 | 0.0018 |
| 12 | 0.0023 |
| 13 | 0.0003 |
| 14 | 0.0026 |
| 16 | 0.0016 |
| 17 | 0.0056 |
| 18 | 0.0012 |
| 19 | 0.0014 |
| 20 | 0.0002 |
| 21 | 0.0047 |
| 23 | 0.0011 |
| 24 | 0.0087 |
| 25 | 0.0015 |
| 26 | 0.0051 |
| 27 | 0.0003 |
| 28 | 0.003 |
| 29 | 0.0077 |
| 31 | 0.0083 |
| 32 | 0.0058 |
| 33 | 0.0013 |
| 47 | 0.0099 |
| 49 | 0.0055 |
| 50 | 0.0013 |
| 51 | 0.0019 |
| 52 | 0.0006 |
| 53 | 0.0006 |
| 54 | 0.0017 |
| 55 | 0.0009 |
| 56 | 0.0038 |
| 57 | 0.0014 |
| 58 | 0.002 |
| 61 | 0.0015 |
| 62 | 0.0002 |
| 63 | 0.0035 |
| 65 | 0.0004 |
| 66 | 0.0046 |
| 68 | 0.0014 |

The present invention also provides pharmaceutical compositions containing compounds of the invention, for example, compounds of formula I or pharmaceutically acceptable salts thereof and a pharmaceutically acceptable carrier. Such pharmaceutical compositions can be in the form of tablets, coated tablets, dragées, hard and soft gelatin capsules, solutions, emulsions or suspensions. The pharmaceutical compositions also can be in the form of suppositories or injectable solutions.

The pharmaceutical compositions of the invention, in addition to one or more compounds of the invention, contain a pharmaceutically acceptable carrier. Suitable pharmaceutically acceptable carriers include pharmaceutically inert, inorganic or organic carriers. Lactose, corn starch or derivatives thereof, talc, stearic acid or its salts etc can be used as such excipients e.g. for tablets, dragées and hard gelatin capsules.

Suitable excipients for soft gelatin capsules are e.g. vegetable oils, waxes, fats, semi-solid and liquid polyols etc. Suitable excipients for the manufacture of solutions and syrups are e.g. water, polyols, saccharose, invert sugar, glucose etc. Suitable excipients for injection solutions are e.g. water, alcohols, polyols, glycerol, vegetable oils etc. Suitable excipients for suppositories are e.g. natural or hardened oils, waxes, fats, semi-liquid or liquid polyols etc.

Moreover, the pharmaceutical compositions can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The dosage at which compounds of the invention can be administered can vary within wide limits and will, of course, be fitted to the individual requirements in each particular case. In general, in the case of oral administration a daily dosage of about 10 to 1000 mg per person of a compound of general formula I should be appropriate, although the above upper limit can also be exceeded when necessary.

Example A

Tablets of the following composition are manufactured in the usual manner:

|  | mg/tablet |
|---|---|
| Active substance | 5 |
| Lactose | 45 |
| Corn starch | 15 |
| Microcrystalline cellulose | 34 |
| Magnesium stearate | 1 |
| Tablet weight | 100 |

Example B

Capsules of the following composition are manufactured:

|  | mg/capsule |
|---|---|
| Active substance | 10 |
| Lactose | 155 |
| Corn starch | 30 |
| Talc | 5 |
| Capsule fill weight | 200 |

The active substance, lactose and corn starch are firstly mixed in a mixer and then in a comminuting machine. The mixture is returned to the mixer, the talc is added thereto and mixed thoroughly. The mixture is filled by machine into hard gelantine capsules.

Example C

Suppositories of the following composition are manufactured:

|  | mg/supp. |
|---|---|
| Active substance | 15 |
| Suppository mass | 1285 |
| Total | 1300 |

The suppository mass is melted in a glass or steel vessel, mixed thoroughly and cooled to 45° C. Thereupon, the finely powdered active substance is added thereto and stirred until it has dispersed completely. The mixture is poured into suppository moulds of suitable size, left to cool, the suppositories are then removed from the moulds and packed individually in wax paper or metal foil.

The invention claimed is:
1. A compound of formula Ic

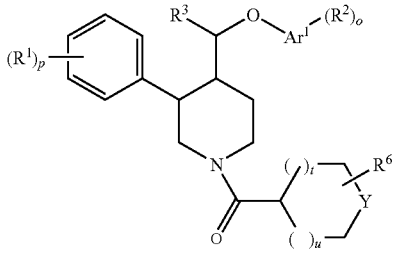

wherein
Ar¹ is a six-membered heteroaryl;
R¹ is hydrogen, halogen, lower alkyl, lower alkoxy or lower alkyl substituted by halogen;
R² is hydrogen, halogen, cyano, lower alkyl, or lower alkyl substituted by halogen;
R³ is hydrogen or lower alkyl;
Y is —N(R⁷')—;
R⁷' is a 6-membered heteroaryl group, optionally substituted by cyano or is C(O)-cycloalkyl, wherein the cycloalkyl group is optionally substituted by lower alkyl;
R⁶ is hydrogen;
p is 1;
o is 1;
t is 1; and
u is 1;
or a pharmaceutically active salt, a racemic mixture, an enantiomer, an optical isomer or a tautomeric form thereof.

2. The compound of claim 1, selected from the group consisting of
{4-[(3RS,4RS)-3-(4-chloro-phenyl)-4-(5-trifluoromethyl-pyridin-2-yloxymethyl)-piperidine-1-carbonyl]-piperidin-1-yl}-(1-methyl-cyclopropyl)-methanone;
{4-[(3RS,4RS)-3-(4-chloro-phenyl)-4-(5-chloro-pyridin-2-yloxymethyl)-piperidine-1-carbonyl]-piperidin-1-yl}-(1-methyl-cyclopropyl)-methanone;
(4-{(3SR,4SR)-3-(4-chloro-phenyl)-4-[(SR)-1-(5-chloro-pyridin-2-yloxy)-ethyl]-piperidine-1-carbonyl}-piperidin-1-yl)-(1-methyl-cyclopropyl)-methanone;
(4-{(3S,4S)-3-(4-chloro-phenyl)-4-[(S)-1-(5-chloro-pyridin-2-yloxy)-ethyl]-piperidine-1-carbonyl}-piperidin-1-yl)-(1-methyl-cyclopropyl)-methanone;
(4-{(3R,4R)-3-(4-chloro-phenyl)-4-[(R)-1-(5-chloro-pyridin-2-yloxy)-ethyl]-piperidine-1-carbonyl}-piperidin-1-yl)-(1-methyl-cyclopropyl)-methanone;
4-{(3S,4S)-3-(4-chloro-phenyl)-4-[(S)-1-(5-chloro-pyridin-2-yloxy)-ethyl]-piperidine-1-carbonyl}-3,4,5,6-tetrahydro-2H-[1,2']bipyridinyl-5'-carbonitrile;
4-{(3S,4S)-3-(4-chloro-phenyl)-4-[(S)-1-(5-trifluoromethyl-pyridin-2-yloxy)-ethyl]-piperidine-1-carbonyl}-3,4,5,6-tetrahydro-2H-[1,2']bipyridinyl-5'-carbonitrile;
6-((S)-1-{(3S,4S)-3-(4-chloro-phenyl)-1-[1-(1-methyl-cyclopropanecarbonyl)-piperidine-4-carbonyl]-piperidin-4-yl}-ethoxy)-nicotinonitrile; and
4-{(3S,4S)-3-(4-chloro-phenyl)-4-[(S)-1-(5-cyano-pyridin-2-yloxy)-ethyl]-piperidine-1-carbonyl}-3,4,5,6-tetrahydro-2H-[1,2']bipyridinyl-5'-carbonitrile.

3. The compound of claim 1, selected from the group consisting of
{4-[(3SR,4SR)-4-(5-chloro-pyridin-2-yloxymethyl)-3-(3,4-difluoro-phenyl)-piperidine-1-carbonyl]-piperidin-1-yl}-(1-methyl-cyclopropyl)-methanone;
4-[(3S,4S)-4-(5-chloro-pyridin-2-yloxymethyl)-3-(3,4-difluoro-phenyl)-piperidine-1-carbonyl]-3,4,5,6-tetrahydro-2H-[1,3']bipyridinyl-6'-carbonitrile;
4-[(3S,4S)-4-(5-chloro-pyridin-2-yloxymethyl)-3-phenyl-piperidine-1-carbonyl]-3,4,5,6-tetrahydro-2H-[1,2']bipyridinyl-5'-carbonitrile;
4-{(3S,4S)-3-(4-chloro-phenyl)-4-[(S)-1-(3,4-dichloro-phenoxy)-ethyl]-piperidine-1-carbonyl}-3,4,5,6-tetrahydro-2H-[1,2']bipyridinyl-5'-carbonitrile;
4-{(3S,4S)-3-(4-chloro-phenyl)-4-[(S)-1-(4-trifluoromethyl-phenoxy)-ethyl]-piperidine-1-carbonyl}-3,4,5,6-tetrahydro-2H-[1,2']bipyridinyl-5'-carbonitrile;
4-{(3S,4S)-3-(4-chloro-phenyl)-4-[(S)-1-(4-cyano-phenoxy)-ethyl]-piperidine-1-carbonyl}-3,4,5,6-tetrahydro-2H-[1,2']bipyridinyl-5'-carbonitrile;
4-{(3S,4S)-3-(4-chloro-phenyl)-4-[(S)-1-(5-fluoro-pyridin-2-yloxy)-ethyl]-piperidine-1-carbonyl}-3,4,5,6-tetrahydro-2H-[1,2']bipyridinyl-5'-carbonitrile;
4-{(3S,4S)-3-(4-chloro-phenyl)-4-[(S)-1-(4-fluoro-phenoxy)-ethyl]-piperidine-1-carbonyl}-3,4,5,6-tetrahydro-2H-[1,2']bipyridinyl-5'-carbonitrile;
4-{(3S,4S)-3-(4-chloro-phenyl)-4-[(S)-1-(3,4-difluoro-phenoxy)-ethyl]-piperidine-1-carbonyl}-3,4,5,6-tetrahydro-2H-[1,2']bipyridinyl-5'-carbonitrile; and
4-[(3S,4S)-4-[(S)-1-(4-chloro-phenoxy)-ethyl]-3-(4-chloro-phenyl)-piperidine-1-carbonyl]-3,4,5,6-tetrahydro-2H-[1,2']bipyridinyl-5'-carbonitrile.

4. The compound of claim 1, selected from the group consisting of
4-{(3S,4S)-3-(4-chloro-phenyl)-4-[(S)-1-(3-fluoro-phenoxy)-ethyl]-piperidine-1-carbonyl}-3,4,5,6-tetrahydro-2H-[1,2']bipyridinyl-5'-carbonitrile;
4-[(3S,4S)-3-(4-chloro-phenyl)-4-((S)-1-p-tolyloxy-ethyl)-piperidine-1-carbonyl]-3,4,5,6-tetrahydro-2H-[1,2']bipyridinyl-5'-carbonitrile;
4-{(3S,4S)-3-(4-cloro-phenyl)-4-[(S)-1-(5-methyl-pyridin-2-yloxy)-ethyl]-piperidine-1-carbonyl}-3,4,5,6-tetrahydro-2H-[1,2']bipyridinyl-5'-carbonitrile;
4-{(3S,4S)-3-(4-chloro-phenyl)-4-[(S)-1-(5-fluoro-pyrimidin-2-yloxy)-ethyl]-piperidine-1-carbonyl}-3,4,5,6-tetrahydro-2H-[1,2']bipyridinyl-5'-carbonitrile;
4-[(3S,4S)-4-[(S)-1-(5-chloro-pyridin-2-yloxy)-ethyl]-3-(3,4-difluoro-phenyl)-piperidine-1-carbonyl]-3,4,5,6-tetrahydro-2H-[1,2']bipyridinyl-5'-carbonitrile;
{4-[(3S,4S)-4-[(S)-1-(5-chloro-pyridin-2-yloxy)-ethyl]-3-(3,4-difluoro-phenyl)-piperidine-1-carbonyl]-piperidin-1-yl}-(1-methyl-cyclopropyl)-methanone;
4-[(3S,4S)-4-[(S)-1-(5-cyano-pyridin-2-yloxy)-ethyl]-3-(3,4-difluoro-phenyl)-piperidine-1-carbonyl]-3,4,5,6-tetrahydro-2H-[1,2']bipyridinyl-5'-carbonitrile;
6-((S)-1-{(3S,4S)-3-(3,4-difluoro-phenyl)-1-[1-(1-methyl-cyclopropanecarbonyl)-piperidine-4-carbonyl]-piperidin-4-yl}-ethoxy)-nicotinonitrile; and
4-{(3S,4S)-3-(4-chloro-phenyl)-4-[(SR)-1-(5-cyano-pyridin-2-ylamino)-ethyl]-piperidine-1-carbonyl}-3,4,5,6-tetrahydro-2H-[1,2']bipyridinyl-5'-carbonitrile.

5. A pharmaceutical composition comprising a therapeutically effective amount of a compound of formula Ic

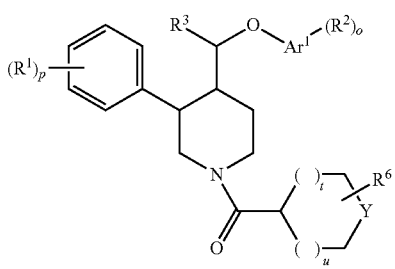

Ic wherein
Ar¹ is a six-membered heteroaryl;
R¹ is hydrogen, halogen, lower alkyl, lower alkoxy or lower alkyl substituted by halogen;
R² is hydrogen, halogen, cyano, lower alkyl, or lower alkyl substituted by halogen;
R³ is hydrogen or lower alkyl;
Y is —N(R⁷')—;
R⁷' is a 6-membered heteroaryl group, optionally substituted by cyano or is C(O)-cycloalkyl, wherein the cycloalkyl group is optionally substituted by lower alkyl;
R⁶ is hydrogen;
p is 1;
o is 1;
t is 1; and
u is 1;
or a pharmaceutically active salt, a racemic mixture, an enantiomer, an optical isomer or a tautomeric form thereof and a pharmaceutically acceptable carrier.

* * * * *